United States Patent
Mori et al.

(10) Patent No.: US 7,247,440 B2
(45) Date of Patent: Jul. 24, 2007

(54) METHOD OF SCREENING PREVENTIVES OR REMEDIES FOR OBESITY

(75) Inventors: Masaaki Mori, Ibaraki (JP); Yukio Shimomura, Ibaraki (JP); Mika Goto, Hyogo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 449 days.

(21) Appl. No.: 10/477,726

(22) PCT Filed: May 14, 2002

(86) PCT No.: PCT/JP02/04635

§ 371 (c)(1),
(2), (4) Date: Nov. 14, 2003

(87) PCT Pub. No.: WO02/093161

PCT Pub. Date: Nov. 21, 2002

(65) Prior Publication Data

US 2004/0110231 A1   Jun. 10, 2004

(30) Foreign Application Priority Data

May 15, 2001   (JP) ............................. 2001-145411

(51) Int. Cl.
*G01N 33/53* (2006.01)
(52) U.S. Cl. ..................................................... 435/7.1
(58) Field of Classification Search ................... None
See application file for complete search history.

(56) References Cited

FOREIGN PATENT DOCUMENTS

| EP | 1 293 567 A1 | 3/2003 |
|---|---|---|
| WO | WO 95/12670 | 5/1995 |
| WO | WO 00/22129 | 4/2000 |
| WO | WO 01/98494 | 12/2001 |
| WO | WO 01/98494 A1 | 12/2001 |
| WO | WO 02/44368 | 6/2002 |

*Primary Examiner*—Ralph Gitomer
*Assistant Examiner*—Bin Shen
(74) *Attorney, Agent, or Firm*—Edwards Angell Palmer & Dodge LLP; Gregory Butler, Esq.

(57) ABSTRACT

The present invention provides preventive/therapeutic agents for anorexia nervosa and preventive/therapeutic agents for obesity. More specifically, the present invention provides a method and kit for screening a compound or its salt that changes the binding properties of GPR7 to a polypeptide capable of binding specifically to GPR7.

4 Claims, 14 Drawing Sheets

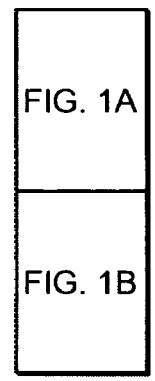

FIG. 1

```
1    atgcaggccgctgggcacccagagccccttgacagcaggggctccttctccctccccacg
     M  Q  A  A  G  H  P  E  P  L  D  S  R  G  S  F  S  L  P  T
61   atgggtgccaacgtctctcaggacaatggcactggccacaatgccaccttctccgagcca
     M  G  A  N  V  S  Q  D  N  G  T  G  H  N  A  T  F  S  E  P
121  ctgccgttcctctatgtgctcctgcccgccgtgtactccgggatcgtgctgtggggctg
     L  P  F  L  Y  V  L  L  P  A  V  Y  S  G  I  C  A  V  G  L
181  actggcaacacggccgtcatccttgtaatcctaagggcgcccaagatgaagacggtgacc
     T  G  N  T  A  V  I  L  V  I  L  R  A  P  K  M  K  T  V  T
241  aacgtgttcatcctgaacctggccgtcgccgacgggctcttcacgctggtactgcccgtc
     N  V  F  I  L  N  L  A  V  A  D  G  L  F  T  L  V  L  P  V
301  aacatcgcggagcacctgctgcagtactggcccttcggggagctgctctgcaagctggtg
     N  I  A  E  H  L  L  Q  Y  W  P  F  G  E  L  L  C  K  L  V
```

FIG. 1A

```
361  ctggccgtcgaccactacaacatcttctccagcatctacttcctagccgtgatgagcgtg
      L  A  V  D  H  Y  N  I  F  S  S  I  Y  F  L  A  V  M  S  V
421  gaccgatacctggtggtgctggccaccgtgaggtcccgccacatgccctggcgcaccfac
      D  R  Y  L  V  V  L  A  T  V  R  S  R  H  M  P  W  R  T  Y
481  cgggggcgaaggtcgccagcctgtgtgtctggctgggcgtcacggtcctggttctgccc
      R  G  A  K  V  A  S  L  C  V  W  L  G  V  T  V  L  V  L  P
541  ttcttctctttcgctggcgtctacagcaacgagctgcaggtcccaagctgtgggctgagc
      F  F  S  F  A  G  V  Y  S  N  E  L  Q  V  P  S  C  G  L  S
601  ttcccgtggccccgagcgggtctggttcaaggccagccgtgtctacactttggtcctgggc
      F  P  W  P  E  R  V  W  F  K  A  S  R  V  Y  T  L  V  L  G
661  ttcgtgctgccccgtgtgcaccatctgtgtgctctacacagacctcctgcgcaggctgcgg
      F  V  L  P  V  C  T  I  C  V  L  Y  T  D  L  L  R  R  L  R
721  gccgtgcggctccgctctggagccaaggctctaggcaaggccaggcggaaggtgaccgtc
      A  V  R  L  R  S  G  A  K  A  L  G  K  A  R  R  K  V  T  V
781  ctggtcctcgtcgtgctggccgtgtgcctcctctgctggacgcccttccacctggcctct
      L  V  L  V  V  L  A  V  C  L  L  C  W  T  P  F  H  L  A  S
841  gtcgtggccctgaccacggacctgccccagaccccactggtcatcagtatgtcctacgtc
      V  V  A  L  T  T  D  L  P  Q  T  P  L  V  I  S  M  S  Y  V
901  atcaccagcctcacgtacgccaactcgtgcctgaaccccttcctctacgcctttctagat
      I  T  S  L  T  Y  A  N  S  C  L  N  P  F  L  Y  A  F  L  D
961  gacaacttccggaagaacttccgcagcatattgcggtgctga    SEQ ID NO: 32[a]
      D  N  F  R  K  N  F  R  S  I  L  R  C    SEQ ID NO: 4[b]
```

FIG. 1B

```
                                  GGC GGG GCC ACC GAG CGG TTA TAG CTG GGC CTG CAG GGG ACC    42
CAC GGC TCG CCT CCA GCC TCC TGC GCT CCG GTA CCT GGG CGT CCC AAC TCC ACT GCG CGC   102
CCA AAC CCA GCC GAG CCG GTT CGT GGC CCG CCC CGC CGG GCG GCC GTC GAC GCG AGC GCC   162

CTG GCG TGG CGC CCA GGG GAG CGG GGG GCT CCC GCG AGC CGG CCG CGG CTG GCA CTG CTG   222
Leu Ala Trp Arg Pro Gly Glu Arg Gly Ala Pro Ala Ser Arg Pro Arg Leu Ala Leu Leu    20

CTG CTT CTG CTC CTG CTG CCG CTG CCC TCC GGC GCG TGG TAC AAG CAC GTG GCG AGT CCC   282
Leu Leu Leu Leu Leu Leu Pro Leu Pro Ser Gly Ala Trp Tyr Lys His Val Ala Ser Pro    40

CGC TAC CAC ACG GTG GGC CGC GCC GCT GGC CTG CTC ATG GGG CTG CGT CGC TCA CCC TAT   342
Arg Tyr His Thr Val Gly Arg Ala Ala Gly Leu Leu Met Gly Leu Arg Arg Ser Pro Tyr    60

CTG TGG CGC CGC GCG CTG CGC GCG GCC GCC GGG CCC CTG GCC AGG GAC ACC CTC TCC CCC   402
Leu Trp Arg Arg Ala Leu Arg Ala Ala Ala Gly Pro Leu Ala Arg Asp Thr Leu Ser Pro    80

GAA CCC GCA GCC CGC GAG GCT CCT CTC CTG CTG CCC TCG TGG GTT CAG GAG CTG TGG GAG   462
Glu Pro Ala Ala Arg Glu Ala Pro Leu Leu Leu Pro Ser Trp Val Gln Glu Leu Trp Glu   100

ACG CGA CGC AGG AGC TCC CAG GCA GGG ATC CCC GTC CGT GCG CCC CGG AGC CCG CGC GCC   522
Thr Arg Arg Arg Ser Ser Gln Ala Gly Ile Pro Val Arg Ala Pro Arg Ser Pro Arg Ala   120

CCA GAG CCT GCG CTG GAA CCG GAG TCC CTG GAC TTC AGC GGA GCT GGC CAG AGA CTT CGG   582
Pro Glu Pro Ala Leu Glu Pro Glu Ser Leu Asp Phe Ser Gly Ala Gly Gln Arg Leu Arg   140

AGA GAC GTC TCC CGC CCA GCG GTG GAC CCC GCA GCA AAC CGC CTT GGC CTG CCC TGC CTG   642
Arg Asp Val Ser Arg Pro Ala Val Asp Pro Ala Ala Asn Arg Leu Gly Leu Pro Cys Leu   160

GCC CCC GGA CCG TTC TGA CAG CGT CCC CGC CCC GCC CGT GGC GCC TCC GCG CCT GAC CCA   702
Ala Pro Gly Pro Phe *** SEQ ID NO: 42(c)                                           165

GGA GGA GTG GCC GCG CG   SEQ ID NO: 41                                             719
```

FIG. 8

```
                          CC TCC GGA GCC AGT TCC TGG TCC GCC CCG CCG GGA GCC GTC AGC   44

ATG AAC CCC CGG GCA CGC GGC ATG GGA GCG CGG GGC CCG GGA CCG GGG GCC ACT GCG AGG  104
Met Asn Pro Arg Ala Arg Gly Met Gly Ala Arg Gly Pro Gly Pro Gly Ala Thr Ala Arg   20

CGC CGG CTG CTG GCA TTG CTG TTA CTG CTG CTG CTG CTG CCG CTG CCC GCC CGT GCC TGG  164
Arg Arg Leu Leu Ala Leu Leu Leu Leu Leu Leu Leu Leu Pro Leu Pro Ala Arg Ala Trp   40

TAC AAG CAC ACG GCG AGT CCC CGC TAC CAC ACG GTG GGC CGC GCC GCG GGC CTG CTC ATG  224
Tyr Lys His Thr Ala Ser Pro Arg Tyr His Thr Val Gly Arg Ala Ala Gly Leu Leu Met   60

GGG CTG CGC CGC TCG CCC TAC ATG TGG CGC CGC GCG CTG CGC CCG GCG GCC GGG CCC CTG  284
Gly Leu Arg Arg Ser Pro Tyr Met Trp Arg Arg Ala Leu Arg Pro Ala Ala Gly Pro Leu   80

GCC TGG GAC ACT TTC GGC CAG GAC GTG CCC CCT CGG GGA CCC TCC GCC AGG AAC GCC CTC  344
Ala Trp Asp Thr Phe Gly Gln Asp Val Pro Pro Arg Gly Pro Ser Ala Arg Asn Ala Leu  100

TCT CCG GGG CCC GCC CCT CGC GAC GCT CCG CTG CTT CCC CCC GGG GTT CAG ACA CTG TGG  404
Ser Pro Gly Pro Ala Pro Arg Asp Ala Pro Leu Leu Pro Pro Gly Val Gln Thr Leu Trp  120

CAG GTG CGA CGC GGA AGC TTC CGC TCC GGG ATC CCG GTC AGT GCG CCC CGC AGC CCG CGC  464
Gln Val Arg Arg Gly Ser Phe Arg Ser Gly Ile Pro Val Ser Ala Pro Arg Ser Pro Arg  140

GCC CGG GGG TCC GAG CCG CAA CCG GAA TTG GGC GCC TCT TCC TGG ACC TCG GCG GAG TAG  524
Ala Arg Gly Ser Glu Pro Gln Pro Glu Leu Gly Ala Ser Ser Trp Thr Ser Ala Glu ***  159
                                                                SEQ ID NO: 55(d)
ACC AGA GCC TTC GGA GAG TCT TCA GCT CAG CGG TGG TCT GC  SEQ ID NO: 54           565
```

FIG. 9

```
                                    TGT AGT CGC ACC AAC TGA CTA GTC TCT TCC ATC CTC    36
CGG AGC TCC GAC GTT CTC GGG GAC ATA AAC CCT GTT CTT GTC CTA ACC CGC CAA GGG GCC        96

ATG GAC TTG AGC GCG CTG GCG TCG AGC AGA GAA GTA CGG GGC CCT GGG CCC GGG GCT CCG        156
Met Asp Leu Ser Ala Leu Ala Ser Ser Arg Glu Val Arg Gly Pro Gly Pro Gly Ala Pro        20

GTG AAC CGG CCC CTG CTA CCG CTA CTG CTG CTT CTG CTC TTG CTA CCT CTG CCC GCC AGC        216
Val Asn Arg Pro Leu Leu Pro Leu Leu Leu Leu Leu Leu Leu Pro Leu Pro Ala Ser            40

GCC │TGG TAC AAG CAC GTG GCG AGC CCT CGC TAT CAC ACA GTG GGT CGT GCC TCC GGG CTG       276
Ala │Trp Tyr Lys His Val Ala Ser Pro Arg Tyr His Thr Val Gly Arg Ala Ser Gly Leu       60

CTC ATG GGG CTG│CGC CGC TCG CCC TAC CTG TGG CGC CGT GCC TTG GGT GGG GCC GCT GGA        336
Leu Met Gly Leu│Arg Arg Ser Pro Tyr Leu Trp Arg Arg Ala Leu Gly Gly Ala Ala Gly        80

CCG CTC GTG GGG CTC CCG GGA CAG ATG GCC CGC AGC GCT CTC CTG CTT CCT TCC CCC GGG        396
Pro Leu Val Gly Leu Pro Gly Gln Met Ala Arg Ser Ala Leu Leu Leu Pro Ser Pro Gly        100

CAG GAG CTG TGG GAG GTA CGA AGC AGG AGT TCA CCG GCA GGA CTT CCC GTG CAT GCA ACC        456
Gln Glu Leu Trp Glu Val Arg Ser Arg Ser Ser Pro Ala Gly Leu Pro Val His Ala Thr        120

CGG AGT CTG CGG GAC CTG GAG GGA GCC GGC CAA CCT GAG CAG TCG CTA AGC TTT CAG TCC        516
Arg Ser Leu Arg Asp Leu Glu Gly Ala Gly Gln Pro Glu Gln Ser Leu Ser Phe Gln Ser        140

TGG ACT TCA GCA GAG CCC GCT GCT AGA GCC TTC GGT GAG ACG CTT CGT GCC CAG CCA TGG        576
Trp Thr Ser Ala Glu Pro Ala Ala Arg Ala Phe Gly Glu Thr Leu Arg Ala Gln Pro Trp        160

TTC CTG CAG CAA ATC ATC TTT GCC GAT CCT GTC AGG CTC GAC GAC CGT CTC AAG AAC CGA        636
Phe Leu Gln Gln Ile Ile Phe Ala Asp Pro Val Arg Leu Asp Asp Arg Leu Lys Asn Arg        180

TGG CGC CCC CGT GCT TGA CCT AAG CAG GAG CAC AGC TTG TAG CTC CAG SEQ ID NO: 71          684
Trp Arg Pro Arg Ala ***                                          SEQ ID NO: 72(e)      185
```

FIG. 10

```
                                    TGA CTG GTC TCC ATC CTC TGG AGC TCC GAC GTG CTC GTT   39
CTC GGA GAC ATA AAC CCA GTT CTT GTC CTA ACC CTC CAA GGG GCA ATT GAC GTG AGC GCG           99

CTG GCG TCT AAC AGA GAA GTA CGG GGC CCT GGG CCC GGG ACT CCC AGG AAC CGG CCC CTG          159
Leu Ala Ser Asn Arg Glu Val Arg Gly Pro Gly Pro Gly Thr Pro Arg Asn Arg Pro Leu           20

CTG CCC CTG CTG CTG CTT CTG CTC TTG CTA CCG CTG CCC GCC AGC GCC TGG TAT AAG CAC          219
Leu Pro Leu Leu Leu Leu Leu Leu Leu Leu Pro Leu Pro Ala Ser Ala Trp Tyr Lys His           40

GTG GCG AGT CCC CGC TAT CAC ACA GTG GGT CGT GCC TCC GGG CTG CTC ATG GGG CTG CGC          279
Val Ala Ser Pro Arg Tyr His Thr Val Gly Arg Ala Ser Gly Leu Leu Met Gly Leu Arg           60

CGC TCG CCC TAC CAG TGG CGC CGT GCC CTG GGC GGG GCT GCT GGA CCC CTC TCC CGG CTC          339
Arg Ser Pro Tyr Gln Trp Arg Arg Ala Leu Gly Gly Ala Ala Gly Pro Leu Ser Arg Leu           80

CCA GGA CCG GTC GCC CGC GGC GCT CTC CTG CTT CCT TCC TCA GGG CAG GAG CTG TGG GAG          399
Pro Gly Pro Val Ala Arg Gly Ala Leu Leu Leu Pro Ser Ser Gly Gln Glu Leu Trp Glu          100

GTA CGA AGC AGG AGC TCA CCT GCA GGG CTT CCC GTC CAT GCA CCC TGG AGT CCG CGG GAC          459
Val Arg Ser Arg Ser Ser Pro Ala Gly Leu Pro Val His Ala Pro Trp Ser Pro Arg Asp          120

CTG GAG GGA GTC CGC CAA CCG GAG CAG TCG CTA AGC CTT CAC TCC TGG ATC TCA GAG GAG          519
Leu Glu Gly Val Arg Gln Pro Glu Gln Ser Leu Ser Leu His Ser Trp Ile Ser Glu Glu          140

CCC GCT GCT AGA GCC TTC GGA GAG ACG CTT CGT GCC CAG CCA TGG TTC CTG CAG CAA GTC          579
Pro Ala Ala Arg Ala Phe Gly Glu Thr Leu Arg Ala Gln Pro Trp Phe Leu Gln Gln Val          160

ATC TTT GCC GAT CCT GTC AGG CCC AAG AAC CGA TGG CGC CCC CAT GCT TGA CCT AGG CAG          639
Ile Phe Ala Asp Pro Val Arg Pro Lys Asn Arg Trp Arg Pro His Ala ***                      176
                                                                     SEQ ID NO: 90
GAG CAC AGC TTG AAG CTC CA  SEQ ID NO: 89                                                 659
```

FIG. 11

```
ATG GAC AAC GCC TCG TTC TCG GAG CCC TGG CCC GCC AAC GCA TCG GGC CCG GAC CCG GCG   60
Met Asp Asp Ala Ser Phe Ser Glu Pro Trp Pro Ala Asn Ala Ser Gly Pro Asp Pro Ala   20

CTG AGC TGC TCC AAC GCG TCG ACT CTG GCG CCG CTG CCG GCG CCG CTG GCG GTG GCT GTA  120
Leu Ser Cys Ser Asn Ala Ser Thr Leu Ala Pro Leu Pro Ala Pro Leu Ala Val Ala Val   40

CCA GTT GTC TAC GCG GTG ATC TGC GCC GTG GGT CTG GCG GGC AAC TCC GCC GTG CTG TAC  180
Pro Val Val Tyr Ala Val Ile Cys Ala Val Gly Leu Ala Gly Asn Ser Ala Val Leu Tyr   60

GTG TTG CTG CGG GCG CCC CGC ATG AAG ACC GTC ACC AAC CTG TTC ATC CTC AAC CTG GCC  240
Val Leu Leu Arg Ala Pro Arg Met Lys Thr Val Thr Asn Leu Phe Ile Leu Asn Leu Ala   80

ATC GCC GAC GAG CTC TTC ACG CTG GTG CTG CCC ATC AAC ATC GCC GAC TTC CTG CTG CGG  300
Ile Ala Asp Glu Leu Phe Thr Leu Val Leu Pro Ile Asn Ile Ala Asp Phe Leu Leu Arg  100

CAG TGG CCC TTC GGG GAG CTC ATG TGC AAG CTC ATC GTG GCT ATC GAC CAG TAC AAC ACC  360
Gln Trp Pro Phe Gly Glu Leu Met Cys Lys Leu Ile Val Ala Ile Asp Gln Tyr Asn Thr  120

TTC TCC AGC CTC TAC TTC CTC ACC GTC ATG AGC GCC GAC CGC TAC CTG GTG GTG TTG GCC  420
Phe Ser Ser Leu Tyr Phe Leu Thr Val Met Ser Ala Asp Arg Tyr Leu Val Val Leu Ala  140

ACT GCG GAG TCG CGC CGG GTG GCC GGC CGC ACC TAC AGC GCC GCG CGC GCG GTG AGC CTG  480
Thr Ala Glu Ser Arg Arg Val Ala Gly Arg Thr Tyr Ser Ala Ala Arg Ala Val Ser Leu  160

GCC GTG TGG GGG ATC GTC ACA CTC GTC GTG CTG CCC TTC GCA GTC TTC GCC CGG CTA GAC  540
Ala Val Trp Gly Ile Val Thr Leu Val Val Leu Pro Phe Ala Val Phe Ala Arg Leu Asp  180

GAC GAG CAG GGC CGG CGC CAG TGC GTG CTA GTC TTT CCG CAG CCC GAG GCC TTC TGG TGG  600
Asp Glu Gln Gly Arg Arg Gln Cys Val Leu Val Phe Pro Gln Pro Glu Ala Phe Trp Trp  200

CGC GCG AGC CGC CTC TAC ACG CTC GTG CTG GGC TTC GCC ATC CCC GTG TCC ACC ATC TGT  660
Arg Ala Ser Arg Leu Tyr Thr Leu Val Leu Gly Phe Ala Ile Pro Val Ser Thr Ile Cys  220

GTC CTC TAT ACC ACC CTG CTG TGC CGG CTG CAT GCC ATG CGG CTG GAC AGC CAC GCC AAG  720
Val Leu Tyr Thr Thr Leu Leu Cys Arg Leu His Ala Met Arg Leu Asp Ser His Ala Lys  240

GCC CTG GAG CGC GCC AAG AAG CGG GTG ACC TTC CTG GTG GTG GCA ATC CTG GCC GTG TGC  780
Ala Leu Glu Arg Ala Lys Lys Arg Val Thr Phe Leu Val Val Ala Ile Leu Ala Val Cys  260

CTC CTC TGC TGG ACG CCC TAC CAC CTG AGC ACC GTG GTG GCG CTC ACC ACC GAC CTC CCG  840
Leu Leu Cys Trp Thr Pro Tyr His Leu Ser Thr Val Val Ala Leu Thr Thr Asp Leu Pro  280

CAG ACG CCG CTG GTC ATC GCT ATC TCC TAC TTC ATC ACC AGC CTG AGC TAC GCC AAC AGC  900
Gln Thr Pro Leu Val Ile Ala Ile Ser Tyr Phe Ile Thr Ser Leu Ser Tyr Ala Asn Ser  300

TGC CTC AAC CCC TTC CTC TAC GCC TTC CTG GAC GCC AGC TTC CGC AGG AAC CTC CGC CAG  960
Cys Leu Asn Pro Phe Leu Tyr Ala Phe Leu Asp Ala Ser Phe Arg Arg Asn Leu Arg Gln  320

CTG ATA ACT TGC CGC GCG GCA GCC TGA  SEQ ID NO: 138(f)                            987
Leu Ile Thr Cys Arg Ala Ala Ala ***  SEQ ID NO: 129                               328
```

FIG. 13

METHOD OF SCREENING PREVENTIVES OR REMEDIES FOR OBESITY

FIELD OF THE INVENTION

The present invention relates to a method of screening drugs (appetite (eating) stimulants, antiobesity drugs, etc.) using a receptor and a polypeptide capable of specifically binding to the receptor, compounds obtainable by the screening method, and the like.

BACKGROUND ART

Important biological functions including maintenance of homeostasis in vivo, reproduction, development of individuals, metabolism, growth, control of the nervous, circulatory, immune, digestive or metabolic system, sensory adaptation, etc. are regulated by cells that receive endogenous factors such as various hormones and neurotransmitters or sensory stimulation like light or odor, via specific receptors present on cell membranes reserved for these factors or stimulation and interact with them. Many of these receptors for hormones or neurotransmitters by such functional regulation are coupled to guanine nucleotide-binding proteins (hereinafter, sometimes merely referred to as G proteins), and are characterized by developing a variety of functions through mediation of intracellular signal transduction via activation of the G proteins. In addition, these receptor proteins possess common seven transmembrane domains. Based on the foregoing, these receptors are thus collectively referred to as G protein-coupled receptors or seven transmembrane receptors. As such it is known that various hormones or neurotransmitters and their receptor proteins are present and interact with each other to play important roles for regulating the biological functions. However, it often remains unclear if there are any other unknown substances (hormones, neurotransmitters, etc.) and receptors to these substances.

In recent years, accumulated sequence information of human genome DNA or various human tissue-derived cDNA by random sequencing and rapid progress in gene analysis technology have been accelerating the investigation of human genome. Based on this, it has been clarified that there are many genes supposed to encode proteins with unknown functions. G protein-coupled receptors not only have seven transmembrane domains but many common sequences are present their nucleic acids or amino acids. Thus, they can be clearly identified to be G protein-coupled receptors in such proteins. On the other hand, these G protein-coupled receptor genes are obtained by polymerase chain reaction (hereinafter abbreviated as PCR) utilizing such a structural similarity. In these G protein-coupled receptors thus obtained so far, ligands to some receptors that are subtypes having high homology in structure to known receptors may be readily predictable but in most cases, their endogenous ligands are unpredictable so that ligands corresponding to these receptors are hardly found. For this reason, these receptors are termed orphan receptors. It is likely that unidentified endogenous ligands to such orphan receptors would take part in biological phenomena poorly analyzed because the ligands were unknown. When such ligands are associated with important physiological effects or pathologic conditions, it is expected that development of these receptor agonists or antagonists will result in breakthrough new drugs (Stadel, J. et al., TiPS, 18, 430-437, 1997; Marchese, A. et al., TiPS, 20, 370-375, 1999; Civelli, O. et al., Brain Res., 848, 63-65,1999; Howard, A. D. et al., TiPS, 22, 132-140, 2001).

Recently, some groups attempted to investigate ligands to these orphan receptors and reported isolation/structural determination of ligands which are novel physiologically active peptides. Independently Reinsheid et al. and Meunier et al. introduced cDNA encoding orphan G protein-coupled receptor LC132 or ORL1 into animal cells to express a receptor, isolated a novel peptide from swine brain or rat brain extract, which was named orphanin FQ or nociceptin with reference to its response, and determined its sequence (Reinsheid, R. K. et al., Science, 270, 792-794, 1995; Meunier, J.-C. et al., Nature, 377, 532-535, 1995). This peptide was reported to be associated with pain. Further research on the receptor in knockout mouse reveals that the peptide takes part in memory (Manabe, T. et al., Nature, 394, 577-581, 1998).

Subsequently, novel peptides such as PrRP (prolactin releasing peptide), orexin, apelin, ghrelin and GALP (galanin-like peptide), etc. were isolated as ligands to orphan G protein-coupled receptors (Hinuma, S. et al., Nature, 393, 272-276, 1998; Sakurai, T. et al., Cell, 92, 573-585, 1998; Tatemoto, K. et al., Biohem. Biophys. Res. Commun., 251, 471-476, 1998; Kojima, M. et al., Nature, 402, 656-660, 1999; Ohtaki, T. et al., J. Biol. Chem., 274, 37041-37045, 1999). On the other hand, some receptors to physiologically active peptides, which were hitherto unknown, were clarified. It was revealed that a receptor to motilin associated with contraction of intestinal tracts was GPR38 (Feighner, S. D. et al., Science, 284, 2184-2188, 1999). Furthermore, SLC-1 was identified to be a receptor to MCH (Chambers, J. et al., Nature, 400, 261-265, 1999; Saito, Y. et al., Nature, 400, 265-269, 1999; Shimomura, Y. et al., Biochem. Biophys. Res. Commun., 261, 622-626, 1999; Lembo, P. M. C. et al., Nature Cell Biol., 1, 267-271, 1999; Bachner, D. et al., FEBS Lett., 457, 522-524, 1999). Also, GPR14 (SENR) was reported to be a receptor to urotensin II (Ames, R. S. et al., Nature, 401, 282-286, 1999; Mori, M. et al., Biochem. Biophys. Res. Commun., 265, 123-129, 1999; Nothacker, H. P. et al., Nature Cell Biol., 1, 383-385, 1999, Liu, Q. et al., Biochem. Biophys. Res. Commun., 266, 174-178, 1999). Moreover, receptors for neuromedin U and neuropeptide FF; which are neuropeptides, have recently been revealed. In addition to these peptides, low molecular physiologically active lipids or nucleic acid derivatives such as cysteinyl leukotrienes, sphingosine-1-phosphate, lysophosphatidic acid, sphingosylphosphprylcholine, UDP-glucose, etc. have been identified to be ligands to orphan receptors (Howard, A. D. et al., TiPS, 22, 132-140, 2001). It was shown that MCH took part in obesity since its knockout mice showed the reduced body weight and lean phenotype (Shimada, M. et al., Nature, 396, 670-674, 1998), and because its receptor was revealed, it became possible to explore a receptor antagonist likely to be an antiobesity agent. It is further reported that urotensin II shows a potent action on the cardiocirculatory system, since it induces heart ischemia by intravenous injection to monkey (Ames, R. S. et al., Nature, 401, 282-286, 1999).

As described above, orphan receptors and ligands thereto often take part in a new physiological activity, and it is expected that their clarification will lead to development of new drugs. However, it is known that research on ligands to orphan receptors is accompanied by many difficulties. For example, it is generally unknown what secondary signal transduction system will take place after orphan receptors expressed on cells responded to ligands, and various response system should be examined. Moreover, tissues where ligands are present are not readily predictable so that various tissue extracts should be prepared. Furthermore, since an amount of ligand required to stimulate its receptor is sufficient even in an extremely low concentration when the ligand is a peptide, the amount of such a ligand present in vivo is a trace amount in many cases. In addition, a peptide is digested by peptidase to lose its activity, or undergoes non-specific adsorption so that its recovery becomes poor during purification. Thus, it is normally extremely difficult to extract such a ligand from the living body and isolate an amount of the ligand necessary for determination of its structure. The presence of many orphan receptors was unraveled, but only a very small part of ligands to these receptors were discovered so far due to the foregoing problems.

One of the reported orphan G protein-coupled receptors is GPR7 (SEQ ID NO:129, O'Dowd, B. F. et al., Genomics, 28, 84-91, 1995). GPR7 has a low homology to somatostatin receptor (SSTR3) and opioid receptors (δ, κ and μ), but was yet unknown what its ligand was. Furthermore, GPR7 was found to have a homology of about 64% to GPR8 (SEQ ID NO:4, O'Dowd, B. F. et al., Genomics, 28, 84-91, 1995) in an amino acid level.

It was thus desired to find an endogenous ligand to GPR7 and make direct use of the ligand or make use of a drug screening system using the ligand (preferably in combination with GPR7) to develop pharmaceuticals with quite a new mechanism unknown so far.

DISCLOSURE OF THE INVENTION

The present inventors have made extensive studies to solve the foregoing problems, and as a result, have discovered that an endogenous ligand, which was found in the extract from porcine hypothalamus using as an indicator its capability of specifically binding to GPR8 having a homology to GPR7, is an endogenous ligand to GPR7 as well. The inventors have further found that the ligand has an appetite (eating) stimulating activity, GPR7 agonist and GPR7 antagonist can be used as an appetite (eating) stimulant and a preventive/therapeutic agent for obesity (antiobesity drug/agent), respectively. Based on these findings, the inventors have made extensive investigations and come to attain the present invention.

That is, the present invention relates to the following features:

[1] A method of screening a compound or its salt that alters the binding property between (1) a protein or its salt containing the same or substantially the same amino acid sequence as the amino acid sequence represented by SEQ ID NO:129 and (2) a polypeptide capable of specifically binding to the protein, or its amide or ester, or a salt thereof, which comprises using (1) the protein or its salt and (2) the polypeptide or its amide or ester, or a salt thereof;

[2] The method of screening according to [1], wherein the polypeptide is a polypeptide containing the same or substantially the same amino acid sequence as the amino acid sequence represented by SEQ ID NO:16;

[3] The method of screening according to [1], wherein the polypeptide is a polypeptide containing the amino acid sequence represented by SEQ ID NO:16 or SEQ ID NO:17;

[4] A kit for screening a compound or its salt that alters the binding property between (1) a protein or its salt containing the same or substantially the same amino acid sequence as the amino acid sequence represented by SEQ ID NO:129 and (2) a polypeptide capable of specifically binding to the protein, or its amide or ester, or a salt thereof, comprising (1) the protein or its salt and (2) the polypeptide or its amide or ester, or a salt thereof;

[5] A compound or its salt that alters the binding property between (1) a protein or its salt containing the same or substantially the same amino acid sequence as the amino acid sequence represented by SEQ ID NO:129 and (2) a polypeptide capable of specifically binding to the protein, or its amide or ester, or a salt thereof, which is obtainable using the method of screening according to [1] or the kit for screening according to [4];

[6] A pharmaceutical composition comprising the compound or its salt according to [5];

[7] The compound according to [5], which is a compound that inhibits the activity of the protein or its salt containing the same or substantially the same amino acid sequence as the amino acid sequence represented by SEQ ID NO:129.

[8] An antiobesity agent, which is obtainable using the method of screening according to [1] or the kit for screening according to [4];

[9] An antiobesity agent comprising the compound or its salt according to [7];

[10] A method of preventing/treating obesity, which comprises administering to a mammal an effective dose of the compound or its salt according to [7];

[11] Use of the compound or its salt according to [7] for manufacturing an antiobesity agent; and so on.

The present invention further provides the following features.

[12] The method of screening according to [2], wherein substantially the same amino acid sequence as the amino acid sequence represented by SEQ ID NO:16 is an amino acid sequence represented by SEQ ID NO:6, SEQ ID NO:17, SEQ ID NO:20, SEQ ID NO:21, SEQ ID NO:22, SEQ ID NO:23, SEQ ID NO:24, SEQ ID NO:25, SEQ ID NO:56, SEQ ID NO:57, SEQ ID NO:73, SEQ ID NO:74, SEQ ID NO:91, SEQ ID NO:92, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:11, SEQ ID NO:112, SEQ ID NO:113 or SEQ ID NO:135;

[13] The method of screening according to [1], wherein the polypeptide is a polypeptide containing the amino acid sequence represented by SEQ ID NO:15, SEQ ID NO:42, SEQ ID NO:55, SEQ ID NO:72 or SEQ ID NO:90;

[14] A method of screening a compound or its salt that inhibits the activity of a protein or its salt containing the same or substantially the same amino acid sequence as the amino acid sequence represented by SEQ ID NO:129, which comprises using (1) the protein or its salt and (2) a polypeptide capable of specifically binding to the protein, or its amide or ester, or a salt thereof;

[15] A method of screening a compound or its salt that promotes the activity of a protein or its salt containing the same or substantially the same amino acid sequence as the amino acid sequence represented by SEQ ID NO:129, which comprises using (1) the protein or its salt and (2) a polypeptide capable of specifically binding to the protein, or its amide or ester, or a salt thereof;

[16] The method of screening according to [1], which comprises using the protein or its salt containing the same or substantially the same amino acid sequence as the amino acid sequence represented by SEQ ID NO:129, a partial peptide of the protein, or its amide or ester, or a salt thereof;

[17] An antiobesity agent, comprising a compound or its salt that reduces the expression level of a protein or its salt containing the same or substantially the same amino acid sequence as the amino acid sequence represented by SEQ ID NO:129;

[18] A preventive/therapeutic agent for anorexia nervosa or an appetite (eating) stimulant, comprising a protein, its partial peptide or a salt thereof, containing the same or substantially the same amino acid sequence as the amino acid sequence represented by SEQ ID NO:129;

[19] A preventive/therapeutic agent for anorexia nervosa or an appetite (eating) stimulant, comprising a polynucleotide containing a polynucleotide encoding a protein or its partial peptide containing the same or substantially the same amino acid sequence as the amino acid sequence represented by SEQ ID NO:129;

[20] A diagnostic product for obesity, comprising a polynucleotide containing a polynucleotide encoding a protein or its partial peptide containing the same or substantially the same amino acid sequence as the amino acid sequence represented by SEQ ID NO:129;

[21] An antiobesity agent, comprising an antibody to a protein, its partial peptide or a salt thereof, containing the same or substantially the same amino acid sequence as the amino acid sequence represented by SEQ ID NO:129;

[22] A diagnostic product for obesity, comprising an antibody to a protein, its partial peptide or a salt thereof, containing the same or substantially the same amino acid sequence as the amino acid sequence represented by SEQ ID NO:129;

[23] An antiobesity agent, comprising an antisense polynucleotide comprising a complementary base sequence or a part thereof to a polynucleotide containing a polynucleotide encoding a protein or its partial peptide containing the same or substantially the same amino acid sequence as the amino acid sequence represented by SEQ ID NO:129;

[24] A diagnostic product for obesity, comprising an antisense polynucleotide comprising a complementary base sequence or a part thereof to a polynucleotide containing a polynucieotide encoding a protein or its partial peptide containing the same or substantially the same amino acid sequence as the amino acid sequence represented by SEQ ID NO:129; and so on.

BRIEF DESCRIPTION OF THE DRAWINGS

FIGS. 1A & 1B shows the entire base sequence of human GPR8 receptor protein cDNA (SEQ ID NO: 136) and the whole amino acid sequence (SEQ ID NO: 137) of human GPR8 receptor protein translated therefrom.

FIG. 8 shows the entire base sequence of human homologue precursor protein cDNA (SEQ ID NO: 41) of GPR8 ligand peptide and the entire amino acid (SEQ ID NO: 42) sequence of human homologue precursor receptor protein of GPR8 ligand peptide translated therefrom, wherein a putative GPR8 ligand human homologue peptide composed of 23 residues is enclosed in a box.

FIG. 9 shows the entire base sequence of porcine homologue precursor protein cDNA (SEQ ID NO: 54) of GPR8 ligand peptide and the entire amino acid sequence (SEQ ID NO: 55) of a porcine homologue precursor receptor protein of GPR8 ligand peptide translated therefrom, wherein a putative GPR8 ligand porcine homologue peptide composed of 23 residues is enclosed in a box.

FIG. 10 shows the entire base sequence of rat homologue precursor protein cDNA (SEQ ID NO: 71) of GPR8 ligand peptide and the entire amino acid sequence (SEQ ID NO: 72) of rat homologue precursor receptor protein of GPR8 ligand peptide translated therefrom, wherein a putative GPR8 ligand rat homologue peptide composed of 23 residues is enclosed in a box.

FIG. 11 shows the entire base sequence of mouse homologue precursor protein cDNA (SEQ ID NO: 89) of GPR8 ligand peptide and the entire amino acid sequence (SEQ ID NO: 90) of mouse homologue precursor receptor protein of GPR8 ligand peptide translated therefrom, wherein a putative GPR8 ligand mouse homologue peptide composed of 23 residues is enclosed in a box.

FIG. 13 shows the entire base sequence of human GPR7 cDNA (SEQ ID NO: 138) and the whole amino acid sequence (SEQ ID NO: 129) of human GPR7 translated therefrom.

BEST MODE FOR CARRYING OUT THE INVENTION

Figure 2:
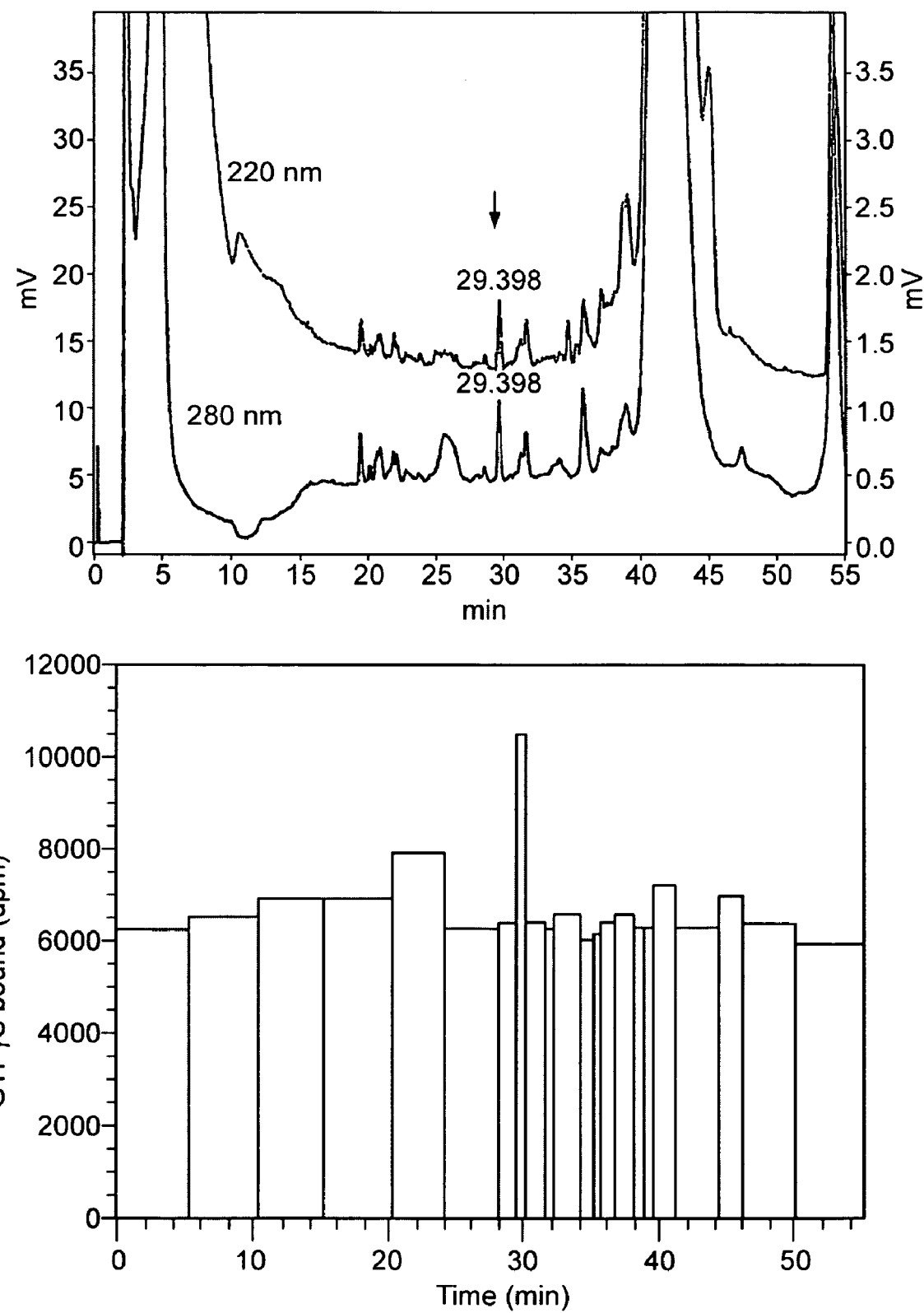
FIG. 2 shows UV absorption of GPR8 ligand in the final stage purification by HPLC using Wakosil-II 3C18HG column and the GTPγ S activity of each peak. The activity was recovered in the peak shown by arrow.

The polypeptide capable of specifically binding to a protein or its salt containing the same or substantially the same amino acid sequence as the amino acid sequence represented by SEQ ID NO:129 is sometime referred to as the polypeptide of the present invention.

Examples of the polypeptide of the present invention include a polypeptide, etc., having a dissociation constant of 1 nM or less, preferably not greater than 200 pM, more preferably not greater than 100 pM, much more preferably not greater than 80 pM, and most preferably not greater than 50 pM, in binding to a polypeptide capable of binding to a protein or its salt containing the same or substantially the same amino acid sequence as the amino acid sequence represented by SEQ ID NO:129.

The polypeptide having the same or substantially the same amino acid sequence as the amino acid sequence shown by SEQ ID NO:16, which is an example of the polypeptide of the present invention, may be any polypeptide derived from any cells of human and non-human warm-blooded animals (e.g., guinea pig, rat, mouse, chicken, rabbit, swine, sheep, bovine, monkey, etc.) (for example, retina cell, liver cell, splenocyte, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., or the corresponding precursor cells, stem cells, cancer cells, etc.), or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; or may be any polypeptide derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); and the polypeptide may also be a synthetic polypeptide.

Substantially the same amino acid sequence as the amino acid sequence represented by SEQ ID NO:16 includes an amino acid sequence having at least about 90% homology, preferably at least about 95% homology, and more preferably at least about 98% homology, to the amino acid sequence represented by SEQ ID NO:16.

Specifically, substantially the same amino acid sequence as the amino acid sequence represented by SEQ ID NO:16 includes, in addition to the amino acid sequences described above:

(i) the amino acid sequence represented by SEQ ID NO:16, of which 1 to 5 (preferably 1 to 3, more preferably 1 or 2, and most preferably 1) amino acids are deleted;

(ii) the amino acid sequence represented by SEQ ID NO:16, to which 1 to 5 (preferably 1 to 3, more preferably 1 or 2, and most preferably 1) amino acids are added;

(iii) the amino acid sequence represented by SEQ ID NO:16, in which 1 to 5 (preferably 1 to 3, more preferably 1 or 2, and most preferably 1) amino acids are inserted;

(iv) the amino acid sequence represented by SEQ ID NO:16, in which 1 to 5 (preferably 1 to 3, more preferably 1 or 2, and most preferably 1) amino acids are substituted with other amino acids; and, (v) a combination of the amino acid sequences (i) through (iv) described above, etc.

Examples of the polypeptide which has substantially the same amino acid sequence as the amino acid sequence shown by SEQ ID NO:16 include a polypeptide containing substantially the same amino acid sequence as the amino acid sequence shown by SEQ ID NO:16 and having an activity substantially equivalent to that of the amino acid sequence represented by SEQ ID NO:16, and the like.

The substantially equivalent activity refers to, e.g., activities possessed by the polypeptide of the present invention, for example, the preventive/therapeutic activities later described, the binding activity to receptors, the cell-stimulating activity on receptor-expressed cells (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.), and the like.

The term "substantially equivalent activity" is used to mean that these activities are equivalent in nature (for example, biochemically or pharmacologically).

Specific examples of substantially the same amino acid sequence as the amino acid sequence represented by SEQ ID NO:16 are amino acid sequences represented by SEQ ID NO:6, SEQ ID NO:17, SEQ ID NO:20, SEQ ID NO:21, SEQ ID NO:22, SEQ ID NO:23, SEQ ID NO:24, SEQ ID NO:25, SEQ ID NO:56, SEQ ID NO:57, SEQ ID NO:73, SEQ ID NO:74, SEQ ID NO:91, SEQ ID NO:92, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113 or SEQ ID NO:135, and the like.

Specific examples of the polypeptide of the present invention are polypeptides capable of specifically binding to GPR7, including a polypeptide having the amino acid sequence represented by SEQ ID NO:16, a polypeptide having the amino acid sequence represented by SEQ ID NO:6, a polypeptide having the amino acid sequence represented by SEQ ID NO:17, a polypeptide having the amino acid sequence represented by SEQ ID NO:20, a polypeptide having the amino acid sequence represented by SEQ ID NO:21, a polypeptide having the amino acid sequence represented by SEQ ID NO:22, a polypeptide having the amino acid sequence represented by SEQ ID NO:23, a polypeptide having the amino acid sequence represented by SEQ ID NO:24, a polypeptide having the amino acid sequence represented by SEQ ID NO:25, a polypeptide having the amino acid sequence represented by SEQ ID NO:56, a polypeptide having the amino acid sequence represented by SEQ ID NO:57, a polypeptide having the amino acid sequence represented by SEQ ID NO:73, a polypeptide having the amino acid sequence represented by SEQ ID NO:74, a polypeptide having the amino acid sequence represented by SEQ ID NO:91, a polypeptide having the amino acid sequence represented by SEQ ID NO:92, a polypeptide having the amino acid sequence represented by SEQ ID NO:95, a polypeptide having the amino acid sequence represented by SEQ ID NO:96, a polypeptide having the amino acid sequence represented by SEQ ID NO:97, a polypeptide having the amino acid sequence represented by SEQ ID NO:98, a polypeptide having the amino acid sequence represented by SEQ ID NO:99, a polypeptide having the amino acid sequence represented by SEQ ID NO:100, a polypeptide having the amino acid sequence represented by SEQ ID NO:101, a polypeptide having the amino acid sequence represented by SEQ ID NO:102, a polypeptide having the amino acid sequence represented by SEQ ID NO:103, a polypeptide having the amino acid sequence represented by SEQ ID NO:104, a polypeptide having the amino acid sequence represented by SEQ ID NO:105, a polypeptide having the amino acid sequence represented by SEQ ID NO:106, a polypeptide having the amino acid sequence represented by SEQ ID NO:107, a polypeptide having the amino acid sequence represented by SEQ ID NO:108, a polypeptide having the amino acid sequence represented by SEQ ID NO:109, a polypeptide having the amino acid sequence represented by SEQ ID NO:110, a polypeptide having the amino acid sequence represented by SEQ ID NO:111, a polypeptide having the amino acid sequence represented by SEQ ID NO:112, a polypeptide having the amino acid sequence represented by SEQ ID NO:113, and a polypeptide having the amino acid sequence represented by SEQ ID NO:135; and the like.

The polypeptide of the present invention is used to mean that the polypeptide not only includes polypeptides having the activity of binding to a protein or its salt containing the same or substantially the same amino acid sequence as the amino acid sequence represented by SEQ ID NO:129, the cell-stimulating activity on cells where the protein is expressed (e.g., the activity that promotes arachidonic acid release, acetylcholine release, intracellular $Ca^{2+}$ release, intracellular cAMP production, suppression of intracellular cAMP production, intracellular cGMP production, inositol phosphate production, change in cell membrane potential, phosphorylation of intracellular proteins, activation of c-fos, pH reduction, GTPγ S binding activity, etc.), and the like, but also includes precursor polypeptides of the polypeptides having the binding activity or cell-stimulating activity above.

Specific examples of the precursor polypeptides of the polypeptides having such a binding activity or cell-stimulating activity are polypeptides characterized by containing the same or substantially the same amino acid sequence as the amino acid sequence represented by SEQ ID NO:15, etc.

More specifically, substantially the same amino acid sequence as the amino acid sequence represented by SEQ ID NO:15 refers to amino acid sequences having at least about 80% homology, preferably at least about 90% homology, and more preferably at least about 95% homology, to the amino acid sequence represented by SEQ ID NO:15, etc.

In particular, substantially the same amino acid sequences as the amino acid sequence represented by SEQ ID NO:15 include, in addition to the amino acid sequences described above:

(i) the amino acid sequence represented by SEQ ID NO:15, of which 1 to 15 (preferably 1 to 10, more preferably 1 or 5, and most preferably 1 to 3) amino acids are deleted;

(ii) the amino acid sequence represented by SEQ ID NO:15, to which 1 to 100 (preferably 1 to 50, more preferably 1 or 5, and most preferably 1 to 3) amino acids are added;

(iii) the amino acid sequence represented by SEQ ID NO:15, in which 1 to 15 (preferably 1 to 10, more preferably 1 or 5, and most preferably 1 to 3) amino acids are inserted;

(iv) the amino acid sequence represented by SEQ ID NO:15, in which 1 to 15 (preferably 1 to 10, more preferably 1 or 5, and most preferably 1 to 3) amino acids are substituted with other amino acids; and, (v) a combination of the amino acid sequences (i) through (iv) described above, etc.

Specific examples of substantially the same amino acid sequence as the amino acid sequence represented by SEQ ID NO:15 include amino acid sequences represented by SEQ ID NO:42, SEQ ID NO:55, SEQ ID NO:72 and SEQ ID NO:90.

Specific examples of the precursor polypeptide described above are a polypeptide having the amino acid sequence represented by SEQ ID NO:15, a polypeptide having the amino acid sequence represented by SEQ ID NO:42, a polypeptide having the amino acid sequence represented by SEQ ID NO:55, a polypeptide having the amino acid sequence represented by SEQ ID NO:72 or a polypeptide having the amino acid sequence represented by SEQ ID NO:90, and the like.

The protein of the present invention having the same or substantially the same amino acid sequence as the amino acid sequence represented by SEQ ID NO:129 (hereinafter sometimes referred to as the receptor of the present invention) may be any protein derived from any cells of human and non-human warm-blooded animals (e.g., guinea pig, rat, mouse, chicken, rabbit, swine, sheep, bovine, monkey, etc.) (for example, retina cell, liver cell, splenocyte, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., or the corresponding precursor cells, stem cells, cancer cells, etc.), or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; proteins derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); the protein may also be a synthetic protein.

The amino acid sequence, which is substantially the same as the amino acid sequence represented by SEQ ID NO:129, includes amino acid sequences having at least about 70% homology, preferably at least about 80% homology, and more preferably at least about 90% homology, to the amino acid sequence represented by SEQ ID NO:129, etc.

In particular, the amino acid sequences substantially the same as the amino acid sequence represented by SEQ ID NO:129 include, in addition to the amino acid sequences described above:

(i) the amino acid sequence represented by SEQ ID NO:129, of which 1 to 15 (preferably 1 to 10, more preferably 1 or 5, and most preferably 1 to 3) amino acids are deleted;

(ii) the amino acid sequence represented by SEQ ID NO:129, to which 1 to 15 (preferably 1 to 10, more preferably 1 or 5, and most preferably 1 to 3) amino acids are added;

(iii) the amino acid sequence represented by SEQ ID NO:129, in which 1 to 15 (preferably 1 to 10, more preferably 1 or 5, and most preferably 1 to 3) amino acids are inserted;

(iv) the amino acid sequence represented by SEQ ID NO:129, in which 1 to 15 (preferably 1 to 10, more preferably 1 or 5, and most preferably 1 to 3) amino acids are substituted with other amino acids; and, (v) a combination of the amino acid sequences (i) through (iv) described above, etc.

Any partial peptide can be used as the partial peptide of the receptor of the present invention (hereinafter sometimes referred to as the partial peptide of the present invention), as long as it is a partial peptide available for the method of screening drugs, etc. later described. Preferably, there may be employed partial peptides capable of binding to the polypeptide of the present invention, partial peptides containing an amino acid sequence corresponding to the extracellular region, and the like.

The polypeptides, receptors or partial peptides of the present invention are represented in accordance with the conventional way of describing peptides, that is, the N-terminus (amino terminus) at the left hand and the C-terminus (carboxyl terminus) at the right hand.

In the polypeptides of the present invention, the C-terminus is usually in the form of a carboxyl group (—COOH) or a carboxylate (—COO$^-$) but the C-terminus may be in the form of an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; an aralkyl having 7 to 14 carbon atoms such as a phenyl-$C_{1-2}$ alkyl group, e.g., benzyl, phenethyl, etc.; α-naphthyl-$C_{1-2}$ alkyl-group such as α-naphthylmethyl, etc.; and the like. In addition, pivaloyloxymethyl or the like, which is used widely as an ester for oral administration may also be used.

Where the polypeptides, receptors or partial peptides of the present invention contain a carboxyl group (or a carboxylate) at a position other than the C-terminus, it may be amidated or esterified and such an amide or ester is also included within the polypeptide of the present invention. In this case, the ester group may be the C-terminal esters, etc. described above.

The polypeptides, receptors or partial peptides of the present invention further include those wherein the amino group at the N-terminal amino acid residues (e.g., methionine residue) is protected with a protecting group (e.g., a $C_{1-6}$ acyl group, e.g., a $C_{1-6}$ alkanoyl group such as formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ acyl group, e.g., a $C_{1-6}$ alkanoyl group such as formyl group, acetyl group, etc.), or conjugated proteins such as so-called glycoproteins having sugar chains, and the like.

As salts of the polypeptides, receptors or partial peptides of the present invention, there are salts with physiologically acceptable acids (e.g., inorganic acids, organic acids) or bases (e.g., alkali metal bases), etc., with patticular preference in the form of physiologically acceptable acid addition salts. Examples of such salts are salts with inorganic acids (e.g., hydrochloric acid, phosphoric acid, hydrobronic acid, and sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptides, receptors or partial peptides of the present invention may be manufactured by a publicly known method used to purify polypeptides from the cells or tissues of human or non-human warm-blooded animal described above, or may also be manufactured by culturing a transformant containing a DNA encoding the polypeptide, as will be later described. Furthermore, the polypeptides, receptors or partial peptides may also be manufactured by a modification of protein synthesis, which will be described hereinafter.

Where the polypeptides, receptors or partial peptides are manufactured from the tissues or cells of human or non-human warm-blooded animal, the tissues or cells of human or non-human warm-blooded animal are homogenized and extracted with an acid or the like, and the extract is purified and isolated by a combination of chromatography techniques such as reversed phase chromatography, ion exchange chromatography, or the like.

To synthesize the polypeptides, receptors or partial peptides of the present invention or salts thereof, or amides thereof, commercially available resins that are used for polypeptide synthesis may normally be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids, in which α-amino groups and functional groups on the side chains are appropriately protected, are condensed on the resin in the order of the sequences of the objective polypeptide according to various condensation methods publicly known in the art. At the end of the reaction, the polypeptide is excised from the resin and at the same time, the protecting groups are removed. Then, intramolecular disulfide bond-forming reaction is performed in a highly diluted solution to obtain the objective polypeptides, receptors or partial peptides, or amides thereof.

For condensation of the protected amino acids described above, a variety of activation reagents for polypeptide synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for polypeptide condensation reactions. Examples of such solvents are acid amides such as N,N-diniethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide bond-forming reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group for the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the polypeptides, receptors or partial peptides of the present invention, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group of the peptide chain has been eliminated from the polypeptide and a polypeptide in which only the protecting group of the C-terminal carboxyl group has been eliminated are prepared. The two polypeptides are condensed in a mixture of the solvents described above. The details of the condensation reaction are the same as described above. After the protected polypeptide obtained by the condensation is purified, all the protecting groups are eliminated by the method described above to obtain the desired crude polypeptide. This crude polypeptide is purified by various known purification means. Lyophilization of the major fraction gives the amide of the desired polypeptides, receptors or partial peptides thereof.

To prepare the esterified polypeptides, receptors or partial peptides thereof, for example, the α-carboxyl group of the carboxy terminal amino acid is condensed with a desired alcohol to prepare the amino acid ester, which is followed by procedure similar to the preparation of the amidated protein above to give the desired esterified polypeptides, receptors or partial peptides thereof.

The polypeptides, receptors or partial peptides of the present invention can be manufactured by publicly known methods for peptide synthesis; or the partial peptides of the receptors may be manufactured by cleaving the receptors with an appropriate peptidase. For the peptide synthesis, for example, either solid phase synthesis or liquid phase synthesis may be used. That is, the partial peptides or amino acids that can construct the polypeptides, receptors or partial peptides of the present invention are condensed with the remaining part. Where the product contains protecting groups, these protecting groups are removed to give the desired peptide. Publicly known methods for condensation and elimination of the protecting groups are described in i)-v) below.

i) M. Bodanszky & M. A. Ondetti: Peptide Synthesis, Interscience Publishers, New York (1966)

ii) Schroeder & Luebke: The Peptide, Academic Press, New York (1965)

iii) Nobuo Izumiya, et al.: *Peptide Gosei-no-Kiso to Jikken* (Basics and experiments of peptide synthesis), published by Maruzen Co. (1975)

iv) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

v) Haruaki. Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography, recrystallization, etc. to give the polypeptides, receptors or partial peptides of the present invention. When the polypeptides, receptors or partial peptides of the present invention obtained by the above methods is in a free form, they may be converted into appropriate salts by publicly known methods or modifications thereof; when they are obtained in a salt form, they may be converted into their free form or in the form of different salts by publicly known methods or modifications thereof.

For the DNA encoding the polypeptides, receptors or partial peptides of the present invention, any DNA can be used so long as it contains the base sequence encoding the polypeptides, receptors or partial peptides of the present invention described above. The DNA may be any of genomic DNA, genomic DNA library, cDNA derived from the cells/tissues described above, cDNA library derived from the cells/tissues described above, and synthetic DNA.

The vector to be used for the library may be any of bacteriophage, plasmid, cosmid, phagemid, and the like. In addition, the DNA can be directly amplified by reverse transcriptase polymerase chain reaction (hereinafter abbreviated as RT-PCR) with total RNA or mRNA fraction prepared from the above-described cells or tissues.

The DNA encoding the polypeptide of the present invention may be any DNA, so long as it is, for example, (1) a DNA containing the base sequence represented by SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:75, SEQ ID NO:76, SEQ ID NO:93, SEQ ID NO:94, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124 or SEQ ID NO:125, (ii) a DNA having a base sequence hybridizable under high stringent conditions to the base sequence represented by SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:75, SEQ ID NO:76, SEQ ID NO:93, SEQ ID NO:94, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124 or SEQ ID NO:125 and encoding a polypeptide which has the activity substantially equivalent to that of the polypeptide of the present invention, (iii) a DNA containing the base sequence represented by SEQ ID NO:14, SEQ ID NO:41, SEQ ID NO:54, SEQ ID NO:71 or SEQ ID NO:89, or (iv) a DNA containing a base sequence hybridizable to the base sequence represented by SEQ ID NO:14, SEQ ID NO:41, SEQ ID NO:54, SEQ ID NO:71 or SEQ ID NO:89 under high stringent conditions; etc.

Specific examples of the DNA that is hybridizable under high stringent conditions to the base sequence represented by SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:75, SEQ ID NO:76, SEQ ID NO:93, SEQ ID NO:94, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124 or SEQ ID NO:125, or to the base sequence represented by SEQ ID NO:14, SEQ ID NO:41, SEQ ID NO:54, SEQ ID NO:71 or SEQ ID NO:89 are DNAs containing base sequences having at least about 70% homology, preferably at least about 80% homology, more preferably at least about 90% homology and most preferably at least about 95% homology, to the base sequence represented by SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:75, SEQ ID NO:76, SEQ ID NO:93, SEQ ID NO:94, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124 or SEQ ID NO:125, or by SEQ ID NO:14, SEQ ID NO:41, SEQ ID NO:54, SEQ ID NO:71 or SEQ ID NO:89; and the like.

The hybridization can be carried out by publicly known methods or by modifications thereof, for example, according to the method described in Molecular Cloning, 2nd Ed. (J. Sambrook et al., Cold Spring Harbor Lab. Press, 1989), etc. A commercially available library may also be used according to the instructions of the attached manufacturer's protocol. The hybridization can be carried out preferably under high stringent conditions.

The high stringent conditions used herein are, for example, those in a sodium concentration at approximately 19 to 40 mM, preferably approximately 19 to 20 mM at a temperature of approximately 50 to 70° C., preferably approximately 60 to 65° C. In particular, hybridization conditions in a sodium concentration at about 19 mM at a temperature of about 65° C. are most preferred.

More specifically;

(i) a DNA containing the base sequence represented by SEQ ID NO:18 or the like is used as the DNA encoding the polypeptide containing the amino acid sequence represented by SEQ ID NO:16;

(ii) a DNA containing the base sequence represented by SEQ ID NO:19 or the like is used as the DNA encoding the polypeptide containing the amino acid sequence represented by SEQ ID NO:17;

(iii) a DNA containing the base sequence represented by SEQ ID NO:26 or the like is used as the DNA encoding the polypeptide containing the amino acid sequence represented by SEQ ID NO:20;

(iv) a DNA containing the base sequence represented by SEQ ID NO:27 or the like is used as the DNA encoding the polypeptide containing the amino acid sequence represented by SEQ ID NO:21;

(v) a DNA containing the base sequence represented by SEQ ID NO:28 or the like is used as the DNA encoding the polypeptide containing the amino acid sequence represented by SEQ ID NO:22;

(vi) a DNA containing the base sequence represented by SEQ ID NO:29 or the like is used as the DNA encoding the polypeptide containing the amino acid sequence represented by SEQ ID NO:23;

(vii) a DNA containing the base sequence represented by SEQ ID NO:30 or the like is used as the DNA encoding the polypeptide containing the amino acid sequence represented by SEQ ID NO:24;

(viii) a DNA containing the base sequence represented by SEQ ID NO:31 or the like is used as the DNA encoding the polypeptide containing the amino acid sequence represented by SEQ ID NO:25;

(ix) a DNA containing the base sequence represented by SEQ ID NO:58 or the like is used as the DNA encoding the polypeptide containing the amino acid sequence represented by SEQ ID NO:56;

(x) a DNA containing the base sequence represented by SEQ ID NO:59 or the like is used as the DNA encoding the polypeptide containing the amino acid sequence represented by SEQ ID NO:57;

(xi) a DNA containing the base sequence represented by SEQ ID NO:75 or the like is used as the DNA encoding the polypeptide containing the amino acid sequence represented by SEQ ID NO:73;

(xii) a DNA containing the base sequence represented by SEQ ID NO:76 or the like is used as the DNA encoding the polypeptide containing the amino acid sequence represented by SEQ ID NO:74;

(xiii) a DNA containing the base sequence represented by SEQ ID NO:93 or the like is used as the DNA encoding the polypeptide containing the amino acid sequence represented by SEQ ID NO:91;

(xiv) a DNA containing the base sequence represented by SEQ ID NO:94 or the like is used as the DNA encoding the polypeptide containing the amino acid sequence represented by SEQ ID NO:92;

(xv) a DNA containing the base sequence represented by SEQ ID NO:18 or the like is used as the DNA encoding the polypeptide containing the amino acid sequence represented by SEQ ID NO:95;

(xvi) a DNA containing the base sequence represented by SEQ ID NO:114 or the like is used as the DNA encoding the polypeptide containing the amino acid sequence represented by SEQ ID NO:96;

(xvii) a DNA containing the base sequence represented by SEQ ID NO:115 or the like is used as the DNA encoding the polypeptide containing the amino acid sequence represented by SEQ ID NO:97;

(xviii) a DNA containing the base sequence represented by SEQ ID NO:116 or the like is used as the DNA encoding the polypeptide containing the amino acid sequence represented by SEQ ID NO:98;

(xix) a DNA containing the base sequence represented by SEQ ID NO:117 or the like is used as the DNA encoding the polypeptide containing the amino acid sequence represented by SEQ ID NO:99;

(xx) a DNA containing the base sequence represented by SEQ ID NO:118 or the like is used as the DNA encoding the polypeptide containing the amino acid sequence represented by SEQ ID NO:100;

(xxi) a DNA containing the base sequence represented by SEQ ID NO:119 or the like is used as the DNA encoding the polypeptide containing the amino acid sequence represented by SEQ ID NO:101;

(xxii) a DNA containing the base sequence represented by SEQ ID NO:120 or the like is used as the DNA encoding the polypeptide containing the amino acid sequence represented by SEQ ID NO:102;

(xxiii) a DNA containing the base sequence represented by SEQ ID NO:58 or the like is used as the DNA encoding the polypeptide containing the amino acid sequence represented by SEQ ID NO:103;

(xxiv) a DNA containing the base sequence represented by SEQ ID NO:75 or the like is used as the DNA encoding the polypeptide containing the amino acid sequence represented by SEQ ID NO:104;

(xxv) a DNA containing the base sequence represented by SEQ ID NO:18 or the like is used as the DNA encoding the polypeptide containing the amino acid sequence represented by SEQ ID NO:105;

(xxvi) a DNA containing the base sequence represented by SEQ ID NO:18 or the like is used as the DNA encoding the polypeptide containing the amino acid sequence represented by SEQ ID NO:106;

(xxvii) a DNA containing the base sequence represented by SEQ ID NO:121 or the like is used as the DNA encoding the polypeptide containing the amino acid sequence represented by SEQ ID NO:107;

(xxviii) a DNA containing the base sequence represented by SEQ ID NO:122 or the like is used as the DNA encoding the polypeptide containing the amino acid sequence represented by SEQ ID NO:108;

(xxix) a DNA containing the base sequence represented by SEQ ID NO:123 or the like is used as the DNA encoding the polypeptide containing the amino acid sequence represented by SEQ ID NO:109;

(xxx) a DNA containing the base sequence represented by SEQ ID NO:124 or the like is used as the DNA encoding the polypeptide containing the amino acid sequence represented by SEQ ID NO:110;

(xxxi) a DNA containing the base sequence represented by SEQ ID NO:125 or the like is used as the DNA encoding the polypeptide containing the amino acid sequence represented by SEQ ID NO:6;

(xxxii) a DNA containing the base sequence represented by SEQ ID NO:121 or the like is used as the DNA encoding the polypeptide containing the amino acid sequence represented by SEQ ID NO:111;

(xxxiii) a DNA containing the base sequence represented by SEQ. ID NO:18 or the like is used as the DNA encoding the polypeptide containing the amino acid sequence represented by SEQ ID NO:112;

(xxxiv) a DNA containing the base sequence represented by SEQ ID NO:121 or the like is used as the DNA encoding the polypeptide containing the amino acid sequence represented by SEQ ID NO:113; and the like.

The DNA encoding the receptor of the present invention includes, for example, a DNA having the base sequence represented by SEQ ID NO:128, or a DNA having a base sequence hybridizable to the base sequence represented by SEQ ID NO:128 under high stringent conditions and encoding a polypeptide having an activity substantially equivalent to that of the receptor of the present invention, and the like. Any of such DNAs may be employed.

Examples of the DNA that is hybridizable to the base sequence represented by SEQ ID NO:128 include a DNA containing a base sequence having at least about 70% homology, preferably at least about 80% homology, more preferably at least about 90% homology and most preferably at least about 95% homology, to the base sequence represented by SEQ ID NO:128, and the like.

The hybridization can be carried out by publicly known methods or by modifications thereof, for example, according to the method described in Molecular Cloning, 2nd Ed. (J. Sambrook et al., Cold Spring Harbor Lab. Press, 1989), etc. A commercially available library may also be used according to the instructions of the attached manufacturer's protocol. The hybridization can be carried out preferably under high stringent conditions.

The high stringent conditions used herein are, for example, those in a sodium concentration at approximately 19 to 40 mM, preferably approximately 19 to 20 mM at a temperature of approximately 50 to 70° C., preferably approximately 60 to 65° C. In particular, hybridization conditions in a sodium concentration at about 19 mM at a temperature of about 65° C. are most preferred.

More specifically, a DNA containing the base sequence represented by SEQ ID NO:128, or the like is used as the DNA encoding the polypeptide containing the amino acid sequence represented by SEQ ID NO:129.

For the DNA encoding the partial peptide of the receptor of the present invention, any DNA can be used, so far as it contains a base sequence encoding the partial peptide of the receptor of the present invention described above. The DNA may be any of genomic DNA, genomic DNA library, cDNA derived from the cells/tissues described above, cDNA library derived from the cells/tissues described above, and synthetic DNA.

The DNA encoding the partial peptide of the receptor of the present invention includes, for example, a DNA having a partial base sequence of DNA containing the base sequence represented by SEQ ID NO:128, or a DNA having a base sequence hybridizable to the base sequence represented by SEQ ID NO:128 under high stringent conditions and having a partial base sequence of DNA encoding a polypeptide having an activity substantially equivalent to that of the receptor of the present invention, and the like.

The DNA that is hybridizable to the base sequence represented by SEQ ID NO:128 has the same significance as described above.

For the methods for hybridization and high stringent conditions, those described above are similarly used.

The DNA encoding the polypeptide, receptor or partial peptide of the present invention may be labeled by publicly known methods. Specific examples include those labeled with an isotope, those labeled with fluorescence (labeling with, e.g., fluorescein, etc.), those biotinated, those labeled with enzyme, etc.

For cloning of the DNA that completely encodes the polypeptide, receptor or partial peptide of the present invention (hereinafter the polypeptides or the like are sometimes merely referred to as the polypeptide of the present invention in the following description of cloning and expression of the DNA encoding these polypeptides or the like), the DNA may be either amplified by publicly known PCR using synthetic DNA primers containing a part of the base sequence of the polypeptide of the present invention, or the DNA inserted into an appropriate vector can be selected by hybridization with a labeled DNA fragment or synthetic DNA that encodes a part or entire region of the polypeptide of the present invention. The hybridization can be carried out, for example, according to the method described in Molecular Cloning, 2nd (J. Sambrook et al., Cold Spring Harbor Lab. Press, 1989), etc. The hybridization may also be performed using commercially available library in accordance with the protocol described in the attached instructions. Conversion of the base sequence of DNA can be made by publicly known methods such as the ODA-LA PCR method, the Gapped duplex method or the Kunkel method, or modifications thereof, by using a publicly known kit available as Mutan™-super Express Km (manufactured by Takara Shuzo Co., Ltd., trademark), Mutan™-K (manufactured by Takara Shuzo Co., Ltd., trademark), etc.

The cloned DNA encoding the polypeptide can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the polypeptide of the present invention can be manufactured, for example, by (a) excising the desired DNA fragment from the DNA encoding the polypeptide of the present invention, (b) and then ligating the DNA fragment with an appropriate expression vector downstream a promoter in the vector.

Examples of the vector include plasmids derived form $E.$ $coli$ (e.g., pBR322, pBR325, pUC12, pUC13), plasmids derived from $Bacillus$ $subtilis$ (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, HIV•LTR promoter, CMV promoter, HSV-TK promoter, etc.

Among them, CMV (cytomegalovirus) promoter or SRα promoter is preferably used. Where the host is bacteria of the genus $Escherichia,$ preferred examples of the promoter include trp promoter, lac promoter, recA promoter, $\lambda P_L$ promoter, lpp promoter, T7 promoter, etc. In the case of using bacteria of the genus $Bacillus$ as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin promoter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as Neo, G418 resistance), etc. In particular, when dhfr gene is employed as the selection marker using dhfr gene-deficient Chinese hamster cells, selection can also be made on thymidine free media.

If necessary, a signal sequence that matches with a host is added to the N-terminus of the polypeptide of the present invention. Examples of the signal sequence that can be used are Pho A signal sequence, OmpA signal sequence, etc. in the case of using bacteria of the genus $Escherichia$ as the host; α-amylase signal sequence, subtilisin signal sequence, etc. in the case of using bacteria of the genus $Bacillus$ as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding the polypeptide thus constructed, transformants can be manufactured.

Examples of the host, which may be employed, are bacteria belonging to the genus $Escherichia,$ bacteria belonging to the genus $Bacillus,$ yeast, insect cells, insects and animal cells, etc.

Specific examples of the bacteria belonging to the genus $Escherichia$ include $Escherichia$ $coli$ K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are. Sf9 cell (ATCC CRL1711), Sf21 cell (both cells are described in Vaughn, J. L. et al., In Vivo, 13, 213-217 (1977)), etc.

As the insect, for example, a larva of *Bombyx mori*, etc. can be used [Maeda et al., Nature, 315, 592 (1985)].

Examples of animal cells include monkey cell COS-7, Vero, Chinese hamster cell CHO (hereinafter simply referred to as CHO cell), dhfr gene deficient Chinese hamster cell CHO (hereinafter simply referred to as CHO (dhfr⁻) cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the polypeptide can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary and desired, a chemical such as 3β-indolylacrylic acid can be added to the medium thereby to activate the promoter efficiently.

Where the bacteria belonging to the genus *Escherichia* are used as the host, the transformant is usually cultivated at approximately 15 to 43° C. for approximately 3 to 24 hours. If necessary, the culture may be aerated or agitated.

Where the bacteria belonging to the genus *Bacillus* are used as the host, the transformant is cultivated generally at approximately 30 to 40° C. for approximately 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at approximately 20 to 35° C. for approximately 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture can be aerated or agitated.

As described above, the polypeptide of the present invention can be produced in the inside, cell membrane or outside of the transformant, etc.

The polypeptide of the present invention can be separated and purified from the culture described above, e.g., by the following procedures.

When the polypeptide of the present invention is extracted from the culture or cells, after cultivation the transformant or cell is collected by a publicly known method and suspended in an appropriate buffer. The transformant or cell is then disrupted by publicly known methods such as ultrasonication, a treatment with lysozyme and/or freeze-thaw cycling, followed by centrifugation, filtration, etc. Thus, the crude extract of the polypeptide can be obtained. The buffer used for the procedures may contain a protein modifier such as urea or guanidine hydrochloride, or a surfactant such as Triton X-100™, etc. When the polypeptide is secreted in the culture broth, after completion of the cultivation the supernatant can be separated from the transformant or cell to collect the supernatant by a publicly known method.

The supernatant or the polypeptide contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reversed phase high performance liquid chromatography, etc.; a method utilizing difference in isoelectric point such as isoelectrofocusing electrophoresis; and the like.

When the polypeptide thus obtained is in a free form, it can be converted into the salt by publicly known methods or modifications thereof. On the other hand, when the polypeptide is obtained in the form of a salt, it can be converted into the free form or in the form of a different salt by publicly known methods or modifications thereof.

The polypeptide produced by the recombinant can be treated, prior to or after the purification, with an appropriate protein modifying enzyme so that the protein or partial peptide can be appropriately modified to partially remove a polypeptide. Examples of the protein-modifying enzyme include trypsin, chymotrypsin, arginyl endopeptidase, protein kinase, glycosidase and the like.

Hereinafter, the screening method of the present invention will be described in detail.

(i) By using the receptor binding assay system via the expression system using the receptor of the present invention, its partial peptides, or salts thereof (hereinafter sometimes collectively referred to as the receptor of the present invention) or using the recombinant type receptor of the present invention, and (ii) by using the receptor binding assay system via the expression system using the polypeptide of the present invention or using the recombinant type polypeptide of the present invention, compounds (e.g., peptides, proteins, non-peptide compounds, synthetic compounds, fermentation products, etc.) or salts thereof that alter the binding property between the receptor of the present invention and the polypeptide of the present invention can be screened efficiently.

Such compounds or salts thereof include 1) compounds (agonists) that have the cell-stimulating activity (e.g., the activity that promotes arachidonic acid release, acetylcholine release, intracellular $Ca^{2+}$ release, intracellular cAMP production, suppression of intracellular cAMP production, intracellular cGMP production, inositol phosphate production, change in cell membrane potential, phosphorylation of intracellular proteins, activation of c-fos, pH reduction, GTPγ S binding activity, etc.) mediated by the receptor of the present invention; 2) compounds (antagonists) that do not have the cell-stimulating activity described above; 3) compounds that promote the binding of the receptor of the present invention to the ligand of the present invention, 4) compounds that inhibit the binding of the receptor of the present invention to the ligand of the present invention; and the like.

Specifically, comparison is made between (i) the case where the polypeptide of the present invention is brought in contact with the receptor of the present invention and (ii) the case where the polypeptide of the present invention and a test compound are brought in contact with the receptor of the present invention. The comparison is effected by assaying, for example, the binding amount of the polypeptide of the present invention to the receptor of the present invention, the cell-stimulating activity, or the like.

The screening method of the present invention includes, for example:

(1) a method of screening a compound or its salt that alters the binding property between the polypeptide of the present invention and the receptor of the present invention, which comprises assaying the binding amount of a labeled form of the polypeptide of the present invention to the receptor of the present invention, (i) in the case wherein a labeled form of the polypeptide of the present invention is brought in contact with the receptor of the present invention above and (ii) in the case wherein a labeled form of the polypeptide of the present invention and a test compound are brought in contact with the receptor of the present invention, and comparing (i) and (ii);

(2) a method of screening a compound or its salt that alters the binding property between the polypeptide of the present invention and the receptor of the present invention, which comprises assaying the binding amount of a labeled form of the polypeptide of the present invention to a cell containing the receptor of the present invention or its cell membrane, (i) in the case wherein a labeled form of the polypeptide of the present invention is brought in contact with the cell containing the receptor of the present invention or its cell membrane and (ii) in the case wherein a labeled form of the polypeptide of the present invention and a test compound are brought in contact with the cell containing the receptor of the present invention or its cell membrane, and comparing (i) and (ii);

(3) a method of screening a compound or its salt that alters the binding property between the polypeptide of the present invention and the receptor of the present invention, which comprises assaying the binding amount of a labeled form of the polypeptide of the present invention to the receptor of the present invention, (i) in the case wherein a labeled form of the polypeptide of the present invention is brought in contact with the receptor of the present invention expressed on a cell membrane by culturing a transformant containing a DNA encoding the receptor of the present invention and (ii) in the case wherein a labeled form of the polypeptide of the present invention and a test compound are brought in contact with the receptor of the present invention expressed on a cell membrane by culturing a transformant containing a DNA encoding the receptor of the present invention, and comparing (i) and (ii);

(4) a method of screening a compound or its salt that alters the binding property between the polypeptide of the present invention and the receptor of the present invention, which comprises assaying the cell-stimulating activity (e.g., the activity that promotes or suppresses arachidonic acid release, acetylcholine release, intracellular $Ca^{2+}$ release, intracellular cAMP production, suppression of intracellular cAMP production, intracellular cGMP production, inositol phosphate production, change in cell membrane potential, phosphorylation of intracellular proteins, activation of c-fos, pH reduction, GTPγ S binding activity, etc.) mediated by the receptor of the present invention, when the polypeptide of the present invention is brought in contact with a cell containing the receptor of the present invention and when the polypeptide of the present invention and a test compound are brought in contact with a cell containing the receptor of the present invention, and comparing the activity; and, (5) a method of screening a compound or its salt that alters the binding property between the polypeptide of the present invention and the receptor of the present invention, which comprises assaying the cell-stimulating activity (e.g., the activity that promotes or suppresses arachidonic acid release, acetylcholine release, intracellular $Ca^{2+}$ release, intracellular cAMP production, suppression of intracellular cAMP production, intracellular cGMP production, inositol phosphate production, change in cell membrane potential, phosphorylation of intracellular proteins, activation of c-fos, pH reduction, GTPγ S binding activity, etc.) mediated by the receptor of the present invention, when the polypeptide of the present invention is brought in contact with the receptor of the present invention expressed on a cell membrane by culturing a transformant containing a DNA encoding the receptor of the present invention and when the polypeptide of the present invention and a test compound are brought in contact with the receptor of the present invention expressed on a cell membrane by culturing a transformant containing a DNA encoding the receptor of the present invention, and comparing the activity; and the like.

The screening method of the present invention will be described below more specifically.

For the receptor of the present invention, membrane fractions from human or non-human warm-blooded animal organs are preferably employed. However, since it is very difficult to obtain human-derived organs especially, the receptor of the present invention, or the like, which is expressed abundantly by use of a recombinant, is suitable for use in the screening.

In manufacturing the receptor of the present invention, the methods of manufacturing the receptor of the present invention described above may be employed.

Where the cell containing the receptor of the present invention or its cell membrane fraction is used in the screening method of the present invention, the preparation procedures later described apply.

When the cell containing the receptor of the present invention is used in the screening method of the present invention, the cell may be fixed with glutaraldehyde, formalin, etc. The fixation may be carried out by a publicly known method.

The cell containing the receptor of the present invention refers to a host cell wherein the receptor of the present invention is expressed. Examples of such a host cell include *Escherichia coli, Bacillus subtilis*, yeast, insect cells, animal cells, etc. described above. Host cells in which the receptor of the present invention is expressed may be prepared in a manner similar to the above-described method for manufacturing transformants transformed by expression vectors containing the polypeptide of the present invention.

The membrane fraction refers to a fraction that abundantly contains cell membranes prepared by publicly known methods after disrupting cells. Examples of the cell disruption include cell squashing using a Potter-Elvehjem homogenizer, disruption using a Waring blender or Polytron (manufactured by Kinematica Inc.), disruption by ultrasonication, disruption by cell spraying via a thin nozzle under increasing pressure using a French press, etc., and the like. Cell membranes are fractionated mainly by fractionation using a centrifugal force such as for fractionation centrifugation, density gradient centrifugation, etc. For example, cell disruption fluid is centrifuged at a low rate (500 rpm to 3,000 rpm) for a short period of time (normally about 1 minute to about 10 minutes), the resulting supernatant is then centrifuged at a higher rate (15,000 rpm to 30,000 rpm) normally for 30 minutes to 2 hours. The precipitate thus obtained is used as the membrane fraction. The membrane fraction is rich in the receptor expressed and membrane components such as cell-derived phospholipids, membrane proteins, or the like.

The amount of the receptor of the present invention in the cells containing the receptor of the present invention or in the membrane fraction is preferably $10^3$ to $10^8$ molecules per cell, more preferably $10^5$ to $10^7$ molecules per cell. As the level of expression increases, the ligand binding activity per unit of membrane fraction (specific activity) increases so that not only the highly sensitive screening system can be constructed but also large quantities of samples can be assayed with the same lot.

To perform the screening methods (1) through (3) described above, an appropriate fraction of the receptor of the present invention and a labeled form of the polypeptide of the present invention, etc. are required. The fraction of the receptor of the present invention is preferably a fraction of a naturally occurring form of the receptor of the present invention or a fraction of a recombinant type of the receptor of the present invention having an activity equivalent thereto. Herein, the term equivalent activity is intended to mean an equivalent ligand binding activity, etc. As the labeled ligand, there may be used a labeled ligand, a labeled ligand analog compound, etc. For example, there may be used ligands that are labeled with [$^3$H], [$^{125}$I], [$^{14}$C], [$^{35}$S], etc.

Specifically, the compound that alters the binding property between the polypeptide of the present invention and the receptor of the present invention is screened by the following procedures. First, a receptor preparation is prepared by suspending cells containing the receptor of the present invention or its membrane fraction in a buffer appropriate for use in the screening method. Any buffer can be used so long as it does not interfere the ligand-receptor binding, including a phosphate buffer or a Tris-HCl buffer, having pH of 4 to 10 (preferably pH of 6 to 8), etc. For the purpose of minimizing non-specific binding, a surfactant such as CHAPS, Tween-80™ (Polyoxyethlene 20 Sorbitan Monooleate, Kao-Atlas Inc.), digitonin, deoxycholate, etc., may optionally be added to the buffer. Further for the purpose of suppressing the degradation of the receptor of the present invention or the polypeptide of the present invention with a protease, a protease inhibitor such as PMSF, leupeptin, E-64 (manufactured by Peptide Institute, Inc.), pepstatin, etc. may also be added. A given amount (5,000 cpm to 500,000 cpm) of the labeled polypeptide of the present invention is added to 0.01 ml to 10 ml of the receptor solution, in which $10^{-10}$ M to $10^{-7}$ M of a test compound is co-present. To determine the amount of non-specific binding (NSB), a reaction tube charged with an unlabeled form of the polypeptide of the present invention in a large excess is also provided. The reaction is carried out at approximately 0° C. to 50° C., preferably 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$ minus NSB) is made 100%, the test compound showing the specific binding amount (B minus NSB) of, e.g., 50% or less may be selected as a candidate compound.

To perform the screening method (4) or (5) described above, the cell stimulating activity (e.g., the activity that promotes or suppresses arachidonic acid release, acetylcholine release, intracellular $Ca^{2+}$ release, intracellular cAMP production, suppression of intracellular cAMP production, intracellular cGMP production, inositol phosphate production, change in cell membrane potential, phosphorylation of intracellular proteins, activation of c-fos, pH reduction, GTPγ S binding activity, etc.) mediated by the receptor of the present invention may be determined by a publicly known method, or using an assay kit commercially available; Specifically, the cells containing the receptor of the present invention are first cultured on a multiwell plate, etc. Prior to screening, the medium is replaced with, fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., arachidonic acid, etc.) due to a degrading enzyme contained in the cells, an inhibitor against such as a degrading enzyme may be added prior to the assay. For detecting the activity such as the cAMP production suppression, the baseline production in the cells is previously increased by forskolin or the like and the suppressing effect on the increased baseline production can be detected.

For screening through the assay of the cell stimulating activity, appropriate cells, in which the receptor of the present invention is expressed, are required. Preferred cells, in which the receptor of the present invention is expressed, are the aforesaid cell line wherein the receptor of the present invention is expressed, etc.

Examples of the test compound include peptides, proteins, non-peptide compounds, synthetic compounds, fermentation products, cell extracts, plant extracts, animal tissue extracts, etc.

A kit for screening the compound or a salt thereof that alters the binding property between the polypeptide of the present invention and the receptor of the present invention comprises the receptor of the present invention, or cells containing the receptor of the present invention or a membrane fraction of the cells, and the polypeptide of the present invention.

Examples of the screening kit of the present invention are given below.

1. Reagent for Screening
(a) Assay Buffer and Wash Buffer

Hanks' Balanced Salt Solution (manufactured by Gibco Co.) supplemented with 0.05% bovine serum albumin (Sigma Co.).

The solution is sterilized by filtration through a 0.45 µm filter and stored at 4° C. Alternatively, the solution may be prepared at use.

(b) Preparation of the Receptor of the Present Invention

CHO cells wherein the receptor of the present invention has been expressed are subcultured in a 12-well plate at $5 \times 10^5$ cells/well and then cultured at 37° C. under 5% $CO_2$ and 95% air for 2 days.

(c) Labeled Ligand

The polypeptide of the present invention labeled with commercially available [$^3$H], [$^{125}$I], [$^{14}$C], [$^{35}$S], etc. is dissolved in a suitable solvent or buffer. The solution is stored at 4° C. or −20° C., which is diluted to 1 µM with an assay buffer at use.

(d) Standard Ligand Solution

The polypeptide of the present invention is dissolved in PBS supplemented with 0.1% bovine serum albumin (manufactured by Sigma, Inc.) in a concentration of 1 mM, and the solution is stored at −20° C.

2. Assay Method (a) Cells are cultured in a 12-well tissue culture plate to express the receptor of the present invention. After washing the cells twice with 1 ml of the assay buffer, 490 µl of the assay buffer is added to each well.

(b) After 5 µl of a test compound solution of $10^{-3}$ to $10^{-10}$ M is added, 5 µl of a labeled form of the peptide of the present invention is added to the system followed by reacting at room temperature for an hour. To determine the amount of the non-specific binding, the polypeptide of the present invention of $10^{-3}$ M is added in an amount of 5 µl, instead of the test compound.

(c) The reaction mixture is removed and washed 3 times with 1 ml each of the wash buffer. The labeled polypeptide of the present invention bound to the cells is dissolved in 0.2N NaOH-1% SDS and mixed with 4 ml of a liquid scintillator A (manufactured by Wako Pure Chemical Industries, Ltd.).

(d) Radioactivity is measured using a liquid scintillation counter (manufactured by Beckmann) and PMB (percent of the maximum binding) is calculated in accordance with the following equation 1:

$$PMB=[(B-NSB)/(B_0-NSB)] \times 100$$

wherein:

| | |
|---|---|
| PMB: | percent of the maximum binding |
| B: | value when a sample is added |
| NSB: | non-specific binding |
| $B_0$: | maximum binding |

The compound or its salt, which is obtainable by the screening method or the screening kit of the present invention, is the compound that alters the binding property between the polypeptide of the present invention and the receptor of the present invention, or the compound that promotes or inhibits the activity of the receptor of the present invention. Specifically, these compounds are 1) compounds or salts thereof that exhibit the cell stimulating activity mediated by the receptor of the present invention (the receptor agonists of the present invention), 2) compounds that do not exhibit the cell stimulating activity (the receptor antagonists of the present invention), 3) compounds that promote the binding of the receptor of the present invention to the ligand of the present invention, 4) compounds that inhibit the binding of the receptor of the present invention to the ligand of the present invention; etc. Examples of such compounds include compounds selected from peptides, proteins, non-peptide compounds, synthetic compounds, fermentation products, cell extracts, plant extracts, animal tissue extracts, plasma, etc. These compounds may be either novel or publicly known compounds.

As salts of these compounds, there may be used those similar to the salts of the polypeptide of the present invention described above.

In order to evaluate whether the compound is the receptor agonist or antagonist of the present invention described above, it is determined by (i) or (ii) below.

(i) According to the screening methods (1) to (3), binding assay is carried out to obtain the compound that alters the binding property between the polypeptide of the present invention and the receptor of the present invention (especially, the compound that inhibits the binding). It is then determined if the compound has the above cell-stimulating activity mediated by the receptor of the present invention. The compound or its salt having the cell-stimulating activity is the receptor agonist of the present invention, whereas the compound or its salt having no such an activity is the receptor antagonist of the present invention.

(ii) (a) A test compound is brought in contact with a cell containing the receptor of the present invention, whereby the aforesaid cell-stimulating activity mediated by the receptor of the present invention is assayed. The compound or its salt having the cell-stimulating activity is the receptor agonist of the present invention.

(b) The cell-stimulating activity mediated by the receptor of the present invention is assayed in the case where the polypeptide of the present invention is brought in contact with cells containing the receptor of the present invention and in the case where the polypeptide of the present invention and a test compound are brought in contact with cells containing the receptor of the present invention, and compared therebetween. The compound or its salt that can reduce the cell-stimulating activity induced by the compound that activates the receptor of the present invention is the receptor antagonist of the present invention.

The receptor agonists of the present invention exhibit similar physiological activity [(e.g., an appetite (eating) stimulating activity)] possessed by the polypeptide of the present invention on the receptor of the present invention, and are thus safe and low-toxic drugs (e.g., preventive/therapeutic drugs for anorexia nervosa, appetite (eating) stimulants, etc.).

The receptor antagonists of the present invention can suppress the physiological activity [(e.g., an appetite (eating) stimulating activity)] that the polypeptide of the present invention has on the receptor of the present invention, and are thus useful as safe and low-toxic drugs for the treatment/prevention of, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc.

The compounds that promote the binding of the receptor of the present invention to the ligand of the present invention are useful as safe and low-toxic drugs (e.g., preventive/therapeutic drugs for anorexia nervosa, appetite (eating) stimulants, etc.).

The compounds that inhibit the binding of the receptor of the present invention to the ligand of the present invention are useful as safe and low-toxic drugs for the treatment/prevention of, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc.

When the compound or its salts obtained by the screening method or screening kit of the present invention are used as the drugs (prophylactic/therapeutic agents) described above, the compound or its salts can be prepared into pharmaceutical preparations in a conventional manner.

For example, the compound or its salts may be used orally, for example, in the form of tablets optionally coated with sugar, capsules, elixir, microcapsule, etc., or parenterally in the form of injectable preparations such as a sterile solution, a suspension, etc., in water or with other pharmaceutically acceptable liquid (e.g., intravenously, subcutaneously, pernasally, etc.). These preparations can be manufactured by mixing the polypeptide of the present invention with a physiologically acceptable known carrier, a flavoring agent, an excipient, a vehicle, an antiseptic agent, a stabilizer a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose and saccharin, and a flavoring agent such as peppermint, akamono oil or cherry, and the like. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc.

Examples of an aqueous medium for injection include physiological saline and an isotonic solution containing glucose and other auxiliary agents (e.g., D-sorbitol, D-mannitol, sodium chloride, etc.), etc. and may be used in combination with an appropriate dissolution aid such as an alcohol (e.g., ethanol or the like), a polyalcohol (e.g., propylene glycol, polyethylene glycol, etc.), a nonionic surfactant (e.g., polysorbate 80™ (Polyoxyethylene 20 Sorbitan Monooleate)), HCO-50, etc.), and the like. Examples of the oily medium include sesame oil, soybean oil, etc., which may also be used in combination with a dissolution aid such as benzyl benzoate, benzyl alcohol, etc. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the thus obtained pharmaceutical preparation is safe and low toxic, the preparation can be administered to human or non-human warm-blooded animal (e.g., mouse, rat, rabbit, sheep, swine, bovine, horse, chicken, cat, dog, monkey, chimpanzee, etc.).

The dose of the compound or its salts may vary depending on its action, target disease, subject to be administered, route for administration, etc.

The compound (agonist) is orally administered to the patient, for example, with anorexia nervosa (as 60 kg body weight) in a dose of about 0.1 to 100 mg, preferably about 1.0 to 50 mg, and more preferably about 1.0 to 20 mg per day. In parenteral administration when the compound is administered to the patient, for example, with anorexia nervosa (as 60 kg body weight) in the form of injection, it is advantageous to administer the compound intravenously at a daily dose of about 0.01 to 30 mg, preferably about 0.1 to 20 mg, and more preferably about 0.1 to 10 mg. Preferably, the compound is administered to the nerve center, or administered in a dosage form having high transportability for the nerve center. For other animal species, the corresponding dose as converted per 60 kg body weight can be administered.

Furthermore, the compound (antagonist) is orally administered to the patient, for example, with obesity (as 60 kg body weight) in a dose of about 0.1 to 100 mg, preferably about 1.0 to 50 mg, and more preferably about 1.0 to 20 mg per day. In parenteral administration when the compound is administered to the patient, for example, with obesity (as 60 kg body weight) in the form of injection, it is advantageous to administer the compound intravenously at a daily dose of about 0.01 to 30 mg, preferably about 0.1 to 20 mg, and more preferably about 0.1 to 10 mg. Preferably, the compound is administered to the nerve center, or administered in a dosage form having high transportability for the nerve center. For other animal species, the corresponding dose as converted per 60 kg body weight can be administered.

Furthermore, the present invention provides the utilities of (a) the receptor of the present invention, (b) the DNA of the present invention, (c) the antibody of the present invention, and (d) the antisense DNA. Hereinafter, the receptor of the present invention and the DNA encoding the receptor or its partial peptide are sometimes merely referred to as the DNA of the present invention.

(1) Preventive/Therapeutic Agent for Diseases with Which the Receptor of the Present Invention is Associated Response of the receptor of the present invention to the polypeptide of the present invention results in stimulation of eating behaviors.

Therefore, when the receptor of the present invention or the DNA of the present invention involves any abnormality or deficiency, or when the receptor of the present invention or the DNA encoding the receptor involves any abnormality or deficiency, it is highly likely to cause, e.g., anorexia nervosa, anorexia, etc. Thus, the receptor of the present invention and the polynucleotide (e.g., DNA) encoding the receptor can be used as preventive/therapeutic agents for, e.g., anorexia nervosa, appetite (eating) stimulants, etc.

When a patient has a reduced level of, or deficient in the receptor of the present invention in his or her body, the receptor of the present invention and the DNA of the present invention can provide the role of the receptor of the present invention sufficiently or properly for the patient, (a) by administering the DNA of the present invention to the patient to express the receptor of the present invention in the body, (b) by inserting the DNA of the present invention into a cell, expressing the receptor of the present invention and then transplanting the cell to the patient, or (c) by administering the receptor of the present invention to the patient, or the like.

When the DNA of the present invention is used as the preventive/therapeutic agents described above, the DNA is administered directly to human or non-human warm-blooded animal; alternatively, the DNA is inserted into an appropriate vector such as retrovirus vector, adenovirus vector, adenovirus-associated virus vector, etc. and then administered to human or non-human warm-blooded animal in a conventional manner. The DNA of the present invention may also be administered as naked DNA, or with adjuvants to assist its uptake by gene gun or through a catheter such as a catheter with a hydrogel.

Where the receptor of the present invention is used as the aforesaid preventive/therapeutic agents, the receptor is advantageously used on a purity level of at least 90%, preferably at least 95%, more preferably at least 98% and most preferably at least 99%.

The receptor of the present invention can be used orally, for example, in the form of tablets which, if necessary, may be sugar-coated, capsules, elixirs, microcapsules etc., or parenterally in the form of injectable preparations such as a sterile solution and a suspension in water or with other pharmaceutically acceptable liquid (e.g., intravenously, subcutaneously, pernasally, etc., preferably subcutaneously). These preparations can be manufactured by mixing the receptor of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol, polyethylene glycol, etc.), a nonionic surfactant (e.g., polysorbate 80™ ((Polyoxyethylene 20 Sorbitan Monooleate)), HCO-50, etc.), or the like. Examples of the oily medium include sesame oil, soybean oil and the like, which may also be used in combination with a dissolution aid such as benzyl benzoate, benzyl alcohol, etc. The preventive/therapeutic agents described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNA of the present invention is inserted may also be prepared into pharmaceutical preparations in a manner similar to the procedures above. Such preparations are generally used parenterally.

Since the thus obtained pharmaceutical preparation is safe and low toxic, the preparation may be administered to human or non-human warm-blooded animal (e.g., rat, mouse, guinea pig, rabbit, chicken, sheep, swine, bovine, horse, cat, dog, monkey, etc.).

The dose of the receptor of the present invention may vary depending on target disease, subject to be administered, route for administration, etc.; for example, where the receptor of the present invention is subcutaneously administered as an appetite stimulant, the dose is normally about 0.1 mg to about 100 mg, preferably about 1.0 to about 50 mg, and more preferably about 1.0 to about 20 mg per day for adult (as 60 kg body weight). Preferably, the compound is administered to the nerve center, or administered in a dosage form that is highly transportable to the nerve center. For other animal species, the corresponding dose as converted per 60 kg body weight can be administered.

(2) Gene Diagnostic Agent

By using the DNA of the present invention, e.g., as a probe, abnormality (gene abnormality) of the DNA or mRNA encoding the receptor of the present invention in human or non-human warm-blooded animal (e.g., rat, mouse, guinea pig, rabbit, chicken, sheep, swine, bovine, horse, cat, dog, monkey, etc.) can be detected. Thus, the DNA of the present invention is useful as a gene diagnostic agent for the damage to the DNA or mRNA, mutation, a decreased expression or an increased expression, or overexpression of the DNA or mRNA.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)), etc.

When a decreased expression is detected, e.g., by the Northern hybridization, it can be diagnosed that one is likely to suffer from, for example, anorexia nervosa, or it is highly likely for one to suffer from anorexia nervosa in the future.

When overexpression is detected by the Northern hybridization, it can be diagnosed that one is likely to suffer from, for example, obesity; or it is highly likely for one to suffer from obesity in the future.

(3) Antiobesity Agent and Diagnostic Agent Comprising the Antibody

The antibodies to the receptor of the present invention (hereinafter sometimes simply referred to as the antibody (ies) of the present invention) may be any of polyclonal antibodies and monoclonal antibodies, as long as they are capable of recognizing antibodies to the receptor of the present invention, its partial peptides, or salts thereof.

The antibodies to the receptor of the present invention may be manufactured by publicly known methods for manufacturing antibodies or antisera, using the receptor of the present invention as an antigen.

[Production of Monoclonal Antibody]

(a) Production of Monoclonal Antibody-producing Cells

The receptor of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after two to five days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled receptor, which will be described later, with the antiserum followed by assaying the binding activity of the labeling agent bound to the antibody. The fusion may be carried out, for example, by the known method by Koehler and Milstein [Nature, 256, 495 (1975)]. Examples of the fusion promoter are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the receptor as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the receptor labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like can be used for the selection and growth medium. The cultivation is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with ah activated adsorbent such as an antigen-binding solid phase, Protein A or Protein G and dissociating the binding to obtain the antibody].

[Production of Polyclonal Antibody]

The polyclonal antibody of the present invention can be manufactured by publicly known methods or modifications thereof. For example, a warm-blooded animal is immunized with an immunogen (receptor antigen) per se, or a complex of immunogen and a carrier protein is formed and a warm-blooded animal is immunized with the complex in a manner similar to the method described above for the manufacture of monoclonal antibodies. The product containing the antibody to the receptor of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin, hemocyanin or the like is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once approximately every 2 to 6 weeks and approximately 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antibodies of the present invention can be used as preventive/therapeutic agents of, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc., preferably as antiobesity agents, etc.

The preventive/therapeutic agents for diseases described above comprising the antibody of the present invention can be administered to human or non-human warm-blooded animal (e.g., rat, rabbit, sheep, swine, bovine, cat, dog, monkey, etc.) orally or parenterally directly as a liquid preparation, or as a pharmaceutical composition in an appropriate preparation form. The dose varies depending on subject to be administered, target disease, conditions, route for administration, etc.; when it is used as, e.g., an antiobesity agent for adult, the antibody of the present invention is advantageously administered through intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to 5 times, preferably approximately 1 to 3 times, per day. For other parenteral administration and oral administration, the corresponding dose may be administered. When the conditions are extremely serious, the dose may be increased depending on the conditions.

The antibody of the present invention may be administered directly as it is or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections, etc. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol or polyethylene glycol), nonionic surfactant [e.g., polysorbate 80, HCO-50 (polyoxyethylene (50 mol) adduct of hydrogenated castor oil)] may be used in combination. For the oily solution, for example, sesame oil, soybean oil and the like are used, and dissolution aids such as benzyl benzoate, benzyl alcohol, etc. may be used in combination. The thus-prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components unless formulation with the antibody causes any adverse interaction.

(5) Pharmaceutical Composition Comprising Antisense DNA

The antisense DNAs having a complementary or substantially complementary base sequence to the receptor of the present invention or to the DNA encoding the receptor or its partial peptide (hereinafter these DNAs are sometimes merely referred to as the antisense DNA) can be any antisense DNA, so long as they possess a complementary or substantially complementary base sequence to the DNA of the present invention and capable of suppressing expression of the DNA.

The base sequence substantially complementary to the DNA of the present invention may be, for example, a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). In the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence which encodes the N-terminal region of the receptor of the present invention (e.g., the base sequence, etc. around the initiation codon). These antisense DNAs can be synthesized using a publicly known DNA synthesizer, etc.

The antisense DNA that binds complementarily to the DNA of the present invention to suppress expression of the DNA, can be used as a preventive/therapeutic agent of, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc., preferably as antiobesity agents, etc.

For example, when the antisense DNA is used, the antisense DNA is administered directly, or the antisense DNA is inserted into an appropriate vector such as retrovirus vector, adenovirus vector, adenovirus-associated virus vector, etc. and then administered in a conventional manner. The antisense DNA may also be administered as intact DNA, or with adjuvants to assist its uptake by gene gun or through a catheter such as a catheter with a hydrogel.

In addition, the antisense DNA may also be employed as an oligonucleotide probe for diagnosis to examine the presence of the DNA of the present invention in tissues or cells or the state of its expression.

The present invention further provides:

(i) a double-stranded RNA containing a part of the RNA encoding the receptor of the present invention, (ii) a pharmaceutical comprising the double-stranded RNA described above;

(iii) a ribozyme containing a part of the RNA encoding the protein of the presert invention;

(iv) a pharmaceutical comprising the ribozyme described above;

(v) an expression vector containing a gene (DNA) encoding the ribozyme described above; etc.

As in the antisense nucleotide described above, the double-stranded RNA, ribozyme, etc. can destroy RNA transcribed from the DNA of the present invention or suppress functions of the RNA and can thus suppress the functions of the receptor or DNA of the invention in vivo and therefore, can be used as a preventive/therapeutic agent of, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc., preferably as antiobesity agents, etc.

The double-stranded RNA can be manufactured by designing the same based on the sequence of the polynucleotide of the present invention, by a modification of publicly known methods (e.g., Nature, 411, 494, 2001).

The ribozyme can be manufactured by designing the same based on the sequence of the polynucleotide of the present invention, by a modification of publicly known methods (e.g., TRENDS in Molecular Medicine, 7, 221, 2001). For example, the ribozyme designing the same based on the sequence of the polynucleotide of the present invention, can be manufactured by ligating a publicly known ribozyme to a part of the RNA encoding the receptor of the present invention. The part of the RNA encoding the receptor of the invention includes a sequence, etc., contiguous to the consensus sequence NUX (wherein N represents all bases and X represents bases other than G), which can be cleaved by a publicly known ribozyme.

Where the double-stranded RNA or ribozyme described above is used as the preventive/therapeutic agent described above, the RNA or ribozyme may be prepared into pharmaceutical preparations, as in the antisense polynucleotide, which are then provided for administration. The expression vector (v) described above is used as the preventive/therapeutic agent described above, using the vector as in publicly known gene therapy, etc.

In the specification and drawings, the codes of bases, amino acids, etc. are shown by abbreviations and in this case, they are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA: | deoxyribonucleic acid |
| cDNA: | complementary deoxyribonucleic acid |
| A: | adenine |
| T: | thymine |
| G: | guanine |
| C: | cytosine |
| I: | inosine |
| R: | adenine (A) or guanine (G) |
| Y: | thymine (T) or cytosine (C) |
| M: | adenine (A) or cytosine (C) |
| K: | guanine (G) or thymine (T) |
| S: | guanine (G) or cytosine (C) |
| W: | adenine (A) or thymine (T) |
| B: | guanine (G), guanine (G) or thymine (T) |
| D: | adenine (A), guanine (G) or thymine (T) |
| V: | adenine (A), guanine (G) or cytosine (C) |
| N: | adenine (A), guanine (G), cytosine (C) or thymine (T), or unknown or other base |
| RNA: | ribonucleic acid |
| mRNA: | messenger ribonucleic acid |
| dATP: | deoxyadenosine triphosphate |
| dTTP: | deoxythymidine triphosphate |
| dGTP: | deoxyguanosine triphosphate |
| dCTP: | deoxycytidine triphosphate |
| ATP: | adenosine triphosphate |
| EDTA: | ethylenediaminetetraacetic acid |
| SDS: | sodium dodecyl sulfate |
| BHA: | benzhydrylamine |
| pMBHA: | p-methyobenzhydrylamine |
| Tos: | p-toluenesulfonyl |
| Bzl: | benzyl |
| Bom: | benzyloxymethyl |
| Boc: | t-butyloxycarbonyl |
| DCM: | dichloromethane |
| HOBt: | 1-hydroxybenztriazole |
| DCC: | N,N'-dicyclohexylcarbodiimide |
| TFA: | trifluoroacetic acid |
| DIEA: | diisopropylethylamine |
| BSA: | bovine serum albumin |
| CHAPS: | 3-[(3-choramidopropyl)dimethylammonio]-1-propanesulfonate |
| Gly or G: | glycine |
| Ala or A: | alanine |
| Val or V: | valine |
| Leu or L: | leucine |
| Ile or I: | isoleucine |
| Ser or S: | serine |
| Thr or T: | threonine |

-continued

| | |
|---|---|
| Cys or C: | cysteine |
| Met or M: | methionine |
| Glu or E: | glutamic acid |
| Asp or D: | aspartic acid |
| Lys or K: | lysine |
| Arg or R: | arginine |
| His or H: | histidine |
| Phe or F: | phenylalanine |
| Tyr or Y: | tyrosine |
| Trp or W: | tryptophan |
| Pro or P: | proline |
| Asn or N: | asparagine |
| Gln or Q: | glutamine |
| pGlu: | pyroglutamic acid |
| Tyr (I): | 3-iodotyrosine |
| DMF: | N,N-dimethylformamide |
| Fmoc: | N-9-fluorenylmethoxycarbonyl |
| Trt: | trityl |
| Pbf: | 2,2,4,6,7-pentamethyldihydrobenzofuran-5-sulfonyl |
| Clt: | 2-chlorotrityl |
| Bu$^t$: | t-butyl |
| Met (O): | methionine sulfoxide |

The sequence identification numbers in the sequence listing of the specification indicates the following sequences, respectively.

[SEQ ID NO: 1]
This shows a synthetic DNA used for screening of cDNA encoding human GPR8.

[SEQ ID NO: 2]
This shows a synthetic DNA used for screening of cDNA encoding human GPR8.

[SEQ ID NO: 3]
This shows the entire base sequence of human GPR8 cDNA, to which the base sequence recognized by restriction enzyme ClaI is added at the 5' end and the base sequence recognized by restriction enzyme SpeI is added at the 3' end.

[SEQ ID NO: 4]
This shows the entire amino acid sequence of human GPR8.

[SEQ ID NO: 5]
This shows the sequence of riboprobe used to determine the expression level of GPR8 receptor protein mRNA in each clone of GPR8-expressed CHO cell line.

[SEQ ID NO: 6]
This shows the amino acid sequence obtained as a result of the amino terminal amino acid sequencing of ligand peptide to GPR8 purified from porcine hypothalamus.

[SEQ ID NO: 7]
This shows an EST sequence (Accession No. AW007531), which complementary strand is supposed to encode a part of the precursor protein of a human homologue to GPR8 ligand peptide.

[SEQ ID NO: 8]
This shows an EST sequence (Accession No. AI500303), which complementary strand is supposed to encode a part of the precursor protein of a human homologue to GPR8 ligand peptide.

[SEQ ID NO: 9]
This shows an EST sequence (Accession No. AI990964), which complementary strand is supposed to encode a part of the precursor protein of a human homologue to GPR8 ligand peptide.

[SEQ ID NO: 10]
This shows an EST sequence (Accession No. AA744804), which complementary strand is supposed to encode a part of the precursor protein of a human homologue to GPR8 ligand peptide.

[SEQ ID NO: 11]
This shows an EST sequence (Accession No. H31598) supposed to encode a part of the precursor protein of a rat homologue to GPR8 ligand peptide.

[SEQ ID NO: 12]
This shows a synthetic DNA used for screening cDNA encoding a part of the precursor protein of a human homologue of the ligand peptide to GPR8.

[SEQ ID NO: 13]
This shows a synthetic DNA used for screening cDNA encoding a part of the precursor protein of a human homologue of the ligand peptide to GPR8.

[SEQ ID NO: 14]
This shows the DNA sequence encoding a part of the precursor protein of a human homologue of the ligand peptide to GPR8 amplified from human brain-derived cDNA.

[SEQ ID NO: 15]
This shows the amino acid sequence for a part of the precursor protein of a human homologue of the ligand peptide to GPR8.

[SEQ ID NO: 16]
This shows the amino acid sequence of a human homologue of the ligand peptide to GPR8 deduced from SEQ ID NO: 15.

[SEQ ID NO: 17]
This shows the amino acid sequence of a human homologue of the ligand peptide to GPR8 deduced from SEQ ID NO: 15.

[SEQ ID NO: 18]
This shows the base sequence encoding the amino acid sequence represented by SEQ ID NO: 16.

[SEQ ID NO: 19]
This shows the base sequence encoding the amino acid sequence represented by SEQ ID NO: 17.

[SEQ ID NO: 20]
This shows the amino acid sequence of human GPR ligand (1-29) synthesized in REFERENCE EXAMPLE 14 described hereinafter.

[SEQ ID NO: 21]
This shows the amino acid sequence of human GPR ligand (1-28) synthesized in REFERENCE EXAMPLE 15 described hereinafter.

[SEQ ID NO: 22]
This shows the amino acid sequence of human GPR ligand (1-27) synthesized in REFERENCE EXAMPLE 16 described hereinafter.

[SEQ ID NO: 23]
This shows the amino acid sequence of human GPR ligand (1-26) synthesized in REFERENCE EXAMPLE 17 described hereinafter.

[SEQ ID NO: 24]
This shows the amino acid sequence of human GPR ligand (1-25) synthesized in REFERENCE EXAMPLE 18 described hereinafter.

[SEQ ID NO: 25]
This shows the amino acid sequence of human GPR ligand (1-24) synthesized in REFERENCE EXAMPLE 19 described hereinafter.

[SEQ ID NO: 26]
This shows the base sequence encoding the amino acid sequence represented by SEQ ID NO: 20.

[SEQ ID NO: 27]
This shows the base sequence encoding the amino acid sequence represented by SEQ ID NO: 21.

[SEQ ID NO: 28]
This shows the base sequence encoding the amino acid sequence represented by SEQ ID NO: 22.

[SEQ ID NO: 29]
This shows the base sequence encoding the amino acid sequence represented by SEQ ID NO: 23.

[SEQ ID NO: 30]
This shows the base sequence encoding the amino acid sequence represented by SEQ ID NO: 24.

[SEQ ID NO: 31]
This shows the base sequence encoding the amino acid sequence represented by SEQ ID NO: 25.

[SEQ ID NO: 32]
This shows the base sequence encoding the amino acid sequence represented by SEQ ID NO: 4.

[SEQ ID NO: 33]
This shows a synthetic DNA used to acquire the 5' upstream sequence of cDNA encoding the precursor protein of a human homologue of the ligand peptide to GPR8.

[SEQ ID NO: 34]
This shows a synthetic DNA used to acquire the 5' upstream sequence of cDNA encoding the precursor protein of a human homologue of the ligand peptide to GPR8.

[SEQ ID NO: 35]
This shows the DNA sequence at the 5' upstream side of cDNA encoding the precursor protein of a human homologue of the ligand peptide to GPR8.

[SEQ ID NO: 36]
This shows a synthetic DNA used to acquire the 3' downstream sequence of cDNA encoding the precursor protein of a human homologue of the ligand peptide to GPR8.

[SEQ ID NO: 37]
This shows a synthetic DNA used to acquire the 3' downstream sequence of cDNA encoding the precursor protein of a human homologue of the ligand peptide to GPR8.

[SEQ ID NO: 38]
This shows the DNA sequence at the 3' downstream side of cDNA encoding the precursor protein of a human homologue of the ligand peptide to GPR8.

[SEQ ID NO: 39]
This shows a synthetic DNA used to acquire cDNA encoding the precursor protein of a human homologue of the ligand peptide to GPR8.

[SEQ ID NO: 40]
This shows a synthetic DNA used to acquire cDNA encoding the precursor protein of a human homologue of the ligand peptide to GPR8.

[SEQ ID NO: 41]
This shows the sequence of cDNA encoding the precursor protein of a human homologue of the ligand peptide to GPR8.

[SEQ ID NO: 42]
This shows the amino acid sequence of the precursor protein of a human homologue of the ligand peptide to GPR8.

[SEQ ID NO: 43]
This shows a synthetic DNA used to acquire the 5' upstream sequence of cDNA encoding the precursor protein of a porcine homologue of the ligand peptide to GPR8.

[SEQ ID NO: 44]
This shows a synthetic DNA used to acquire the 5' upstream sequence of cDNA encoding the precursor protein of a porcine homologue of the ligand peptide to GPR8.

[SEQ ID NO: 45]
This shows the DNA sequence at the 5' upstream side of cDNA encoding the precursor protein of a porcine homologue of the ligand peptide to GPR8.

[SEQ ID NO: 46]
This shows a synthetic DNA used to acquire the 5' upstream sequence of cDNA encoding the precursor protein of a porcine homologue of the ligand peptide to GPR8.

[SEQ ID NO: 47]
This shows a synthetic DNA used to acquire the 5' upstream sequence of cDNA encoding the precursor protein of a porcine homologue of the ligand peptide to GPR8.

[SEQ ID NO: 48]
This shows the DNA sequence at the 5' upstream side of cDNA encoding the precursor protein of a porcine homologue of the ligand peptide to GPR8.

[SEQ ID NO: 49]
This shows a synthetic DNA used to acquire the 3' downstream sequence of cDNA encoding the precursor protein of a porcine homologue of the ligand peptide to GPR8.

[SEQ ID NO: 50]
This shows a synthetic DNA used to acquire the 3' downstream sequence of cDNA encoding the precursor protein of a porcine homologue of the ligand peptide to GPR8.

[SEQ ID NO: 51]
This shows the DNA sequence at the 3' downstream side of cDNA encoding the precursor protein of a porcine homologue of the ligand peptide to GPR8.

[SEQ ID NO: 52]
This shows a synthetic DNA used to acquire cDNA encoding the precursor protein of a porcine homologue of the ligand peptide to GPR8.

[SEQ ID NO: 53]
This shows a synthetic DNA used to acquire cDNA encoding the precursor protein of a porcine homologue of the ligand peptide to GPR8.

[SEQ ID NO: 54]
This shows the sequence of cDNA encoding the precursor protein of a porcine homologue of the ligand peptide to GPR8.

[SEQ ID NO: 55]
This shows the amino acid sequence of the precursor protein of a porcine homologue of the ligand peptide to GPR8.

[SEQ ID NO: 56]
This shows the amino acid sequence of a porcine homologue of the ligand peptide to GPR8 deduced from SEQ ID NO: 55.

[SEQ ID NO: 57]
This shows the amino acid sequence of a porcine homologue of the ligand peptide to GPR8 deduced from SEQ ID NO: 55.

[SEQ ID NO: 58]
This shows the base sequence encoding the amino acid sequence represented by SEQ ID NO: 56.

[SEQ ID NO: 59]
This shows the base sequence encoding the amino acid sequence represented by SEQ ID NO: 57.

[SEQ ID NO: 60]
This shows a synthetic DNA used to acquire cDNA encoding a part of the precursor protein of a rat homologue of the ligand peptide to GPR8.

[SEQ ID NO: 61]
This shows a synthetic DNA used to acquire cDNA encoding a part of the precursor protein of a rat homologue of the ligand peptide to GPR8.

[SEQ ID NO: 62]
This shows the sequence of cDNA encoding a part of the precursor protein of a rat homologue of the ligand peptide to GPR8.

[SEQ ID NO: 63]
This shows a synthetic DNA used to acquire the 5' upstream sequence of cDNA encoding the precursor protein of a rat homologue of the ligand peptide to GPR8.

[SEQ ID NO: 64]
This shows a synthetic DNA used to acquire the 5' upstream sequence of cDNA encoding the precursor protein of a rat homologue of the ligand peptide to GPR8.

[SEQ ID NO: 65]
This shows the 5' upstream DNA sequence of cDNA encoding the precursor protein of a rat homologue of the ligand peptide to GPR8.

[SEQ ID NO: 66]
This shows a synthetic DNA used to acquire the 3' downstream sequence of cDNA encoding the precursor protein of a rat homologue of the ligand peptide to GPR8.

[SEQ ID NO: 67]
This shows a synthetic DNA used to acquire the 3' downstream sequence of cDNA encoding the precursor protein of a rat homologue of the ligand peptide to GPR8.

[SEQ ID NO: 68]
This shows the 3' downstream sequence of cDNA encoding the precursor protein of a rat homologue of the ligand peptide to GPR8.

[SEQ ID NO: 69]
This shows a synthetic DNA used to acquire cDNA encoding the precursor protein of a rat homologue of the ligand peptide to GPR8.

[SEQ ID NO: 70]
This shows a synthetic DNA used to acquire cDNA encoding the precursor protein of a rat homologue of the ligand peptide to GPR8.

[SEQ ID NO: 71]
This shows the sequence of cDNA encoding the precursor protein of a rat homologue of the ligand peptide to GPR8.

[SEQ ID NO: 72]
This shows the amino acid sequence of the precursor protein of a rat homologue of the ligand peptide to GPR8.

[SEQ ID NO: 73]
This shows the amino acid sequence of a rat homologue of the ligand peptide to GPR8 deduced from SEQ ID NO: 72.

[SEQ ID NO: 74]
This shows the amino acid sequence of a rat homologue of the ligand peptide to GPR8 deduced from SEQ ID NO: 72.

[SEQ ID NO: 75]
This shows the base sequence encoding the amino acid sequence represented by SEQ ID NO: 73.

[SEQ ID NO: 76]
This shows the base sequence encoding the amino acid sequence represented by SEQ ID NO: 74.

[SEQ ID NO: 77]
This shows the mouse genome fragment sequence supposed to encode a part of the precursor protein of a mouse homologue of the GPR8 ligand peptide.

[SEQ ID NO: 78]
This shows a synthetic DNA used to screen cDNA encoding a part of the precursor protein of a mouse homologue of the ligand peptide to GPR8.

[SEQ ID NO: 79]
This shows a synthetic DNA used to screen cDNA encoding a part of the precursor protein of a mouse homologue of the ligand peptide to GPR8.

[SEQ ID NO: 80]
This shows the DNA sequence encoding a part of the precursor protein of a human homologue of the ligand peptide to GPR8, amplified from mouse testis-derived cDNA.

[SEQ ID NO: 81]
This shows a synthetic DNA used to acquire the 5' upstream sequence of cDNA encoding the precursor protein of a mouse homologue of the ligand peptide to GPR8.

[SEQ ID NO: 82]
This shows a synthetic DNA used to acquire the 5' upstream sequence of cDNA encoding the precursor protein of a mouse homologue of the ligand peptide to GPR8.

[SEQ ID NO: 83]
This shows the DNA sequence at the 5' upstream side of cDNA encoding the precursor protein of a mouse homologue of the ligand peptide to GPR8.

[SEQ ID NO: 84]
This shows a synthetic DNA used to acquire the 3' downstream sequence of cDNA encoding the precursor protein of a mouse homologue of the ligand peptide to GPR8.

[SEQ ID NO: 85]
This shows a synthetic DNA used to acquire the 3' downstream sequence of cDNA encoding the precursor protein of a mouse homologue of the ligand peptide to GPR8.

[SEQ ID NO: 86]
This shows the DNA sequence at the 3' downstream side of cDNA encoding the precursor protein of a mouse homologue of the ligand peptide to GPR8.

[SEQ ID NO: 87]
This shows a synthetic DNA used to acquire cDNA encoding the precursor protein of a mouse homologue of the ligand peptide to GPR8.

[SEQ ID NO: 88]
This shows a synthetic DNA used to acquire cDNA encoding the precursor protein of a mouse homologue of the ligand peptide to GPR8.

[SEQ ID NO: 89]
This shows the sequence of a cDNA encoding the precursor protein of a mouse homologue of the ligand peptide to GPR8.

[SEQ ID NO: 90]
This shows the amino acid sequence of precursor protein of a mouse homologue of the ligand peptide to GPR8.

[SEQ ID NO: 91]
This shows the amino acid sequence of a mouse homologue of the ligand peptide to GPR8 deduced from SEQ ID NO: 90.

[SEQ ID NO: 92]
This shows the amino acid sequence of a mouse homologue of the ligand peptide to GPR8 deduced from SEQ ID NO: 90.

[SEQ ID NO: 93]
This shows the base sequence encoding the amino acid sequence represented by SEQ ID NO: 91.

[SEQ ID NO: 94]
This shows the base sequence encoding the amino acid sequence represented by SEQ ID NO: 92.

[SEQ ID NO: 95]
This shows the amino acid sequence of human GPR8 ligand (1-23) oxidation product synthesized in REFERENCE EXAMPLE 44 later described.

[SEQ ID NO: 96]
This shows the amino acid sequence of human GPR8 ligand (1-22) synthesized in REFERENCE EXAMPLE 45 later described.

[SEQ ID NO: 97]
This shows the amino acid sequence of human GPR8 ligand (1-21) synthesized in REFERENCE EXAMPLE 46 later described.

[SEQ ID NO: 98]
This shows the amino acid sequence of human GPR8 ligand (1-20) synthesized in REFERENCE EXAMPLE 47 later described.

[SEQ ID NO: 99]
This shows the amino acid sequence of human GPR8 ligand (1-19) synthesized in REFERENCE EXAMPLE 48 later described.

[SEQ ID NO: 100]
This shows the amino acid sequence of human GPR8 ligand (1-18) synthesized in REFERENCE EXAMPLE 49 later described.

[SEQ ID NO: 101]
This shows the amino acid sequence of human GPR8 ligand (1-17) synthesized in REFERENCE EXAMPLE 50 later described.

[SEQ ID NO: 102]
This shows the amino acid sequence of human GPR8 ligand (1-16) synthesized in REFERENCE EXAMPLE 51 later described.

[SEQ ID NO: 103]
This shows the amino acid sequence of porcine GPR8 ligand (1-23) oxidation product synthesized in REFERENCE EXAMPLE 54 later described.

[SEQ ID NO: 104]
This shows the amino acid sequence of rat or mouse GPR8 ligand (1-23) oxidation product synthesized in REFERENCE EXAMPLE 55 later described.

[SEQ ID NO: 105]
This shows the amino acid sequence of human GPR8 ligand (1-23) synthesized in REFERENCE EXAMPLE 12 later described.

[SEQ ID NO: 106]
This shows the amino acid sequence of [$N^{\alpha}$-Acetyl-Trp$^1$]-human GPR8 ligand (1-23) synthesized in REFERENCE EXAMPLE 56 later described.

[SEQ ID NO: 107]
This shows the amino acid sequence of human GPR8 ligand (2-23) synthesized in REFERENCE EXAMPLE 57 later described.

[SEQ ID NO: 108]
This shows the amino acid sequence of human GPR8 ligand (4-23) synthesized in REFERENCE EXAMPLE 58 later described.

[SEQ ID NO: 109]
This shows the amino acid sequence of human GPR8 ligand (9-23) synthesized in REFERENCE EXAMPLE 59 later described.

[SEQ ID NO: 110]
This shows the amino acid sequence of human GPR8 ligand (15-23) synthesized in REFERENCE EXAMPLE 60 later described.

[SEQ ID NO: 111]
This shows the amino acid sequence of [N-Acetyl-Tyr2]-human GPR8 ligand (2-23) synthesized in REFERENCE EXAMPLE 61 later described.

[SEQ ID NO: 112]
This shows the amino acid sequence of [D-Trp$^1$]-human GPR8 ligand (1-23) synthesized in REFERENCE EXAMPLE 62 later described.

[SEQ ID NO: 113]
This shows the amino acid sequence of [N-3-Indolepropanyl-Tyr]-human GPR8 ligand (2-23) synthesized in REFERENCE EXAMPLE 63 later described.

[SEQ ID NO: 114]
This shows the base sequence encoding the amino acid sequence represented by SEQ ID NO: 96.

[SEQ ID NO: 115]
This shows the base sequence encoding the amino acid sequence represented by SEQ ID NO: 97.

[SEQ ID NO: 116]
This shows the base sequence encoding the amino acid sequence represented by SEQ ID NO: 98.

[SEQ ID NO: 117]
This shows the base sequence encoding the amino acid sequence represented by SEQ ID NO: 99.

[SEQ ID NO: 118]
This shows the base sequence encoding the amino acid sequence represented by SEQ ID NO: 100.

[SEQ ID NO: 119]
This shows the base sequence encoding the amino acid sequence represented by SEQ ID NO: 101.

[SEQ ID NO: 120]
This shows the base sequence encoding the amino acid sequence represented by SEQ ID NO: 102.

[SEQ ID NO: 121]
This shows the base sequence encoding the amino acid sequence represented by SEQ ID NO: 107.

[SEQ ID NO: 122]
This shows the base sequence encoding the amino acid sequence represented by SEQ ID NO: 108.

[SEQ ID NO: 123]
This shows the base sequence encoding the amino acid sequence represented by SEQ ID NO: 109.

[SEQ ID NO: 124]
This shows the base sequence encoding the amino acid sequence represented by SEQ ID NO: 110.

[SEQ ID NO: 125]
This shows the base sequence encoding the amino acid sequence represented by SEQ ID NO: 6.

[SEQ ID NO: 126]
This shows a synthetic DNA used for screening of cDNA encoding human GPR7.

[SEQ ID NO: 127]
This shows a synthetic DNA used for screening of cDNA encoding human GPR7.

[SEQ ID NO: 128]
This shows the entire base sequence of human GPR7 protein cDNA, to which the base sequence recognized by restriction enzyme ClaI is added at the 5' end and the base sequence recognized by restriction enzyme SpeI is added at the 3' end.

[SEQ ID NO: 129]
This shows the entire amino acid sequence of human GPR7.

[SEQ ID NO: 130]
This shows the base sequence of DNA used as a primer for amplifying standard human GPR7 DNA.

[SEQ ID NO: 131]
This shows the base sequence of DNA used as a primer for amplifying standard human GPR7 DNA.

[SEQ ID NO: 132]
This shows the sequence of synthetic DNA used as a primer to determine the expression level of GPR7 gene in human GPR7-expressed CHO cells.

[SEQ ID NO: 133]
This shows the sequence of synthetic DNA used as a primer to determine the expression level of GPR7 gene in human GPR7-expressed CHO cells.

[SEQ ID NO: 134]
This shows the sequence of synthetic DNA used as a probe to determine the expression level of GPR7 gene in human GPR7-expressed CHO cells.

[SEQ ID NO: 135]
This shows the amino acid sequence of [Phe$^2$] human GPR8 ligand (1-20).

Transformant *Escherichia coli* DH5α/pAKKO-GPR8, which was obtained in REFERENCE EXAMPLE 3 later described, has been deposited since Feb. 27, 2001 on the Institute for Fermentation (IFO), located at 2-17-85, Juso Honcho, Yodogawa-ku, Osaka-shi, Osaka (zip code 532-8686), under the Accession Number IFO 16564 and since on Apr. 11, 2001 on the National Institute of Advanced Industrial Science and Technology, International Patent Organism Depositary, located at Central 6, 1-1-1 Higashi, Tsukuba, Ibaraki (zip code 305-8566), under the Accession Number FERM BP-7540, respectively.

Transformant *Escherichia coli* TOP10/pCR2.1-TOPO Human GPR8 Ligand Precursor, which was obtained in REFERENCE EXAMPLE 28 later described, has been deposited since Feb. 27, 2001 on the Institute for Fermentation (IFO), located at 2-17-85, Juso Honcho, Yodogawa-ku, Osaka-shi, Osaka (zip code 532-8686), under the Accession Number IFO 16568 and since on Apr. 11, 2001 on the National Institute of Advanced Industrial Science and Technology, International Patent Organism Depositary, located at Central 6, 1-1-1 Higashi, Tsukuba, Ibaraki (zip code 305-8566), under the Accession Number FERM BP-7544, respectively.

Transformant *Escherichia Escherichia coli* TOP10/pCR2.1-TOPO Porcine GPR8 Ligand Precursor, which was obtained in REFERENCE EXAMPLE 32 later described, has been deposited since Feb. 27, 2001 on the Institute for Fermentation (IFO), located at 2-17-85, Juso Honcho, Yodogawa-ku, Osaka-shi, Osaka (zip code 532-8686), under the Accession Number IFO 16565 and since on Apr. 11, 2001 on the National Institute of Advanced Industrial Science and Technology, International Patent Organism Depositary, located at Central 6, 1-1-1 Higashi, Tsukuba, Ibaraki (zip code 305-8566), under the Accession Number FERM BP-7541, respectively.

Transformant *Escherichia coli* TOP10/pCR2.1-TOPO Rat GPR8 Ligand Precursor, which was obtained in REFERENCE EXAMPLE 36 later described, has been deposited since Feb. 27, 2001 on the Institute for Fermentation (IFO), located at 2-17-85, Juso Honcho, Yodogawa-ku, Osaka-shi, Osaka (zip code 532-8686), under the Accession Number IFO 16567 and since on Apr. 11, 2001 on the National Institute of Advanced Industrial Science and Technology, International Patent Organism Depositary, located at Central 6, 1-1-1 Higashi, Tsukuba, Ibaraki (zip code 305-8566), under the Accession Number FERM BP-7543, respectively.

Transformant *Escherichia coli* TOP10/pCR2.1-TOPO Mouse GPR8 Ligand Precursor, which was obtained in REFERENCE EXAMPLE 41 later described, has been deposited since Feb. 27, 2001 on the Institute for Fermentation (IFO), located at 2-17-85, Juso Honcho, Yodogawa-ku, Osaka-shi, Osaka (zip code 532-8686), under the Accession Number IFO 16566 and since on Apr. 11, 2001 on the National Institute of Advanced Industrial Science and Technology, International Patent Organism Depositary, located at Central 6, 1-1-1 Higashi, Tsukuba, Ibaraki (zip code 305-8566), under the Accession Number FERM BP-7542, respectively.

EXAMPLES

The present invention will be described in more detail below, with reference to REFERENCE EXAMPLES and EXAMPLES, but is not deemed to limit the scope of the present invention thereto.

Reference Example 1

Amplification of Human GPR8 cDNA by PCR Using Human Brain-derived cDNA

Reverse transcription was performed by using random primers, in which human brain-derived poly(A) $^+$RNA (Clontech Laboratories, Inc.) was used as a template. TaKaRa RNA PCR ver. 2.1 Kit was used for the reverse transcription. Next, amplification was carried out by PCR, in which the resulting reverse transcription product was used as a template and synthetic primers represented by SEQ ID NO: 1 and SEQ ID NO: 2 were used. The synthetic primers were constructed so as to amplify the gene in the region to be translated to its receptor protein was amplified, in which the recognition sequences of restriction enzymes were added to the 5' and 3' ends, respectively, so that the base sequences recognized by restriction enzymes ClaI and SpeI were added to the gene at the 5' and 3' ends, respectively. The reaction solution was composed of 5 µl of cDNA template, 0.4 µM each of the synthetic DNA primers, 0.8 mM dNTPs and 0.5 µl of pfu polymerase (Stratagene), to which buffer attached to the enzyme was added to make the total volume 50 µl. For amplification, after heating at 94° C. for 60 seconds, one cycle set to include 94° C. for 60 seconds, 65° C. for 60 seconds and 72° C. for 150 seconds was repeated 35 times, using Thermal Cycler (PE Biosystems). The amplified product was confirmed by 0.8% agarose gel electrophoresis followed by staining with ethidium bromide.

Reference Example 2

Subcloning of the PCR Product to Plasmid Vector and Confirmation of the Amplified cDNA Sequence by Decoding the Base Sequence of the Inserted cDNA Region The reaction solution obtained by PCR in REFERENCE EXAMPLE 1 was subjected to 0.8% low melting agarose gel electrophoresis for separation. The band parts were excised from the gel with a razor blade and ground to small pieces, which were then extracted with phenol/chloroform and precipitated in ethanol to recover the DNA. According to the protocol attached to PCR-Script™ Amp SK(+) Cloning Kit (Stratagene), the recovered DNAs were subcloned into the plasmid vector, pCR-Script™ Amp SK(+). The recombinant vectors were introduced into *Escherichia coli* DH5α competent cells (Toyobo Co., Ltd.) to produce transformants. Then, clones having a cDNA-inserted fragment were selected in an LB agar culture medium containing ampicillin, IPTG and X-gal. Only clones exhibiting white color were picked with a sterilized toothpick to acquire transformant *Escherichia coli* DH5α/GPR8. The individual clones were cultured overnight in an LB culture medium containing ampicillin, and plasmid DNAs were prepared using QIAwell 8 Plasmid Kit (Qiagen). An aliquot of the DNAs thus prepared was digested with restriction enzymes ClaI and SpeI to confirm the size of the receptor cDNA fragment inserted. Sequencing was carried out by using a DyeDeoxy Terminator Cycle Sequencing Kit (PE Biosystems), and the DNAs were decoded by using a fluorescent automatic sequencer (SEQ ID NO: 3). FIG. 1 shows the entire base sequence of human GPR8 receptor protein cDNA (SEQ ID NO: 23) and the entire amino acid sequence of human GPR8 receptor protein cDNA (SEQ ID NO: 4) translated therefrom.

Reference Example 3

Preparation of CHO Cells Which Express GPR8

Using Plasmid Midi Kit (Qiagen), plasmid DNA was prepared from the *Escherichia coli* clones transformed by the plasmid bearing the gene encoding the full-length amino acid sequence of human brain-derived GPR8, which sequence was confirmed in REFERENCE EXAMPLE 2, having the ClaI and SpeI recognition sequences added at the 5' and 3' ends, respectively. The plasmid DNA was digested with restriction enzymes ClaI and SpeI to excise the insert DNA. The insert DNA was electrophoresed, excised from the agarose gel with a razor blade, ground into small pieces, then extracted with phenol and with phenol/chloroform, and precipitated in ethanol to recover the DNA. The insert DNA was added to the animal cell expression vector plasmid pAKKO-111H (the same vector plasmid as pAKKO1.11H described in Hinuma, S., et al., Biochim. Biophys. Acta, 1219, 251-259, 1994), which was digested with ClaI and SpeI, followed by ligation using T4 ligase (Takara Shuzo Co., Ltd.) to construct a receptor protein expression plasmid pAKKO-GPR8. *Escherichia coli* transformed by this plasmid pAKKO-GPR8 was named *Escherichia coli* DH5α/pAKKO-GPR8.

*Escherichia coli* DH5α (Toyobo Co., Ltd.) transfected with pAKKO-GPR8 was cultured and the pAKKO-GPR8 µlasmid DNA was prepared using Plasmid Midi Kit (Qiagen). Using CellPhect Transfection Kit (Amersham Pharmacia Biotech), the plasmid DNA was transfected to CHO dhfr$^-$ cells in accordance with the protocol attached. DNA, 4.5 µg, was co-precipitated with calcium phosphate in suspension. The resulting suspension was added to a 6 cm-diameter Petri dish, in which 5×10$^5$ or 1×10$^6$ CHO dhfr$^-$ cells had been seeded before 24 hours. The cells were cultured in MEMα medium containing 10% fetal calf serum for one day. After passage, the cells were cultured in nucleic acid-free MEMα selection medium containing 10% dialyzed fetal calf serum, 47 clones of the transformant colony GPR8-expressed CHO cells, growing in the selection medium, were selected.

Reference Example 4

Selection of the CHO/GPR8 Cell Line with High Expression of the Full-length Human GPR8 Protein mRNA The expression level of the full-length GPR8 protein mRNAs of 47 clones from the CHO/GPR8 cell line established in REFERENCE EXAMPLE 3 was determined as follows, using Cytostar T Plate (Amersham Pharmacia Biotech) in accordance with the protocol attached. Each clone of the CHO/GPR8 cell line was inoculated on Cytostar T Plate in 2.5×10$^4$ cells/well. After culturing for 24 hours, the cells were fixed with 10% formalin. To each well 0.25% Triton. X-100 was added to increase cell permeability, $^{35}$S-labeled riboprobe of SEQ ID NO: 0.5 was added to the cells for hybridization. Free riboprobe was digested by adding 20 µg/ml RNase A to each well. After the plate was thoroughly washed, radioactivity of the hybridized riboprobe was assayed with Topcounter. The cell line with a high radioactivity provides a high mRNA expression level. Three clones (#17, #41 and #46), which showed a high mRNA expression level, were used for the following experiment, especially clone #17 as a main clone.

Reference Example 5

Determination of the Intracellular cAMP Level Using GPR8-expressed CHO Cells

The CHL/GPR8 cells produced in REFERENCE EXAMPLE 4 and mock CHO cells were inoculated on a 24-well plate in $5 \times 10^4$ cells/well, followed by cultivation for 48 hours. The cells were washed with Hanks' buffer (pH 7.4) containing 0.2 mM 3-isobutyl-methylxanthine, 0.05% BSA and 20 mM HEPES (hereinafter Hanks' buffer (pH 7.4) containing 0.2 mM 3-isobutyl-methylxanthine, 0.05% BSA and 20 mM HEPES is referred to as a reaction buffer). Thereafter, 0.5 ml of the reaction buffer was added to the system, which was kept warm in an incubator for 30 minutes. After the reaction buffer was removed, 0.25 ml of a fresh reaction buffer was added to the cells. Then, 0.25 ml of the reaction buffer containing a sample fluid and 2 µM forskolin was added to the cells followed by reacting at 37° C. for 24 minutes. By adding 100 µl of 20% perchloric acid, the reaction was terminated. The reaction mixture was then allowed to stand on ice for an hour to extract intracellular cAMP. The amount of cAMP in the extract was measured using cAMP EIA kit (Amersham Pharmacia Biotech).

Reference Example 6

Assay for GTPγ S Binding Activity Using the GPR8-expressed CHO Cell Membrane Fraction The [$^{35}$S]-guanosine 5'-(γ-thio)triphosphate binding promoting activity on a GPR8-expressed CHO cell membrane fraction was assayed by the following procedures. First, preparation of the membrane fraction is described. To $1 \times 10^8$ of CHO/GPR8 cells was added 10 ml of a homogenate buffer (10 mM NaHCO$_3$, 5 mM EDTA, 0.5 mM PMSF, 1 µg/ml pepstatin, 4 µg/ml E64 and 20 µg/ml leupeptin). The mixture was homogenized by using Polytron (12,000 rpm, 1 min.). The cell homogenate was subjected to centrifugation (1,000 g, 15 mins.) to obtain the supernatant. Next, the supernatant was subjected to ultracentrifugation (Beckman type 30 rotor, 30,000 rpm, 1 hour). The resulting precipitate was used as GPR8-expressed CHO cell membrane fraction.

The GTPγ S binding activity was assayed as follows. The GPR8expressed CHO cell membrane fraction was diluted with a membrane dilution buffer (50 mM Tris-hydrochloride buffer (pH 7.4), 5 mM MgCl$_2$, 150 mM NaCl, 1 µM GDP) to prepare a cell membrane fraction solution for assay having a protein level of 30 mg/ml. To 200 µl of the cell membrane fraction solution for assay were added 2 µl of 51.5 nM [$^{35}$S]-guanosine 5'-(γ-thio)triphosphate (NEN Co.) and a sample fluid. The resulting solution mixture was kept at 25° C. for an hour. The mixture was filtrated through a filter. After washing twice with 1.5 ml of a wash buffer (50 mM Tris-hydrochloride buffer (pH 7.4), 5 mM MgCl$_2$, 1 mM EDTA, 0.1% BSA), radioactivity of the filter was measured with a liquid scintillation counter.

Reference Example 7

Detection of the cAMP Production Suppressing and GTPγ S Binding Promoting Activity Contained in Porcine Hypothalamus Extract Specific to CHO/GPR8 Cell Line High performance liquid chromatography (HPLC) fractions of the porcine hypothalamus extract were prepared by the following procedures. Porcine hypothalamus, 500 g (corresponding to 30 µlgs), which had been purchased from Tokyo Shibaura Zoki Co. and kept under ice cooling after the hypothalamus was withdrawn from porcine on the day of their sacrifice, was minced, immediately put into 2.0 liters of boiling distilled water and boiled for 10 minutes. Immediately after the boiling, the minced product was ice-cooled and 120 ml of acetic acid was added to the homogenate to make the final concentration 1.0 M. Using Polytron (20,000 rpm, 6 mins.), the mixture was homogenized. The homogenate was centrifuged (8,000 rpm, 30 mins.) and the supernatant was taken out. After 2.0 liters of 1.0 M acetic acid was added to the precipitate, the mixture was again homogenized using Polytron. The homogenate was stirred overnight and then centrifuged (8,000 rpm, 30 mins.) to obtain the supernatant. After 2-fold volume of chilled acetone was dropwise added slowly to the supernatant at 4° C., the supernatant obtained by the first centrifugation was stirred overnight and, the supernatant obtained by the second centrifugation was stirred for 4 hours. The acetone-added extract was centrifuged (8,000 rpm, 30 mins.) to remove the precipitate and acetone was evaporated off in vacuum from the supernatant, using an evaporator. An equal volume of diethyl ether was added to the acetone-free extract, the ethereal layer containing lipids was separated using a separating funnel to recover the aqueous layer. After the lipids were removed with ether, the extract was concentrated in vacuum using an evaporator to completely remove the ether. The concentrate was filtrated through a glass fiber filter paper (Advantech, DP70 (90 mmφ) and the filtrate was charged in a glass column (30φ×240 mm) packed with C18 column (YMC, YMCgel ODS-AM 120-S50). After washing with 400 ml of 1.0 M acetic acid, the column was eluted with 500 ml of 60% acetonitrile containing 0.1% trifluoroacetic acid. The eluate was concentrated in vacuum, the solvent was distilled off and then the concentrate was lyophilized. About 0.5 g of the lyophilized product was dissolved in 30 ml of 10% acetonitrile containing 0.1% trifluoroacetic acid. An aliquot of 10 ml each was subjected to HPLC on 10% to 60% acetonitrile containing 0.1% trifluoroacetic acid by density gradient elution using C18 column (Toso, TSKgel ODS-80™ (21.5φ×300 mm)). HPLC was performed three times. The eluate was fractionated into 60 fractions and the eluates in three runs were collected. Each fraction was concentrated and evaporated to dryness in vacuum. The residue was dissolved in 0.5 ml of dimethylsulfoxide (DMSO).

A DMSO solution of the HPLC fraction obtained as described above was added to the CHL/GPR8 cells by the procedures shown in REFERENCE EXAMPLE to determine the level of cAMP produced in the cells. As a result, a marked activity of suppressing cAMP product was noted in fraction #30. Also, the GTPγ S binding promoting activity was examined on a similar sample fluid using the GPR8-expressed CHO cells. Likewise, a marked activity was confirmed around fraction #30. Since these activities were not observed in other receptor expression cells, the results reveal that a ligand active substance specific to GPR8 was present in the porcine hypothalamus extract.

Reference Example 8

Inactivation of the Active Substance Showing the Intracellular cAMP Production Suppressing Activity Specific to GPR8-expressed CHO Cells in Porcine Hypothalamus Extract The HPLC fraction #30 which showed the intracellular cAMP production suppressing activity on the GPR8-expressed CHO cells in REFERENCE EXAMPLE 7 was treated with a proteolytic enzyme, pronase (Sigma, protease Type XIV (P5147)) to examine if the active substance is proteinaceous.

The HPLC fraction (#30), 2 μl, from the hypothalamus extract described above was added to 200 μl of 0.2 M ammonium acetate and 3 μl of pronase was further added thereto. After incubation at 37° C. for 2 hours, the culture was boiled in boiling water for 10 minutes to inactivate the pronase. To the reaction solution was added 2 ml of distilled water containing 0.05 mg of BSA and 0.05 mg of CHAPS, followed by lyophilization. In order to examine if pronase itself, or heating and lyophilization have an effect, pronase alone, the HPLC fraction alone, and a mixture of the HPLC fraction with pronase alone after its heating were treated in a similar manner and then lyophilized. Each sample fluid lyophilized was added to the GPR8-expressed CHO cells by the procedures shown in REFERENCE EXAMPLE 5 and the intracellular cAMP production suppressing activity was assayed. Since the active substance showing the intracellular cAMP production suppressing activity on the GPR8-expressed CHO cells in the porcine hypothalamus extract was completely inactivated by the pronase, it was revealed that this substance was a protein or peptide.

Reference Example 9

Purification of the Active Substance Showing the GTPγ S Binding Promoting Activity Specific to the GPR8-Expressed CHO Cell Membrane Fraction from Porcine Hypothalamus A representative example of purifying from porcine hypothalamus the active substance showing a ligand activity specific to GPR8 using the GTPγ S binding promoting activity on the GPR8-expressed CHO cell membrane fraction as an indicator is described below in a specific manner. Porcine hypothalamus, 500 g (corresponding to 30 pgs) was extracted with 1.0 M acetic acid by the same procedures as described in REFERENCE EXAMPLE 7. After precipitation and removal of lipids with ether, the extract was adsorbed to a column packed with C18 (YMC, YMCgel ODS-AM 120-S50) followed by elution with 60% acetonitrile containing 0.1% trifluoroacetic acid. After the eluate was concentrated and iyophilized, the concentrate was subjected to HPLC using C18 column (Toso, TSKgel ODS-80TS (21.5φ×300 mm)) to obtain the active fraction. The activity was recovered in fraction #30, which was further purified by the following procedures.

The fraction was dissolved in 10 ml of 10 mM ammonium formate containing 10% acetonitrile. After the solution was passed through a cationic exchange column (Toso, TSKgel SP-5PW (20 mmφ×150 mm)), the column was eluted with 10 mM to 2.0 M ammonium formate containing 10% acetonitrile by means of density gradient. The activity was recovered at about 0.8M ammonium formate. The active fraction was lyophilized and dissolved in 1.0 ml of 10% acetonitrile containing 0.1% trifluoroacetic acid. After the solution was passed through a CN column (Nomura Chemical Co., Ltd., Develosil CN-UG-5 (4.6 mmφ×250 mm)), elution was performed by density gradient with 21% to 26% acetonitrile containing 0.1% trifluoroacetic acid. The activity appeared around 22.1% acetonitrile. The active fraction was lyophilized and dissolved in 0.1 ml of DMSO. The solution was further added with 0.4 ml of 10% acetonitrile containing 0.1% trifluoroacetic acid, which was passed through an ODS column (Wako Pure Chemical Industries, Co., Ltd., Wakosil-II 3C18HG (2.0 mmφ×150 mm)) followed by elution in terms of density gradient of 22.5% to 32.5% acetonitrile containing 0.1% trifluoroacetic acid. The activity appeared as a single peak around 26.5% acetonitrile (FIG. 2).

Reference Example 10

Amino-Terminal Amino Acid Sequencing of the Active Substance Showing the GTPγ S Binding Promoting Activity Specific to the GPR8-expressed CHO Cells Purified from Porcine Hypothalamus and EST Sequence Predicted to Encode a Part of Human and Rat Homologue Peptide Precursor Proteins of GPR8 Ligand Amino-terminal amino acid sequencing of the active substance showing the GTPγ S binding promoting activity specific to the GPR8-expressed CHO cell membrane fraction purified in REFERENCE EXAMPLE 9 was performed. Since it was speculated that the active substance would be a protein or peptide as demonstrated in REFERENCE EXAMPLE 8, amino-terminal amino acid sequencing was conducted by use of Procise 494 Protein Sequencer available from Perkin-elmer, using the eluate containing the active peak. As a result, the sequence represented by SEQ. ID: 6 was obtained in the region up to 17 residues from the amino terminus. This sequence was considered to be a part of the ligand peptide.

Survey of gene database based on this sequence gave some EST (Expressed Sequence Tag) sequences, and it is supposed that the sequence or its complementary strand would encode a part of the precursor protein of this peptide. These sequences have the following accession numbers, cDNA origin, sequence size and sequence identification numbers: AW007531 (anaplastic oligodentroglioma, 438 bases, SEQ ID NO: 7), AI500303 (anaplastic oligodentroglioma, 264 bases, SEQ ID NO: 8), AI990964 (colonic mucosa from patient of Crohn's disease, 424 bases, SEQ ID NO: 9), AA744804 (germinal center B cell, 375 bases, SEQ ID NO: 10), H31598 (PC12 cells, 260 bases, SEQ. ID NO: 11). The first 4 sequences are derived from human and the last sequence is derived from rat. The DNA sequences of these ESTs extremely well coincided with the region encoding the amino acid sequence corresponding to the sequence of the active peptide isolated from porcine hypothalamus. Furthermore, the translated amino acid sequence was almost identical with the sequence of peptide isolated and clarified from porcine hypothalamus, except that the 5th residue Thr is Val. Based on the foregoing, it was deduced that these ESTs would encode a part of human and rat homologue precursor proteins of the ligand peptide to GPR8.

Reference Example 11

Amplification of Human cDNA Encoding a Part of GPR8 Ligand Peptide Precursor and Decoding of the Amplified cDNA Sequence Based on the putative EST sequences to encode a part of precursor protein of the GPR8 ligand peptide described in REFERENCE EXAMPLE 10, primers were designed and cDNA encoding a part of GPR8 ligand peptide precursor was amplified from human brain-derived cDNA by PCR.

Reverse transcription was performed by using random primers, in which human brain-derived poly(A) +RNA (Clontech Laboratories, Inc.) was used as a template. Rever-Tra Ace (Toyobo Co., Ltd.) was used for the reverse transcription. Next, amplification was carried out by PCR using synthetic primers represented by SEQ ID NO: 12 and SEQ ID NO: 13 designed on the basis of the EST sequences described in REFERENCE EXAMPLE 10. The reaction solution was composed of 2 µl of cDNA template, 0.5 µM each of the synthetic DNA primers, 1.6 mM dNTPs and 0.2 µl of LA Taq (Takara Shuzo Co., Ltd.), to which buffer attached to the enzyme was added to make the total volume 20 µl. For amplification, after heating at 96° C. for 120 seconds using Thermal Cycler (PE Biosystems), one cycle set to include 96° C. for 30 seconds and 72° C. for 45 seconds was repeated 4 times, one cycle set to include 96° C. for 30 seconds and 70° C. for 45 seconds was repeated 4 times, one cycle set to include 96° C. for 30 seconds and 68° C. for 45 seconds was repeated 4 times, one cycle set to include 96° C. for 30 seconds, 64° C. for 30 seconds and 72° C. for 45 seconds was repeated 5 times, one cycle set to include 96° C. for 30 seconds, 60° C. for 30; seconds and 72° C. for 45 seconds was repeated 20 times, and finally, the mixture was kept at 72° C. for 10 minutes. The amplified product was confirmed by 3% agarose gel electrophoresis followed by staining with ethidium bromide.

The PCR solution was subjected to 3% low melting agarose gel electrophoresis for separation. After the band parts were excised from the gel with a razor blade, DNA was recovered using QIAquick Gel Extraction Kit (Qiagen). The recovered DNA was subcloned to plasmid vector pCR2.1-TOPO in accordance with the protocol of TOPO TA Cloning Kit (Invitrogen), which was then introduced to *Escherichia coli* TOP10 (Invitrogen) for transfection. Then, clones having a cDNA-inserted fragment were selected in an LB agar culture medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for determining base sequence was carried out by using a DyeDeoxy Terminator Cycle Sequence Kit (PE Biosystems), and the DNAs were decoded using a fluorescent automatic sequencer to obtain the DNA sequence represented by SEQ ID NO: 14. As predicted, the peptide sequence corresponding to the active peptide, which was isolated from porcine hypothalamus and clarified in its sequence, was present in a part (SEQ ID NO: 15) of the GPR8 ligand peptide precursor protein translated from the aforesaid sequence. In the C terminus, the Arg-Arg sequence (Seidah, N. G. et al., Ann. N.Y. Acad. Sci., 839, 9-24, 1998) was present at 2 sites, from which sequence a normal physiologically active peptide was considered to be excised. In view of the foregoing, it was deduced that the amino acid sequence of a human homologue of the GPR8 ligand peptide would be either SEQ ID NO: 16 or 17 or both.

Reference Example 12

Production of Fmoc-Human GPR8 Ligand (1-23): Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 105) and Human GPR8 Ligand (1-23): Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 16)

Using as a starting material 0.25 mmol (0.76 mmol/g) of Fmoc-Leu-O-Clt resin obtained by introducing Fmoc-Leu into commercially available 2-chlorotrityl resin (Clt resin, 1.33 mmol/g) and using a peptide synthesizer AMI 433A, condensation was performed by the Fmoc/DCC/HOBt method sequentially in the order of Fmoc-Gly, Fmoc-Met, Fmoc-Leu, Fmoc-Leu, Fmoc-Gly, Fmoc-Ala, Fmoc-Ala, Fmoc-Arg (Pbf), Fmoc-Gly, Fmoc-Val, Fmoc-Thr (Bu$^t$), Fmoc-His (Trt), Fmoc-Tyr (Bu$^t$), Fmoc-Arg (Pbf), Fmoc-Pro, Fmoc-Ser (Bu$^t$), Fmoc-Ala, Fmoc-Val, Fmoc-His (Trt), Fmoc-Lys (Boc), Fmoc-Tyr (Bu$^t$) and Fmoc-Trp (Boc) to obtain 830 mg of Fmoc-Trp (Boc)-Tyr (Bu$^t$)-Lys (Boc)-His (Trt)-Val-Ala-Ser (Bu$^t$)-Pro-Arg (Pbf)-Tyr (Bu$^t$)-His (Trt)-Thr (Bu$^t$)-Val-Gly-Arg (Pbf)-Ala-Ala-Gly-Leu-Leu-Met-Gly-Leu-O-Clt (SEQ ID NO: 139) resin. To 150 mg of this resin, 5 ml of TFA/thioanisole/m-cresol/triisopropylsilane/ethanedithiol (85/5/5/2.5/2/5) was added. After the mixture was shaken at room temperature for 2 hours, the resin was filtered off and the solvent was concentrated. Ether was added to the concentrate to obtain crude Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 105) as precipitates. The crude product was subjected to linear density gradient elution (60 mins.) using eluant A: 0.1% TFA-water and eluant B: 0.1% TFA-containing acetonitrile in A/B: 72/28 to 52/48 on preparative HPLC using YMC D-ODS-5-ST S-5 120A column (20×150 mm). Fractions containing the product were collected and lyophilized to obtain 9.7 mg of white powders.

Mass spectrum (M+H)$^+$ 2805.7 (calcd. 2805.4)

Elution time on HPLC 25.1 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with solutions A/B=100/0 to 30/70 (35 mins.)

Flow rate: 1.0 ml/min.

To 5 mg of the thus obtained Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu, (SEQ ID NO: 105), 1 mL of 20% diethylamine/DMF was added, and the mixture was stirred at room temperature for 2 hours. After the solvent was removed by distillation, the residue was subjected to linear density gradient elution (60 mins.) with eluant A: 0.1% TFA-water and eluant B: 0.1% TFA-containing acetonitrile in A/B: 74/26 to 64/36 on preparative HPLC using YMC D-ODS-5-ST S-5 120A column (20×150 mm). Fractions containing the product were collected and lyophilized to obtain 1.2 mg of white powders.

Mass spectrum (M+H)$^+$ 2583.6 (calcd. 2583.4)

Elution time on HPLC 20.4 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with solutions A/B=100/0 to 30/70 (35 mins.)

Flow rate: 1.0 m/min.

Reference Example 13

Production of Human GPR8 Ligand (1-30): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu-Trp (SEQ ID NO: 17)

Using as a starting material 0.25 mmol (0.64 mmol/g) of Fmoc-Trp (Boc)-O-Clt resin obtained by introducing Fmoc- Trp (Boc) into commercially available 2-chlorotrityl resin (Clt resin, 1.33 mmol/g), amino acids were condensed in their sequence order as in REFERENCE EXAMPLE 12, and the Fmoc group was removed on the resin after introducing the final Trp and before excising from the resin. By treatment with TFA/thioanisole/m-cresol/triisopropylsilane/ethanedithiol (85/5/5/2.5/2.5), excision from the resin and removal of side chain protective groups were effected at the same time. The crude peptide was purified as in REFERENCE EXAMPLE 12 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Ser-Pro-Tyr-Leu-Trp (SEQ ID NO: 17).

Mass spectrum (M+H)$^+$ 3543.4 (calcd. 3544.2)

Elution time on HPLC 21.5 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with solutions A/B=100/0 to 30/70 (35 mins.)

Flow rate: 1.0 ml/min.

Reference Example 14

Production of Human GPR8 Ligand (1-29): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu (SEQ ID NO: 20)

Using the resin of REFERENCE EXAMPLE 12, amino acids were condensed in the order of their sequences as in REFERENCE EXAMPLE 13, and excision from the resin and purification were performed to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu (SEQ ID NO: 20).

Reference Example 15

Production of Human GPR8 Ligand (1-28): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu (SEQ ID NO: 21)

After Fmoc-Tyr (Bu$^t$) was introduced into commercially available 2-chlorotrityl resin (Clt resin, 1.33 mmol/g), condensation of amino acids in their sequence order, excision from the resin and purification were carried out as in REFERENCE EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr (SEQ ID NO: 21).

Reference Example 16

Production of Human GPR8 Ligand (1-27): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro (SEQ ID NO: 22)

After Fmoc-Pro was introduced into commercially available 2-chlorotrityl resin (Clt resin, 1.33 mmol/g), condensation of amino acids in their sequence order, excision from the resin and purification were carried out as in REFERENCE EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro (SEQ ID NO: 22).

Reference Example 17

Production of Human GPR8 Ligand (1-26): Tyr-His-Thr-Val-Gly-Arg-Ala-Ala-Gly-Leu-Leu-Met-Gly-Leu-Arg-Arg-Ser (SEQ ID NO: 23)

After Fmoc-Tyr (Bu$^t$) was introduced into commercially available 2-chlorotrityl resin (Clt resin, 1.33 mmol/g), condensation of amino acids in their sequence order, excision from the resin and purification were carried out as in REFERENCE EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser (SEQ ID NO: 23).

Reference Example 18

Production of Human GPR8 Ligand (1-25): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg (SEQ ID NO: 24)

After Fmoc-Arg (Pbf) was introduced into commercially available 2-chlorotrityl resin (Clt resin, 1.33 mmol/g), condensation of amino acids in their sequence order, excision from the resin and purification were carried out as in REFERENCE EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg (SEQ ID NO: 24).

Reference Example 19

Production of Human GPR8 Ligand (1-24): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg (SEQ ID NO: 25)

After Fmoc-Arg (Pbf) was introduced into commercially available 2-chlorotrityl resin (Clt resin, 1.33 mmol/g), condensation of amino acids in their sequence order, excision from the resin and purification were carried out as in REFERENCE EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg (SEQ ID NO: 25).

Reference Example 20

Figure 3:
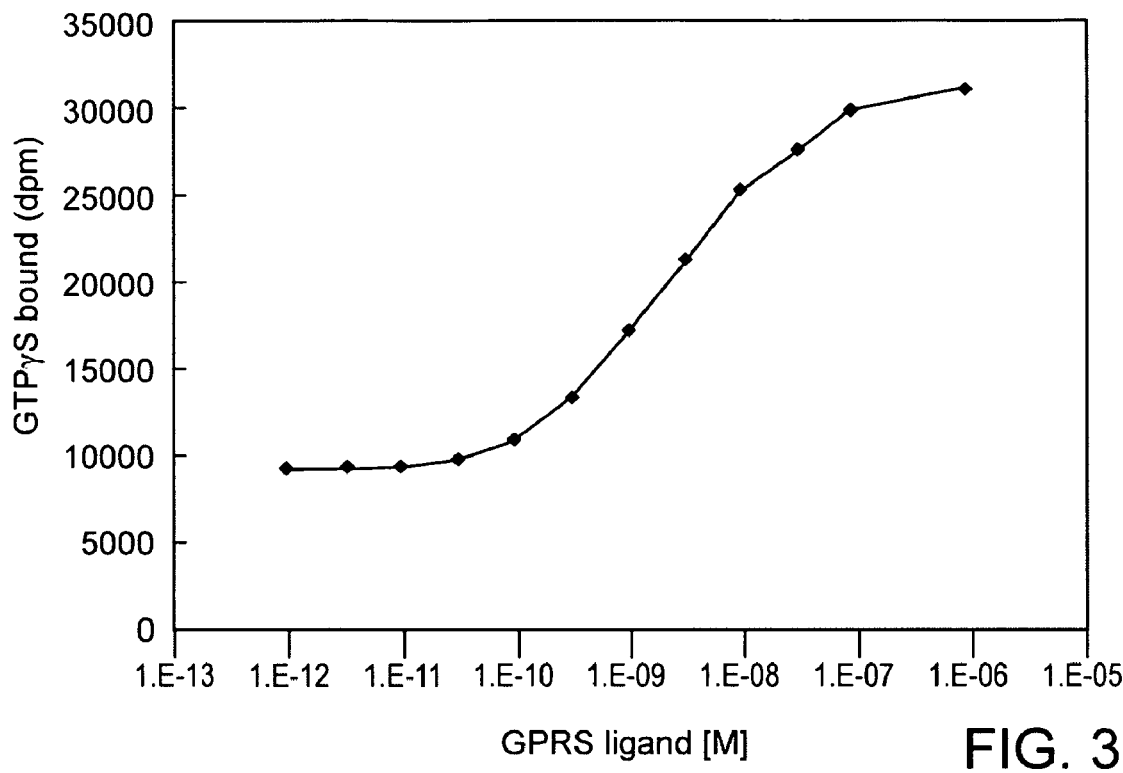
FIG. 3 shows the GTPγ S binding promoting activity of a human homologue GPR8 ligand peptide composed of 23 residues in various concentrations on the CHO/GPR8 cell membrane fraction.

GTPγ S Binding Promoting Activity of Human Homologue of the GPR8 Ligand Peptide Composed of 23 residues. When measured using GPR8-expressed CHO Cell Membrane Fraction The human homologue of GPR8 ligand peptide composed of 23 residues, which was synthesized in REFERENCE EXAMPLE 12 (hereinafter sometimes referred to as hGPR8L (1-23)) was added to the GPR8-expressed CHO cell membrane fraction in various concentrations according to the procedures described in REFERENCE EXAMPLE 6 to assay the GTPγ S binding promoting activity. The results are shown in FIG. 3. Obviously, hGPR8L (1-23) dose-dependently The results revealed that the peptide having a structure of SEQ ID) NO: 16 is a ligand to GPR8.

Reference Example 21

Figure 4:
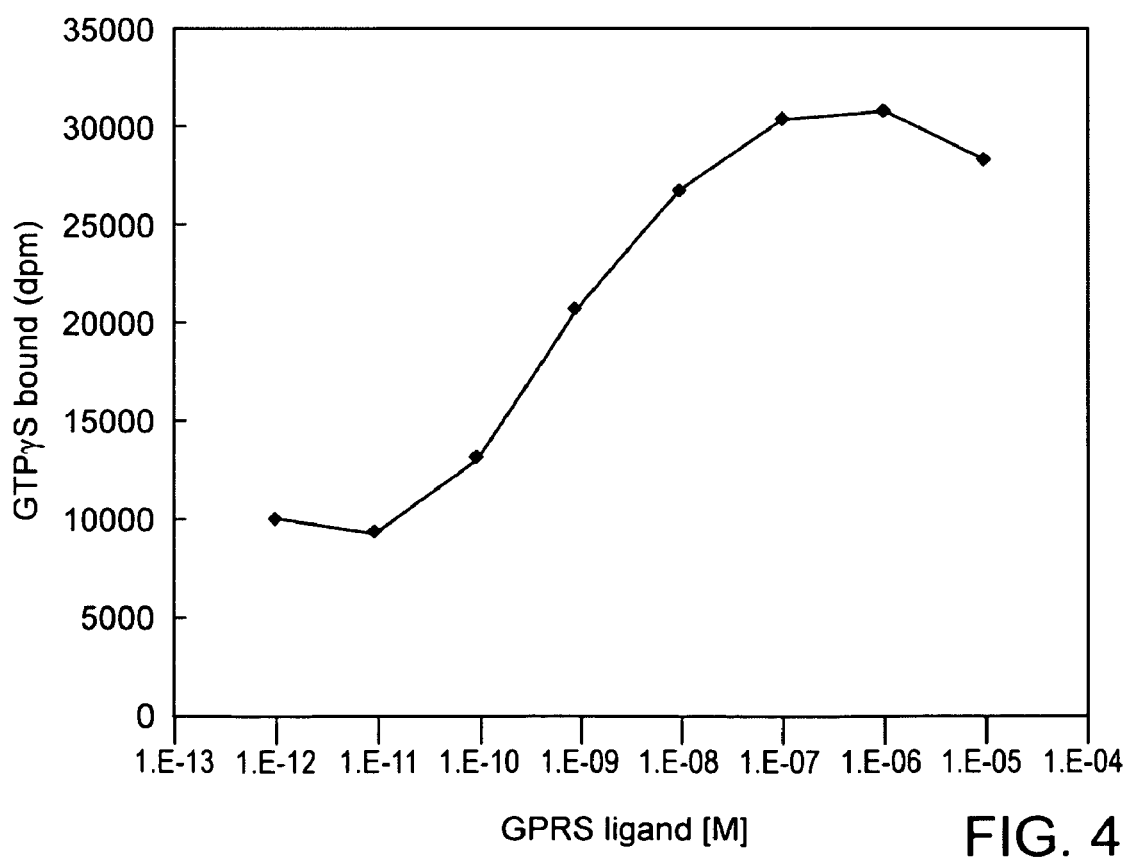
FIG. 4 shows the GTPγ S binding promoting activity of a human homologue GPR8 ligand peptide composed of 30 residues in various concentrations on the CHO/GPR8 cell membrane fraction.

GTPγ S Binding Promoting Activity of Human Homologue of the GPR8 Ligand Peptide Composed of 30 Residues When Measured Using GPR8-expressed CHO Cell Membrane Fraction The human homologue of GPR8 ligand peptide composed of 30 residues, which was synthesized in REFERENCE EXAMPLE 13 (hereinafter sometimes referred to as hGPR8L (1-30)) was added to the GPR8-expressed CHO cell membrane fraction in various concentrations according to the procedures described in REFERENCE EXAMPLE 6 to assay the GTPγ S binding promoting activity. The results are shown in FIG. 4. Obviously, hGPR8L (1-30) dose-dependently promoted the GTPγ S binding of GPR8-expressed CHO cell membrane fraction. The results revealed that the peptide having a structure of SEQ ID NO: 17 is a ligand to GPR8.

Reference Example 22

Figure 5:
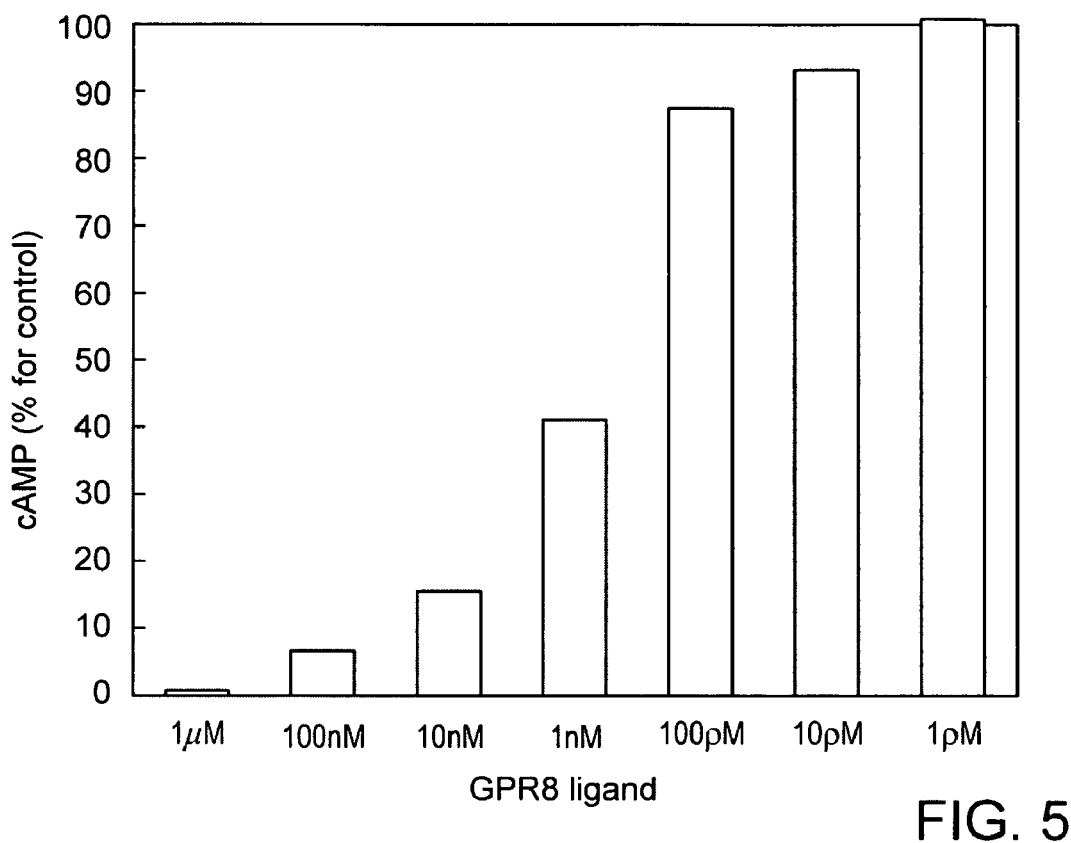
FIG. 5 shows the cAMP production suppressing activity of GPR8 ligand peptide composed of 23 residues in various concentrations on human homologue CHO/GPR8 cells.

Intracellular cAMP Production Suppressing Activity of Human Homologue of the GPR8 Ligand Peptide Composed of 23 Residues When Measured Using GPR8-expressed CHO Cells hGPR8L (1-23), which was synthesized in REFERENCE EXAMPLE 12, was brought in contact with the GPR8-expressed CHO cells in various concentrations according to the procedures described in REFERENCE EXAMPLE 5, to assay the intracellular cAMP production suppressing activity. The results are shown in FIG. 5. Obviously, hGPR8L (1-23) suppressed the intracellular cAMP production dose-dependently in the GPR8-expressed CHO cells. In the figure, the cAMP synthesis suppressing activity is expressed by the value in terms of %, which is obtained when the intracellular cAMP level added with a reaction buffer is subtracted from the intracellular cAMP level when hGPR8L (1-23) is added, wherein the intracellular cAMP level obtained by subtracting the intracellular cAMP level added with a reaction buffer from the intracellular cAMP level added with a forskolin-containing reaction buffer is made 100%.

Reference Example 23

Figure 7:
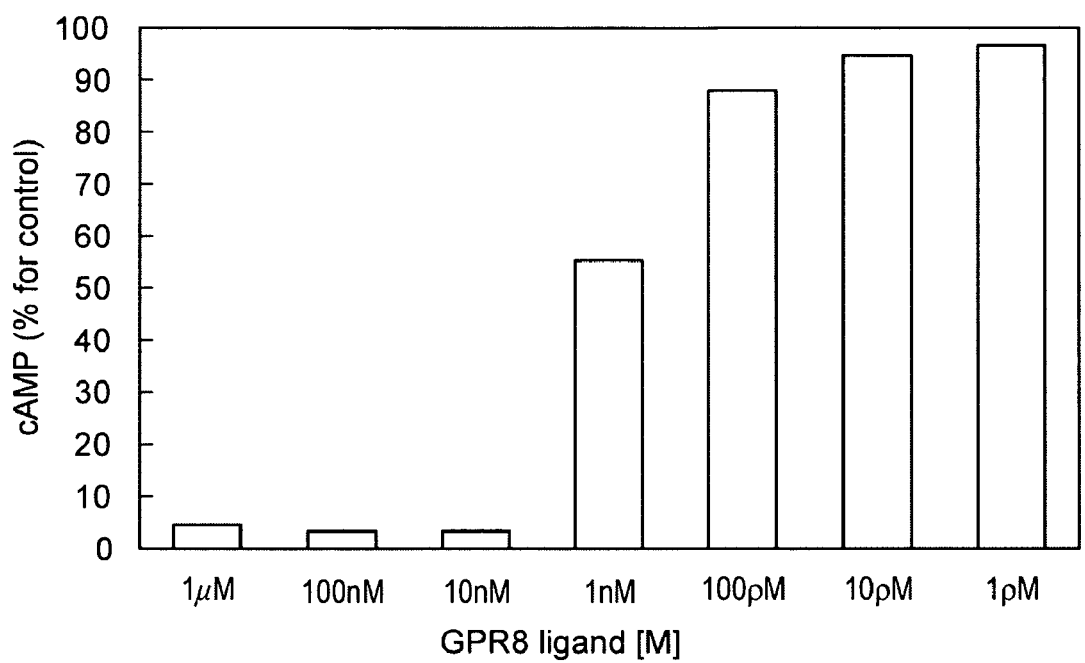
FIG. 7 shows the cAMP production suppressing activity of GPR8 ligand peptide composed of 30 residues in various concentrations on human homologue CHO/GPR8 cells.

Intracellular cAMP Production Suppressing Activity of Human Homologue of the GPR8 Ligand Peptide Composed of 30 Residues When Measured Using GPR8-expressed CHO Cells hGPR8L (1-30), which was synthesized in REFERENCE EXAMPLE 13, was brought in contact with the GPR8-expressed CHO cells in various concentrations according to the procedures described in REFERENCE EXAMPLE 5, to assay the intracellular cAMP production suppressing activity. The results are shown in FIG. 7. Obviously, hGPR8L (1-30) suppressed the intracellular cAMP production dose-dependently in the GPR8-expressed CHO cells. In the figure, the cAMP synthesis suppressing activity is expressed by the value in terms of %, which is obtained when the intracellular cAMP level added with a reaction buffer is subtracted from the intracellular cAMP level when hGPR8L (1-30) is added, wherein the intracellular cAMP level obtained by subtracting the intracellular cAMP level added with a reaction buffer from the intracellular cAMP level added with a forskolin-containing reaction buffer is made 100%.

Reference Example 24

Activity of GPR8 Ligand on Eating Behavior

Wistar male rats (9 weeks old) under pentobarbital anesthesia were inserted with a guide cannula (AG-8) targeted at the lateral ventricle (AP: 8.1, L: 1.8, H: 7.1 mm). Animals were allowed at least a week of recovery postoperatively before being used in the experiments. During the recovery period, animals were subjected to handling every day to minimize a stress caused by intracerebroventricular injection.

Figure 6:
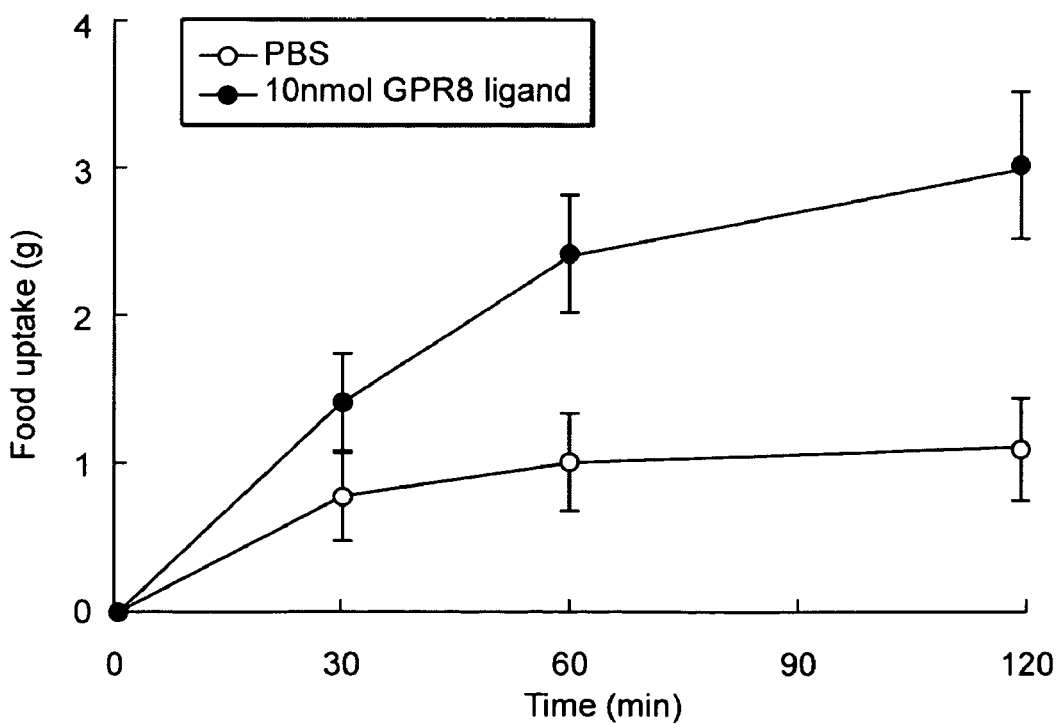
FIG. 6 shows the activity of GPR8 ligand peptide on food uptake, wherein each value is a mean value±SEM (n=10).

Feeding test commenced at 15:00. Rats were inserted with a microinjection cannula under unanesthesia and nonrestraint, and were given a PBS solution of the peptide (peptide composed of the amino acid sequence represented by SEQ ID NO: 16) obtained in REFERENCE EXAMPLE 12 or PBS alone in a dose of 5 µl/min for 2 minutes. The microinjection cannula was removed 1 minute after completion of the injection and animals were allowed to free access to preweighed feed (pellets CE2: Nippon Kurea). Time began to count from the time of injection and food intake was measured by weighing the pellets after 30, 60 and 120 minutes (FIG. 6).

Reference Example 25

Cloning of 5' Upstream End of cDNA Encoding Human GPR8 Ligand Precursor Protein

5' RACE PCR was carried out to clarify the 5' upstream base sequence of cDNA encoding the human GPR8 ligand precursor protein, in which human hypothalamus cDNA was used as a template and a primer prepared based on the human cDNA sequence (SEQ ID NO: 14) encoding a part of the precursor protein of a human homologue of the ligand peptide to GPR8 described in REFERENCE EXAMPLE 11 (hereinafter sometimes referred to as human GPR8 ligand) was used. The 5' RACE PCR cloning was effected by the following procedures: PCR was carried out by using human hypothalamic Marathon-Ready cDNA (CLONTECH) as a template and using AP1 primer attached to the kit and the synthetic primer of SEQ ID NO: 33, and then using this PCR solution as a template, PCR was further carried out using AP2 primer attached to the kit and the synthetic primer of SEQ ID NO: 34. The compositions of reaction solutions and reaction conditions for PCR were as follows. The reaction solution was composed of 4 µl of human hypothalamic cDNA, 0.5 µM of AP1 primer, 0.5 µM of the synthetic DNA primer of SEQ ID NO: 33, 0.4 mM of dNTPs and 0.2 µl of LATaq polymerase (Takara Shuzo Co., Ltd.), with GC (I) buffer attached to the enzyme added to make the total reaction volume of 20 µl. Using Thermal Cycler (PE Biosystems), the reaction solution was, after heating at 96° C. for 120 seconds, subjected to 30 repetitions of one cycle set to include 96° C. for 30 seconds and 68° C. for 240 seconds, and finally kept at 72° C. for 10 minutes. Next, the PCR solution was diluted to 50-fold with Tricine-eDTA buffer attached to the kit. A 2 µl aliquot of the dilution, 0.5 µM of AP2 primer, 0.5 µM of the synthetic DNA primer of SEQ ID NO: 34, 0.4 mM of dNTPs and 0.2 µl of LATaq polymerase (Takara Shuzo Co., Ltd.), with GC (1) buffer attached to the enzyme added to make the total reaction volume of 20 µl. Using Thermal Cycler (PE Biosystems), the reaction solution was, after heating at 96° C. for 120 seconds, subjected to 4 repetitions of one cycle set to include 96° C. for 30 seconds and 72° C. for 180 seconds, 4 repetitions of one cycle set to include 96° C. for 30 seconds and 70° C. for 180 seconds, 17 repetitions of one cycle set to include 96° C. for 30 seconds and 68° C. for 180 seconds, and finally kept at 72° C. for 10 minutes. After the amplified DNA was isolated by 1.2% agarose gel electrophoresis, the DNA having a size of about-1200 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequericing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 35.

Reference Example 26

Preparation of Human Brain cDNA

Human brain cDNA was prepared from human brain poly A (+) RNA (CLONTECH) using Marathon™ cDNA Amplification Kit (CLONTECH). cDNAs provided for RACE PCR were prepared in accordance with the protocol attached to the kit, except for synthesis of the 1st strand cDNA. The 1st strand cDNA was synthesized from 1 µg of human brain poly A (+) RNA using reverse transcriptase MMLV (-RNAse H) (RefTraAce, Toyobo Co., Ltd.) in place of reverse transcriptase AMV attached to the kit.

Reference Example 27

Cloning of 3' Downstream End of cDNA Encoding Human GPR8 Ligand Precursor Protein 3' RACE PCR was carried out to clarify the 3' downstream base sequence of cDNA encoding the human GPR8 ligand, in which human brain cDNA was used as a template and a primer prepared based on the human cDNA sequence (SEQ ID NO: 14) encoding a part of the precursor protein of a human homologue of the ligand peptide to GPR8 described in REFERENCE EXAMPLE 11 was used. The 3' RACE PCR cloning was effected by the following procedures: PCR was carried out by using human brain cDNA as a template and using AP1 primer attached to the kit and the synthetic primer of SEQ ID NO: 36, and then using this PCR solution as a template, PCR was further carried out using AP2 primer attached to the kit and the synthetic primer of SEQ ID NO: 37. The compositions of reaction solutions and reaction conditions for PCR were as follows. The reaction solution was composed of 1 µl of human brain cDNA diluted to 50-fold with Tricine-eDTA Buffer attached to the kit, 0.5 µM of AP1 primer, 0.5 µM of fvie synthetic DNA primer of SEQ ID NO: 36, 0.4 mM of dNTPs and 0.2 µl of LATaq polymerase (Takara Shuzo Co., Ltd.), with GC (I) buffer attached to the enzyme added to make the total reaction volume of 20 µl. Using Thermal Cycler (PE Biosystems), the reaction solution was, after heating at 96° C. for 120 seconds, subjected to 30 repetitions of one cycle set to include 96° C. for 30 seconds and 68° C. for 240 seconds, and finally kept at 72° C. for 10 minutes. Next, the PCR solution was diluted to 50-fold with Tricine-eDTA buffer attached to the kit. A 1 µl aliquot of the diluted PCR solution, 0.5 µM of AP2 primer, 0.5 µM of the synthetic DNA primer of SEQ ID NO: 37, 0.4 mM of dNTPs and 0.2 µl of LATaq polymerase (Takara Shuzo Co., Ltd.), with GC (1) buffer attached to the enzyme added to make the total reaction volume of 20 µl. Using Thermal Cycler (PE Biosystems), the reaction solution was, after heating at 96° C. for 120 seconds, subjected to 4 repetitions of one cycle set to include 96° C. for 30 seconds and 72° C. for 180 seconds, 4 repetitions of one cycle set to include 96° C. for 30 seconds and 70° C. for 180 seconds, 17 repetitions of one cycle set to include 96° C. for 30 seconds and 68° C. for 180 seconds, and finally kept at 72° C. for 10 minutes. After the amplified DNA was isolated by 1.5% agarose gel electrophoresis, the DNA having a size of about 600 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 38.

Reference Example 28

Cloning of cDNA Encoding Human GPR8 Ligand Precursor Protein

Amplification was carried out by. PCR to effect the cloning of cDNA encoding the human GPR8 ligand precursor protein, in which human hypothalamus cDNA was used as a template and a primer prepared based on the 5' upstream base sequence of cDNA encoding human GPR8 ligand precursor protein and a primer prepared based on the 3' downstream base sequence of cDNA encoding the human GPR8 ligand precursor protein was used. The compositions of reaction solutions and reaction conditions for PCR were as follows. The reaction solution was composed of 1 µl of human hypothalamus Marathon-Ready cDNA (CLONTECH), 0.5 µM of the synthetic DNA primer of SEQ ID NO: 39, 0.5 µM of the synthetic DNA primer of SEQ ID NO: 40, 0.4 mM of dNTPs, 2.5 mM of MgCl$_2$, 5% DMSO and 0.2 µl of LATaq polymerase (Takara Shuzo Co., Ltd.), with the buffer attached to the enzyme added to make the total reaction volume of 20 µl. Using Thermal Cycler (PE Biosystems), the reaction solution was, after heating at 96° C. for 60 seconds, subjected to 35 repetitions of one cycle set to include 96° C. for 30 seconds, 64° C. for 30 seconds and 72° C. for 120 seconds, and finally kept at 72° C. for 10 minutes. After the amplified DNA was isolated by 1.5% agarose gel electrophoresis, the DNA having a size of about 700 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs, were decoded by using a fluorescent automatic sequencer to acquire the DNA sequence epresented by SEQ ID NO: 41.

Since this sequence (SEQ ID NO: 41) encodes human GPR8 ligand precursor protein, *Escherichia coli* transformed by plasmid bearing this DNA was named TOP10/pCR2.1-TOPO Human GPR8 Ligand Precursor.

In the DNA sequence represented by SEQ ID NO: 41, such a frame as encoding the amino acid sequence of human GPR8 ligand peptide described in REFERENCE EXAMPLE 11 is present, but the 5' upstream side has no ATG supposed to be an initiation codon of protein translation. However there are some examples reported so far that codons other than ATG are assumed to act as initiation codon in some-proteins (human basic fibroblast growth factor (H. Prats et al., Proc. Natl. Acad. Sci. USA, 86, 1836-1840, 1989; R. Z. Florkiewicz and A. Sommer, Proc. Natl. Acad. Sci. USA, 86, 3978-3981, 1989), mouse retinoic acid receptor β4 (S. Nagpal et al., Proc. Natl. Acad. Sci. USA, 89, 2718, 1992), human phosphoribosylpyrophosphate synthase (M. Taira et al., J. Biol. Chem., 265, 16491-16497, 1990), drosophila choline acetltransferase (H. Sugihara et al., J. Biol. Chem., 265, 21714-21719, 1990)).

In these reports, Leu-encoding CTG is frequently predicted to serve as an initiation codon in place of ATG, and such will also apply to human GPR8 ligand precursor protein. Based on comparison with the precursor protein of porcine or rat GPR8 ligand homologue later described, it was thus assumed that a CTG codon present at the position almost corresponding to ATG, supposed to serve as an initiation codon in these precursor proteins, would be read as an initiation codon, and a sequence of the precursor protein was predicted. The ainino acid sequence of this hypothetical human GPR8 ligand precursor protein is shown by SEQ ID NO: 42. Also, the amino acid sequence and DNA sequence of hypothetical human GPR8 ligand precursor protein are shown in FIG. 8.

Reference Example 29

Preparation of Porcine Spinal Cord cDNA

Porcine spinal cord cDNA was prepared from porcine spinal cord poly A (+) RNA (CLONTECH) using Marathon™ cDNA Amplification Kit (CLONTECH). Porcine spinal cord poly A (+) RNA was prepared from porcine spinal cord as follows. Porcine spinal cord was fully homogenized in ISOGEN (Nippon Gene) with a Polytron homogenizer. From the homogenate, porcine spinal cord total RNA was acquired in accordance with the total RNA preparation method using LSOGEN solution. Next, chromatography was performed twice using oligo dT cellulose column attached to mRNA Purification Kit (Amersham Pharmacia Biotech) to acquire 7 μg of porcine spinal cord poly A (+) RNA. The cDNAs provided for RACE PCR were prepared in accordance with the protocol attached to the kit, except for synthesis of the 1st strand cDNA. The 1st strand cDNA was synthesized from 1 μg of porcine spinal cord poly A (+) RNA using reverse transcriptase MMLV (-RNAse H) (RefTraAce, Toyobo Co., Ltd.) in place of reverse transcriptase AMV attached to the kit.

Reference Example 30

Cloning of 5' Upstream End of cDNA Encoding Porcine GPR8 Ligand Precursor Protein The first 5' RACE PCR followed by the second 5' RACE PCR using a base sequence of the DNA amplified by the first PCR revealed the 5' upstream base sequence of cDNA encoding the precursor protein of a porcine homologue of the GPR8 ligand peptide (hereinafter sometimes referred to as porcine GPR8 ligand).

The first 5' RACE PCR cloning was attained by the following procedures. PCR was carried out, in which the aforesaid porcine spinal cord cDNA was used as a template and AP1 primer attached to the kit and the synthetic primer of SEQ ID NO: 43 were used, which was followed by PCR using this PCR solution as a template and further using AP2 primer attached to the kit and the synthetic primer of SEQ ID NO: 44. The compositions of reaction solutions and reaction conditions for PCR were as follows. The reaction solution was composed of 4 μl of porcine spinal cord cDNA diluted to 50-fold with Tricine-eDTA Buffer attached to the kit, 0.5 PM of AP1 primer, 0.5 μM of the synthetic DNA primer of SEQ ID NO: 43, 0.4 mM of dNTPs and 0.2 μl of LATaq polymerase (Takara Shuzo Co., Ltd.), with GC (1) buffer attached to the enzyme added to make the total reaction volume of 20 μl. Using Thermal Cycler (PE Biosystems), the reaction solution was, after heating at 96° C. for 120 seconds, subjected to 30 repetitions of one cycle set to include 96° C. for 30 seconds and 68° C. for 180 seconds, and finally kept at 72° C. for 10 minutes. Next 1 μl of the PCR solution diluted to 100-fold with Tricine-eDTA buffer attached to the kit, 0.5 μM of AP2 primer, 0.5 μM of the synthetic DNA primer of SEQ ID NO: 44, 0.4 mM of dNTPs and 0.2 μl of Advantage-GC 2 polymerase (CLONTECH), with the buffer attached to the enzyme added to make the total reaction volume of 20 μl. Using Thermal Cycler (PE Biosystems), the reaction solution was, after heating at 96° C. for 60 seconds, subjected to 3 repetitions of one cycle set to include 96° C. for 30 seconds and 72° C. for 180 seconds, 3 repetitions of one cycle set to include 96° C. for 30 seconds and 70° C. for 180 seconds, then 4 repetitions of one cycle set to include 96° C. for 30 seconds and 68° C. for 180 seconds, and then 15 repetitions of one cycle set to include 96° C. for 30 seconds, 64° C. for 30 seconds and 72° C. for 180 seconds, and finally kept at 72° C. for 10 minutes. The amplified DNA was isolated by 1.2% agarose gel electrophoresis, and the DNA having a size of about 300 bp was excised with a razor blade and recovered using QLAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin, IPTG and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 45.

The second 5' RACE PCR cloning was effected by the following procedures. Using the porcine spinal cord cDNA as a template, PCR was carried out using AP1 primer attached to the kit and the synthetic primer of SEQ ID NO: 46, followed by PCR using this PCR solution as a template and further using AP2 primer attached to the kit and the synthetic primer of SEQ ID NO: 47. The compositions of reaction solutions and reaction conditions for PCR were as follows. The reaction solution was composed of 1 µl of porcine spinal cord cDNA diluted to 50-fold with Tricine-eDTA Buffer attached to the kit, 0.5 µM of AP1 primer, 0.5 µM of the synthetic DNA primer of SEQ ID NO: 46, 0.4 mM of dNTPs and 0.2 µl of Advantage-GC 2 polymerase (CLONTECH), with GC (I) buffer attached to the enzyme added to make the total reaction volume of 20 µl. Using Thermal Cycler (PE Biosystems), the reaction solution was, after heating at 96° C. for 60 seconds, subjected to 5 repetitions of one cycle set to include 96° C. for 30 seconds and 72° C. for 180 seconds, 5 repetions of one cycle set to include 96° C. for 30 seconds and 70° C. for 180 seconds, 20 repetitions of one cycle set to include 96° C. for 30 seconds is and 68° C. for 180 seconds, and finally kept at 72° C. for 10 minutes. Next, 1 µl of the PCR solution diluted to 100-fold with Tricine-eDTA buffer attached to the kit, 0.5 µM of AP2 primer, 0.5 µM of the synthetic DNA primer of SEQ ID NO: 47, 0.4 mM of dNTPs and 0.2 µl of Advantage-GC 2 polymerase (CLONTECH), with the buffer attached to the enzyme added to make the total reaction volume of 20 µl. Using Thermal Cycler (PE Biosystems), the reaction solution was, after heating at 96° C. for 60 seconds, subjected to 31 repetitions of one cycle set to include 96° C. for 30 seconds and 68° C. for 180 seconds, and finally kept at 72° C. for 10 minutes. The amplified DNA was isolated by 2.0% agarose gel electrophoresis, and the DNA having a size of about 200 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin, IPTG and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 48.

Reference Example 31

Cloning of 3' Downstream End of cDNA Encoding Porcine GPR8 Ligand Precursor Protein The 3' downstream base sequence of cDNA encoding the precursor protein of porcine GPR8 ligand peptide was clarified by 3' RACE PCR cloning using a primer prepared based on the 5' upstream base sequence of cDNA encoding the porcine GPR8 ligand precursor protein. The 3' RACE PCR cloning was achieved by carrying out PCR using porcine spinal cord cDNA as a template and further using AP1 primer attached to the kit and the synthetic primer of SEQ ID NO: 49, followed by PCR using the resulting PCR solution as a tem plate and further using AP2 primer attached to the kit and the synthetic primer of SEQ ID NO: 50. The compositions of reaction solutions and reaction conditions for PCR were as follows. The reaction solution composed of 1 µl of porcine spinal cord cDNA diluted to 50-fold with Tricine-eDTA Buffer attached to the kit, 0.5 µM of AP1 primer, 0.5 µM of the synthetic DNA primer of SEQ ID NO: 49, 0.4 mM of dNTPs and 0.2 µl of Advantage-GC 2 polymerase (CLONTECH) was made the total reaction volume of 20 µl, with addition of the buffer attached to the enzyme. Using Thermal Cycler (PE Biosystems), the reaction solution was, after heating at 96° C. for 60 seconds, subjected to 5 repetitions of one cycle set to include 96° C. for 30 seconds and 72° C. for 120 seconds, 5 repetitions of one cycle set to include 96° C. for 30 seconds and 70° C. for 120 seconds, then 20 repetitions of one cycle set to include 96° C. for 30 seconds and 68° C. for 120 seconds, and finally kept at 72° C. for 10 minutes. Next, the reaction solution composed of 1 µl of the PCR solution diluted to 100-fold with Tricine-eDTA Buffer attached to the kit, 0.5 µM of AP2 primer, 0.5 µM of the synthetic DNA primer of SEQ ID NO: 50, 0.4 mM of dNTPs and 0.2 µl of Advantage-GC 2 polymerase (CLONTECH) was made the total reaction volume of 20 µl, with addition of the buffer attached to the enzyme. Using Thermal Cycler (PE Biosystems), the reaction solution was, after beating at 96° C. for 120 seconds, subjected to 31 repetitions of one cycle set to include 96° C. for 30 seconds and 68° C. for 120 seconds, and finally kept at 72° C. for 10 minutes. After the amplified DNA was isolated by 2.0% agarose gel electrophoresis, the DNA having a size of about 650 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin, X-gal and IPTG. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 51.

Reference Example 32

Cloning of cDNA Encoding Porcine GPR8 Ligand Precursor Protein

A cDNA encoding the porcine GPR8 ligand precursor protein was cloned by PCR amplification with a primer prepared based on the 5' upstream base sequence of cDNA encoding the porcine GPR8 ligand precursor protein, in which porcine spinal cord cDNA was used as a template. The compositions of reaction solutions and reaction conditions for PCR were as follows. The reaction solution was composed of 1 µl of porcine spinal cord cDNA diluted to 50-fold with Tricine-eDTA Buffer attached to the kit, 0.5 µM of the synthetic DNA primer of SEQ ID NO: 52, 0.5 µM of the synthetic DNA primer of SEQ ID NO: 53, 0.4 mM of dNTPs, 0.2 µl of Advantage 2 polymerase (CLONTECH), with the buffer attached to the enzyme added to make the total reaction volume of 20 µl. Using Thermal Cycler (PE Biosystems), the reaction solution was, after heating at. 96° C. for 60 seconds, subjected to 4 repetitions of one cycle set to include 96° C. for 30 seconds and 72° C. for 75 seconds, 4 repetitions of one cycle set to include 96° C. for 30 seconds and 70° C. for 75 seconds, then 4 repetitions of one cycle set to include 96° C. for 30 seconds and 68° C. for 75 seconds, next 5 repetitions of one cycle set to include 96° C. for 30 seconds, 64° C. for 30 second and 72° C. for 45 seconds, then 20 repetitions of one cycle set to include 96° C. for 30 seconds, 60° C. for 30 second and 72° C. for 45 seconds, and finally kept at 72° C. for 10 minutes. The amplified DNA was isolated by 1.2% agarose gel electrophoresis, and the DNA having a size of about 600 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 54. Since this sequence (SEQ ID NO: 54) encodes porcine GPR8 ligand precursor protein, *Escherichia coli* transformed by a plasmid bearing this DNA was named TOP10/pCR2.1-TOPO Porcine GPR8 Ligand Precursor.

The amino acid sequence for porcine GPR8 ligand precursor encoded by the DNA sequence of SEQ ID NO: 54 is shown by SEQ ID NO: 55. In the amino acid sequence of this precursor protein, there was present a sequence up to 17 residues from the N terminus, which was clarified by amino acid sequencing of the GPR8 ligand peptide isolated from porcine hypothalamus using as an indicator the GTPγ S binding activity to the GPR8-expressed cell membrane fraction described in REFERENCE EXAMPLE 10. In addition, the Arg-Arg sequence (Seidah, N. G. et al., Ann. N.Y. Acad. Sci., 839, 9-24, 1998) was present at 2 sites in the carboxy terminal side of that sequence, from which sequence a normal physiologically active peptide was considered to be excised, as in the human homologue precursor protein of GPR8 ligand peptide. In view of the foregoing, it was deduced that the amino acid sequence of a porcine homologue of the GPR8 ligand peptide would be either SEQ ID NO: 56 or 57 or both. FIG. 9 shows the amino acid sequence and DNA sequence of porcine GPR8 ligand precursor protein.

Reference Example 33

Cloning of cDNA Fragment Encoding a Part of Rat GPR8 Ligand Precursor Protein

As described in REFERENCE EXAMPLE 10, database survey was made based on the sequence of 17 amino acids from the N terminus (SEQ ID NO: 6) of the peptide purified from porcine hypothalamus using as an indicator the GTPγ S binding activity on the GPR8-expressed cell membrane fraction. Thus, rat EST base sequence (Accession No. H31598), which coincided with the base sequence of SEQ ID NO: 11, was found. The DNA sequence had a translation frame, in which the sequence of 15 amino acids was identical with the amino acid sequence (SEQ ID NO: 6) for the peptide purified from porcine hypothalamus. This H31598 is an EST sequence derived from cDNA library prepared from rat PC12 cells, and is composed of 260 bases including unidentified 7 bases. Since this H31598 was assumed to encode a part of the precursor protein of a rat homologue peptide of GPR8 ligand (hereinafter sometimes referred to as rat GPR8 ligand), in order to determine its accurate base sequence, PCR cloning was carried out on the respective primers prepared based on the 5' base sequence and 3' base sequence of H31598 using rat brain Marathon-Ready cDNA (CLONTECH) as a template. The compositions of reaction solutions and reaction conditions for PCR were as follows. The reaction solution composed of 2 µl of rat brain Marathon cDNA (CLONTECH), 0.5 µM of the synthetic DNA primer of SEQ ID NO: 60, 0.5 µM of the synthetic DNA primer of SEQ ID NO: 61, 0.4 mM of dNTPs and 0.2 µl of Advantage-GC 2 polymerase (CLONTECH) was made the total reaction volume of 20 µl, with addition of the buffer attached to the enzyme. Using Thermal Cycler (PE Biosystems), the reaction solution was, after heating at 96° C. for 60 seconds, subjected to 35 repetitions of one cycle set to include 96° C. for 30 seconds, 60° C. for 30 seconds and 72° C. for 60 seconds, and finally kept at 72° C. for 10 minutes. The amplified DNA was isolated by 4.0% agarose gel electrophoresis, and the DNA having a size of about 250 bp was excised with a razor blade and recovered using QIAquick Gel Extraction Kit (Qiagen). The recovered DNA was subcloned into vector PCR2.1-TOPO according µl to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 62. Comparison between the base sequence (SEQ ID NO: 62) of the PCR-cloned DNA and the base sequence of H31589 revealed that there was a reading error of one base deletion in the base sequence of H31589.

Reference Example 34

Cloning of 5' Upstream End of cDNA Encoding Rat GPR8 Ligand Precursor Protein

The 5' upstream base sequence of cDNA encoding the rat GPR8 ligand precursor protein was clarified by 5' RACE PCR cloning. The 5' RACE PCR cloning was effected by carrying out PCR using AP1 primer attached to the kit and the synthetic primer of SEQ ID NO: 63, in which rat brain Marathon-Ready cDNA (CLONTECH) was used as a template, followed by PCR using AP2 primer attached to the kit and the synthetic primer of SEQ ID NO: 64, in which the resulting PCR solution was used as a template. The compositions of reaction solutions and reaction conditions for PCR were as follows. The reaction solution composed of 2 µl of rat brain Marathon cDNA (CLONTECH), 0.5 µM of AP1 primer, 0.5 µM of the synthetic DNA primer of SEQ ID NO: 63, 0.4 mM of dNTPs and 0.2 µl of LATaq polymerase (Takara Shuzo Co., Ltd.) was made the total reaction volume of 20 µl, with addition of GC (I) buffer attached to the enzyme. Using Thermal Cycler (PE Biosystems), the reaction solution was, after heating at 96° C. for 60 seconds, subjected to 30 repetitions of one cycle set to include 96° C. for 30 seconds and 68° C. for 120 seconds, and finally kept at 72° C. for 10 minutes. Next, the reaction solution composed of 2 μl of the PCR solution diluted to 200-fold with Tricine-eDTA Buffer attached to the kit, 0.5 μM of AP2 primer, 0.5 μM of the synthetic DNA primer of SEQ ID NO: 64, 0.4 mM of dNTPs and 0.2 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 60 seconds, subjected to 31 repetitions of one cycle set to include 96° C. for 30 seconds and 68° C. for 120 seconds, and finally kept at 72° C. for 10 minutes. The amplified DNA was isolated by 1.2% agarose gel electrophoresis, and the DNA having a size of about 600 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 65.

Reference Example 35

Cloning of 3' Downstream End of cDNA Encoding Rat GPR8 Ligand Precursor Protein

The 3' downstream base sequence of cDNA encoding rat GPR8 ligand precursor protein was clarified by 3' RACE PCR cloning using a primer prepared based on the 5' upstream terminal base sequence of cDNA encoding the rat GPR8 ligand precursor protein and a primer prepared based on the cDNA fragment sequence encoding a part of the rat GPR8 ligand precursor protein. The 3' RACE PCR cloning was effected by carrying out PCR using AP1 primer attached to the kit and the synthetic primer of SEQ ID NO: 66, in which rat brain Marathon-Ready cDNA (CLONTECH) was used as a template, followed by PCR using AP2 primer attached to the kit and the synthetic primer of SEQ ID NO: 67, in which the resulting PCR solution was used as a template. The compositions of reaction solutions and reaction conditions for PCR were as follows. The reaction solution composed of 2 μl of rat brain Marathon-Ready cDNA (CLONTECH), 0.5 μM of AP1 primer, 0.5 μM of the synthetic DNA primer of SEQ ID NO: 66, 0.4 mM of dNTPs and 0.4 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 60 seconds, subjected to 30 repetitions of one cycle set to include 96° C. for 30 seconds and 68° C. for 180 seconds, and finally kept at 72° C. for 10 minutes. Next, the reaction solution composed of 2 μl of the PCR solution diluted to 200-fold with Tricine-eDTA Buffer attached to the kit, 0.5 μM of AP2 primer, 0.5 μM of the synthetic DNA primer of SEQ ID NO: 67, 0.4 mM of dNTPs and 0.4 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 60 seconds, subjected to 30 repetitions of one cycle set to include 96° C. for 30 seconds and 68° C. for 180 seconds, and finally kept at 72° C. for 10 minutes. The amplified DNA was isolated by 1.2% agarose gel electrophoresis, and the DNA having a size of about 600 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 68.

Reference Example 36

Cloning of cDNA Encoding Rat GPR8 Ligand Precursor Protein

A cDNA encoding the rat GPR8 ligand precursor protein was cloned by PCR amplification with a primer prepared based on the 5' upstream base sequence of cDNA encoding the rat GPR8 ligand precursor protein and a primer prepared based on the 3' downstream base sequence of cDNA encoding the rat GPR8 ligand precursor protein, in which rat brain cDNA was used as a template. The compositions of reaction solutions and reaction conditions for PCR were as follows. The reaction solution was composed of 1 μl of rat brain Marathon-Ready cDNA, 0.5 μM of the synthetic DNA primer of SEQ ID NO: 69, 0.5 μM of the synthetic DNA primer of SEQ ID NO: 70, 0.4 mM of dNTPs and 0.4 μl of Advantage 2 polymerase (CLONTECH), with the buffer attached to the enzyme added to make the total reaction volume of 20 μl. Using Thermal Cycler (PE Biosystems), the reaction solution was, after heating at 96° C. for 60 seconds, subjected to 35 repetitions of one cycle set to include 96° C. for 30 seconds, 60° C. for 30 seconds and 72° C. for 60 seconds, and finally kept at 72° C. for 10 minutes. The amplified DNA was isolated by 1.2% agarose gel electrophoresis, and the DNA having a size of about 750 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 71. Since this sequence (SEQ ID NO: 71) encodes the rat GPR8 ligand precursor protein, *Escherichia coli* transformed by a plasmid bearing this DNA was named TOP10/pCR2.1-TOPO Rat GPR8 Ligand Precursor.

The amino acid sequence for rat GPR8 ligand precursor encoded by the DNA sequence of SEQ ID NO: 71 is shown by SEQ ID NO: 72. In the amino acid sequence of this precursor protein, there was present a similar sequence that is different only in the 5th and 17th amino acids from the sequence up to 17 residues from the N terminus, which was clarified by amino acid sequencing of the GPR8 ligand peptide isolated from porcine hypothalamus using as an indicator the GTPγS binding activity to the GPR8-expressed cell membrane fraction described in REFERENCE EXAMPLE 10. In addition, the Arg-Arg sequence (Seidah, N. G. et al., Ann. N.Y. Acad. Sci., 839, 9-24, 1998) was present at 2 sites in the carboxy terminal side of that sequence, from which sequence a normal physiologically active peptide was considered to be excised, as in the human or porcine homologue precursor protein of GPR8 ligand peptide. In view of the foregoing, it was deduced that the amino acid sequence of a rat homologue of the GPR8 ligand peptide would be either SEQ ID NO: 73 or 74 or both. FIG. 10 shows the amino acid sequence and DNA sequence of rat GPR8 ligand precursor protein.

Reference Example 37

Cloning of cDNA Fragment Encoding a Part of Mouse GPR8 Ligand Precursor Protein

A Database search was conducted based on the base sequence encoding porcine GPR8 ligand peptide of 23 amino acid residues represented by SEQ ID NO: 58. As a result of mouse genome database of Celera Genomics, the mouse genome fragment sequence of SEQ ID NO: 77 containing a base sequence similar to the base sequence of SEQ ID NO: 58 was discovered. It was predicted that this sequence would be a genome fragment sequence encoding a part of the precursor protein of a mouse homologue of the GPR8 ligand peptide (hereinafter sometimes referred to as mouse GPR8 ligand). The compositions of reaction solutions and reaction conditions for PCR were as follows. One microliter of mouse testis cDNA (CLONTECH), 0.5 μM of the synthetic DNA primer of SEQ ID NO: 78, 0.5 μM of the synthetic DNA primer of SEQ ID NO: 79, 0.4 mM of dNTPs and 0.2 μl of LATaq polymerase (Takara Shuzo Co., Ltd.) was made the total reaction volume of 20 μl, with addition of GC (I) buffer attached to the enzyme. Using Thermal Cycler (PE Biosystems), the reaction solution was, after heating at 96° C. for 120 seconds, subjected to 10 repetitions of one cycle set to include 96° C. for 30 seconds and 68° C. for 120 seconds, 25 repetitions of one cycle set to include 96° C. for 30 seconds, 64° C. for 30 seconds and 72° C. for 120 seconds, and finally kept at 72° C. for 10 minutes. The amplified DNA was isolated by 1.5% agarose gel electrophoresis, and the DNA having a size of about 350 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert, fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer (SEQ ID NO: 80). The base sequence of cDNA acquired herein by the PCR cloning was fully coincident with the mouse genome fragment base sequence inserted between the 2 base sequences used for the primers of SEQ ID NO: 78 and SEQ ID NO: 79.

Reference Example 38

Preparation of Mouse Brain cDNA

Mouse brain cDNA was prepared from mouse brain poly A (+) RNA (CLONTECH) using SMART™ RACE cDNA Amplification Kit (CLONTECH) in accordance with the protocol attached to the kit. A solution of the 1st strand cDNA synthesized was diluted to 10-fold with Tricine-eDTA Buffer attached to the kit. The solution was used for RACE PCR.

Reference Example 39

Cloning of 5' Upstream End of cDNA Encoding Mouse GPR8 Ligand Precursor Protein

The 5' upstream base sequence of cDNA encoding the mouse GPR8 ligand precursor protein was clarified by 5' RACE PCR cloning. The 5' RACE PCR cloning was effected by PCR using Universal Primer Mix attached to SMART™ RACE cDNA Amplification Kit and the synthetic primer of SEQ ID NO: 81, in which mouse brain cDNA was used as a template, followed by PCR using Nested Universal Primer attached to the kit and the synthetic primer of SEQ ID NO: 82, in which the resulting PCR solution was used as a template. The compositions of reaction solutions and reaction conditions for PCR were as follows. The reaction solution composed of 1 μl of mouse brain cDNA, 2 μl of Universal Primer Mix, 0.2 μM of the synthetic DNA primer of SEQ ID NO: 81, 0.8 mM of dNTPs and 0.4 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 120 seconds, subjected to 30 repetitions of one cycle set to include 96° C. for 30 seconds and 68° C. for 120 seconds, and finally kept at 72° C. for 10 minutes. Next, the reaction solution composed of 0.5 μl of the PCR solution diluted to 50-fold with Tricine-eDTA Buffer attached to the kit, 0.5 μM of Nested Universal Primer, 0.5 μM of the synthetic DNA primer of SEQ ID NO: 82, 0.8 mM of dNTPs and 0.4 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 120 seconds, subjected to 30 repetitions of one cycle set to include 96° C. for 30 seconds, 60° C. for 30 seconds and 72° C. for 120 seconds, and finally kept at 72° C. for 10 minutes. The amplified DNA was isolated by 1.5% agarose gel electrophoresis, and the DNA having a size of about 300 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resuiting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 83.

Reference Example 40

Cloning of 3' Downstream End of cDNA Encoding Mouse GPR8 Ligand Precursor Protein The 3' downstream base sequence of cDNA encoding the mouse GPR8 ligand precursor protein was clarified by 3' RACE PCR cloning. The 3' RACE PCR cloning was effected by PCR using Universal Primer Mix attached to SMART™ RACE cDNA Amplification Kit and the synthetic primer of SEQ ID NO: 84, in which mouse brain cDNA was used as a template, followed by PCR using Nested Universal Primer attached to the kit and the synthetic primer of SEQ ID NO: 85, in which the resulting PCR solution was used as a template. The compositions of reaction solutions and reaction conditions for PCR were as follows. The reaction solution composed of 1 µl of mouse brain cDNA, 2 µl of Universal Primer Mix, 0.5 µM of the synthetic DNA primer of SEQ ID NO: 84, 0.8 mM of dNTPs and 0.4 µl of Advantage-GC 2 polymerase (CLONTECH) was made the total reaction volume of 20 µl, with addition of the buffer attached to the enzyme. Using Thermal Cycler (PE Biosystems), the reaction solution was, after heating at 96° C. for 120 seconds, subjected to 30 repetitions of one cycle set to include 96° C. for 30 seconds and 68° C. for 120 seconds, and finally kept at 72° C. for 10 minutes. Next, the reaction solution composed of 0.5 µl of the PCR solution diluted- to 50fold with Tricine-eDTA Buffer attached to the kit, 0.5 µM of Nested Universal Primer, 0.5 µM of the synthetic DNA primer of SEQ ID NO: 85, 0.8 mM of dNTPs and 0.4 µl of Advantage-GC 2 polymerase (CLONTECH) was made the total reaction volume of 20 µl, with addition of the buffer attached to the enzyme. Using Thermal Cycler (PE Biosystems), the reaction solution was, after heating at 96° C. for 120 seconds, subjected to 30 repetitions of one cycle set to include 96° C. for 30 seconds, 64° C. for 30 seconds and 72° C. for 120 seconds, and finally kept at 72° C. for 10 minutes. The amplified DNA was isolated by 1.5% agarose gel electrophoresis, and the DNA having a size of about 700 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to Escherichia coli TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 86.

Reference Example 41

Cloning of cDNA Encoding Mouse GPR8 Ligand Precursor Protein

A cDNA encoding the mouse GPR8 ligand precursor protein was cloned by PCR amplification with a primer prepared based on the 5' upstream base sequence of cDNA encoding the mouse GPR8 ligand precursor protein and a primer prepared based on the 3' downstream base sequence of cDNA encoding the mouse GPR8 ligand precursor protein, in which mouse brain cDNA was used as a template. The compositions of reaction solutions and reaction conditions for PCR were as follows. The reaction solution was composed of 0.5 µl of mouse brain cDNA, 0.5 µM of the synthetic DNA primer of SEQ ID NO: 87, 0.5 µM of the synthetic DNA primer of SEQ ID NO: 88, 1.6 mM of dNTPs and 0.2 µl of LATaq polymerase (Takara Shuzo Co., Ltd.), with the buffer attached to the enzyme added to make the total reaction volume of 20 µl. Using Thermal Cycler (PE Biosystems), the reaction solution was after heating at 96° C. for 120 seconds, subjected to 40 repetitions of one cycle set to include 96° C. for 30 seconds, 64° C. for 30 seconds and 72° C. for 120 seconds, and finally kept at 72° C. for 10 minutes. The amplified DNA was isolated by 1.5% agarose gel electrophoresis, and the DNA having a size of about 700 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to Escherichia coli TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 89. Since this sequence (SEQ ID NO: 89) encodes the mouse GPR8 ligand precursor protein, Escherichia coli transformed by a plasmid bearing this DNA was named TOP10/pCR2.1-TOPO Mouse GPR8 Ligand Precursor.

In the amino acid sequence of the DNA sequence represented by SEQ ID NO: 89, there is such a frame as encoding a similar amino acid sequence that is different only in the 5th and 17th amino acids from the sequence up to 17 residues from the N terminus, which was clarified by amino acid sequencing of the GPR8 ligand peptide isolated from porcine hypothalamus using as an indicator the GTPγ S binding activity to the GPR8-expressed cell membrane fraction described in REFERENCE EXAMPLE 10. As in the human GPR8 ligand precursor, however, no ATG supposed to serve as an initiation codon of protein translation does not exist at the 5' upstream side. However, as predicted in the human GPR8 ligand precursor protein, based on comparison with the precursor protein of porcine or rat GPR8 ligand homologue, it was assumed that a CTG codon present at the position almost corresponding to ATG, which is supposed to serve as an initiation codon in these precursor proteins, would be read as an initiation codon, and a sequence of the mouse GPR8 ligand precursor protein was predicted. The amino acid sequence of this hypothetical mouse GPR8 ligand precursor protein is shown by SEQ ID NO: 90. As in the case of human, porcine or rat homologue precursor protein of the GPR8 ligand peptide, the Arg-Arg sequence (Seidah, N. G. et al., Ann. N.Y. Acad. Sci., 839, 9-24, 1998) was present at 2 sites in the carboxy terminal side of the sequence supposed to be an amino acid sequence of the mouse GPR8 ligand, from which a normal physiologically active peptide was considered to be excised. In view of the foregoing, it was deduced that the amino acid sequence of a mouse homologue of the GPR8 ligand peptide would be either SEQ ID NO: 91 or 92 or both. The amino acid sequence for mouse GPR8 ligand of 23 residues represented by SEQ ID NO: 91 coincided with the amino acid sequence (SEQ ID NO: 73) for rat GPR8 ligand of 23 residues. FIG. 11 shows the amino acid sequence and DNA sequence of hypothetical mouse GPR8 ligand precursor protein.

Reference Example 42

Preparation of [$^{125}$I-Tyr$^2$]-hGPR8L (1-23) and [$^{125}$I-Tyr$^{10}$]-hGPR8L (1-23)

A solution of 1 nmol hGPR8L (1-23) in 5 μl of DMSO was mixed with 5 μl of 0.1 M nickel chloride. After the solution was mixed with 10 μl of 0.001% hydrogen peroxide aqueous solution in 0.1 M HEPES (pH 7), 10 μl of a 10 μl/ml lactoperoxidase (Sigma, Inc.) solution in 0.1 M HEPES (pH 7) and 10 μl of [125I] NaI 37 MBq (NEN LIFE SCIENCE PRODUCTS, LTD.), the mixture was reacted at room temperature for 60 minutes and fractionated by HPLC under the following conditions.

A column used was ODS-80TM (4.6 mm×15 cm) (TOSO Co., Ltd.), and using 10% acetonitrile/0.1% TFA and 60% acetonitrile/0.1% TFA as eluants A and B, respectively, gradient elution was performed in 0-0% (2 mins.), 0-30% (3 mins.) and 30-38% (5 mins.), 38-43% (55 mins.) of eluant B/eluants A+B. The flow rate was 1 mL/min, the column temperature was 25° C., and detection was made at absorbance of 220 nm.

Since 2 tyrosine residues are present in hGPR8L (1-23), [$^{125}$I-Tyr$^2$]-hGPR8L (1-23) and [$^{125}$I-Tyr$^{10}$]-hGPR8L (1-23) are produced by iodation. Under the HPLC conditions, hGPR8L (1-23), [$^{125}$I-Tyr$^2$]-hGPR8L (1-23) and [$^{125}$I-Tyr$^{10}$]-hGPR8L (1-23) were eluted at about 24 mins., 30 mins and 32 mins., respectively.

Reference Example 43

Receptor Binding Test Using [$^{125}$I-Tyr$^{10}$]-hGPR8L (1-23)

Receptor binding test was carried out using [$^{125}$I]-labeled hGPR8L (1-23) prepared as described in REFERENCE EXAMPLE 42 and the cell membrane fraction prepared from GPR8-expressed CHO cells prepared in a similar manner to the procedures described in REFERENCE EXAMPLE 6.

Figure 12:
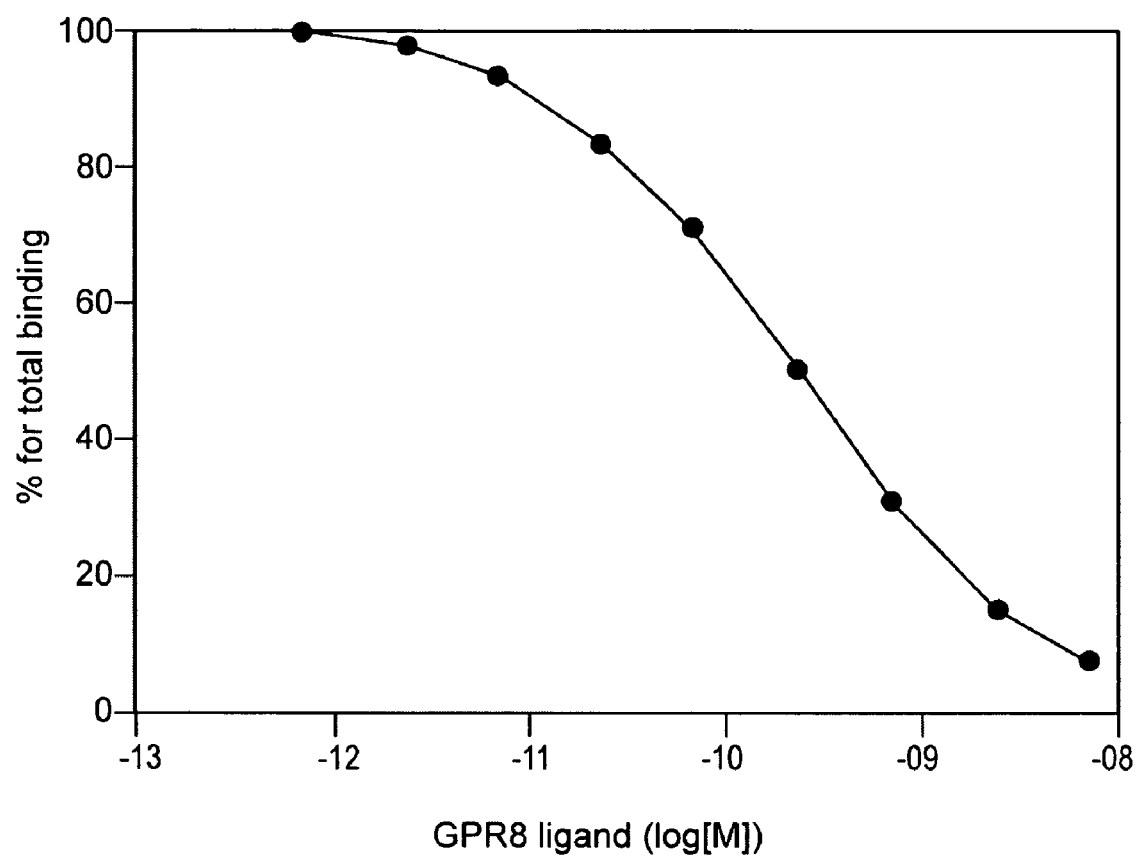
FIG. 12 is a graph showing the binding inhibitory activity of human GPR8 ligand of 23 residues on [$^{125}$I]-labeled human GPR8 ligand of 23 residues, using a cell membrane fraction prepared from human GPR8-expressed CHO cells.

The cell membrane fraction prepared from human GPR8-expressed CHO cells was diluted with an assay buffer (25 mM Tris-HCl, 5 mM EDTA (ethylenediaminetetraacetic acid), 0.05% CHAPS (3-[(3-cholamidopropyl)dimethlammonio]-1-propanesulfonate), 0.1% BSA (bovine serum albumin), 0.25 mM PMSF (phenylmethylsulfonyl fluoride), 1 μg/ml pepstatin, 20 μg/ml leupeptin, pH 7.4) in various concentrations. Subsequently, a 200 μl aliquot of the dilution was dispensed in a polypropylene test tube (Falcon 2053). To assay for the total binding (TB), 2 μl of DMSO and 2 μl of 7 nM [$^{125}$I-Tyr$^2$]-hGPR8L (1-23) or [$^{125}$I-Tyr$^{10}$]-hGPR8L (1-23) were added to the membrane fraction solution. Also, to assay for non-specific binding (NSB), 2 μl of a 100 μM hGPR8L (1-23) solution in DMSO and 2 μl of 7 nM [$^{125}$I-Tyr$^2$]-hGPR8L (1-23) or [$^{125}$I-Tyr$^{10}$]-hGPR8L (1-23) were added to the membrane fraction solution. After reacting at 25° C. for 60 minutes, the reaction solution was suction-filtrated through a polyethyleneimine-treated Whatman glass filter (GF-F). After filtration, the residual radioactivity remained on the filter paper was measured with a γ-counter, and the specific binding (SB) was estimated by subtracting the non-specific binding from the total binding. Since the specific binding obtained by using [$^{125}$I-Tyr$^{10}$]-hGPR8L (1-23) was higher by twice than the case of using [$^{125}$I-Tyr$^2$]-hGPR8L (1-23), [$^{125}$I-Tyr$^{10}$]-hGPR8L (1-23) was used in the actual test. When the concentration of membrane fraction was varied, the specific binding of [$^{125}$I-Tyr$^{10}$]-hGPR8L (1-23) was noted dependently on the concentration of membrane fraction. Also, by setting the concentration of membrane fraction at 5 μg/ml, 50% inhibitory concentration (IC$_{50}$ value) of hGPR8L (1-23) was calculated from the inhibition rate (%). The IC$_{50}$ value was found to be 0.25 nM. FIG. 12 shows the binding inhibition of hGPR8L (1-23) in various concentrations.

Reference Example 44

Production of Oxidized Human GPR8 Ligand (1-23): Trp-Tyr-Lys-His-Val-Ala-Ser-Pro-Arg-Tyr-His-Thr-Val-Gly-Arg-Ala-Ala-Gly-Leu-Leu-Met (O) -Gly-Leu (SEQ ID NO: 95)

In 0.5 ml of 50% aqueous acetic acid solution, 0.45 mg of the compound of REFERENCE EXAMPLE 12 was dissolved. Then 0.05 ml of 0.3% hydrogen peroxide aqueous solution was added to the solution, and the mixture was allowed to stand at room temperature for 8 hours. After concentrating in vacuum, the concentrate was purified on SepPark to obtain 0.443 mg of white powders.

Mass spectrum (M+H)$^+$: 2599.2 (calcd. 2599.4)
Elution time on HPLC: 19.1 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 m/min.

Reference Example 45

Production of Human GPR8 Ligand (1-22): Trp-Tyr-Lys-His-Val-Ala-Ser-Pro-Arg-Tyr-His-Thr-Val-Gly-Arg-Ala-Ala-Gly-Leu-Leu-Met-Gly (SEQ ID NO: 96)

Fmoc-Gly was introduced into commercially available 2-chlorotrityl resin (Clt resin, 1.33 mmol/g). Then, condensation of amino acids in the order of sequence, excision from the resin and purification were performed as in REFERENCE EXAMPLE 13 to obtain the product.

Reference Example 46

Production of Human GPR8 Ligand (1-21): Trp-Tyr-Lys-His-Val-Ala-Ser-Pro-Arg-Tyr-His-Thr-Val-Gly-Arg-Ala-Ala-Gly-Leu-Leu-Met (SEQ ID NO: 97)

Fmoc-Met was introduced into commercially available 2-chlorotrityl resin (Clt resin, 1.33 mmol/g). Then, condensation of amino acids in the order of sequence, excision from the resin and purification were performed as in REFERENCE EXAMPLE 13 to obtain the product.

Reference Example 47

Production of Human GPR8 Ligand (1-20): Trp-Tyr-Lys-His-Val-Ala-Ser-Pro-Arg-Tyr-His-Thr-Val-Gly-Arg-Ala-Ala-Gly-Leu-Leu (SEQ ID NO: 98)

Fmoc-Leu was introduced into commercially available 2-chlorotrityl resin (Clt resin, 1.33 mmol/g). Then, condensation of amino acids in the order of sequence, excision from the resin and purification were performed as in REFERENCE EXAMPLE 13 to obtain the product.

Mass spectrum (M+H)$^+$: 2282.8 (calcd. 2282.6)
Elution time on HPLC: 17.2 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Reference Example 48

Production of Human GPR8 Ligand (1-19): Trp-Tyr-Lys-His-Val-Ala-Ser-Pro-Arg-Tyr-His-Thr-Val-Gly-Arg-Ala-Ala-Gly-Leu (SEQ ID NO: 99)

Fmoc-Leu was introduced into commercially available 2-chlorotrityl resin (Clt resin, 1.33 mmol/g). Then, condensation of amino acids in the order of sequence, excision from the resin and purification were performed as in REFERENCE EXAMPLE 13 to obtain the product.

Mass spectrum (M+H)$^+$: 2169.6 (calcd. 2169.5)
Elution time on HPLC: 16.4 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 0/70 (35 mins.)
Flow rate: 1.0 ml/min.

Reference Example 49

Production of Human PR8 Ligand (1-18): Trp-Tyr-Lys-His-Val-Ala-Ser-Pro-Arg-Tyr-His-Thr-Val-Gly-Arg-Ala-Ala-Gly (SEQ ID NO: 100)

Fmoc-Gly was introduced into commercially available 2-chlorotrityl resin (Clt resin, 1.33 mmol/g). Then, condensation of amino acids in the order of sequence, excision from the resin and purification were performed as in REFERENCE EXAMPLE 13 to obtain the product.

Mass spectrum (M+H)$^+$: 2056.8 (calcd. 2056.3)
Elution time on HPLC: 14.2 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Reference Example 50

Production of Human GPR8 Ligand (1-17): Trp-Tyr-Lys-His-Val-Ala-Ser-Pro-Arg-Tyr-His-Thr-Val-Gly-Arg-Ala-Ala (SEQ ID NO: 101)

Fmoc-Leu was introduced into commercially available 2-chlorotrityl resin (Clt resin, 1.33 mmol/g). Then, condensation of amino acids in the order of sequence, excision from the resin and purification were performed as in REFERENCE EXAMPLE 13 to obtain the product.

Reference Example 51

Production of Human GPR8 Ligand (1-16): Trp-Tyr-Lys-His-Val-Ala-Ser-Pro-Arg-Tyr-His-Thr-Val-Gly-Arg (SEQ ID NO: 102)

Fmoc-Leu was introduced into commercially available 2-chlorotrityl resin (Clt resin, 1.33 mmol/g). Then, condensation of amino acids in the order of sequence, excision from the resin and purification were performed as in REFERENCE EXAMPLE 13 to obtain the product.

Reference Example 52

Production of Porcine GPR8 Ligand (1-23): Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 56)

Fmoc-Leu was introduced into commercially available 2-chlorotrityl resin (Clt resin, 1.33 mmol/g). Then, condensation of amino acids in the order of sequence, excision from the resin and purification were performed as in REFERENCE EXAMPLE 13 to obtain the product.

Mass spectrum (M+H)$^+$: 2585.2 (calcd. 2585.4)
Elution time on HPLC: 20.2 mins.
Conditions for elution:
Column: Wakosil-II 5C18 HG (4.6×100 mm)
Eluant: linear density gradient elution using eluant A. 0.1% TFA-water and eluant B: acetonitrile containing 0.1% TFA, with A/B=100/0 to 30170 (35 mins.)
Flow rate: 1.0 ml/min.

Reference Example 53

Production of Rat/Mouse GPR8 Ligand (1-23): Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 73 and SEQ ID NO: 91)

The condensation of amino acids in the order of sequence, excision from the resin and purification were performed as in REFERENCE EXAMPLE 52 to obtain the product.

Reference Example 54

Production of Oxidized Porcine GPR8 Ligand (1-23): Trp-Tyr-Lys-His-Val-Ala-Ser-Pro-Arg-Tyr-His-Thr-Val-Gly-Arg-Ala-Ala-Gly-Leu-Leu-Met (O) -Gly-Leu (SEQ ID NO: 103)

The compound of REFERENCE EXAMPLE 52 was oxidized as in REFERENCE EXAMPLE 44 to obtain the product.

Mass spectrum (M+H)$^+$: 2601.3 (calcd. 2601.4)
Elution time on HPLC: 18.9 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Reference Example 55

Production of Oxidized Rat/Mouse GPR8 Ligand (1-23): Trp-Tyr-Lys-His-Val-Ala-Ser-Pro-Arg-Tyr-His-Thr-Val-Gly-Arg-Ala-Ser-Gly-Leu-Leu-Met (O) -Gly-Leu (SEQ ID NO: 104)

The compound of REFERENCE EXAMPLE 53 was oxidized as in REFERENCE EXAMPLE 44 to obtain the product.

Reference Example 56

Production of [$N^\alpha$-Acetyl-Trp$^1$]-Human GPR8 Ligand (1-23): Ac-Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 106)

From the resin prepared in REFERENCE EXAMPLE 12, Fmoc group was removed. After acetylating with acetic anhydride, the acetylated product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to REFERENCE EXAMPLE 12 to obtain the product.

Mass spectrum (M+H)$^+$: 2626.12625.8 (calcd. 2627.12626.1)

Elution time on HPLC: 21.4 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with A/B=100/0 to 30/70 (35 mins.)

Flow rate: 1.0 ml/min.

Reference Example 57

Production of Human GPR8 Ligand (2-23): Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 107)

As in REFERENCE EXAMPLE 12, a desired amino acid sequence was introduced into the resin. After introducing the final Tyr and before excising from the resin, the Fmoc group was removed on the resin. Then, the Fmoc-removed product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to REFERENCE EXAMPLE 12 to obtain the product.

Mass spectrum (M+H)$^+$: 2397.1 (calcd. 2397.3)

Elution time on HPLC: 19.9 mins.

Conditions for elution:

Column: Wakosil-II 5C 18 HG (4.6×100 mm)

Eluant: linear density gradient elution using eluant A: 0.1% TFA-water and eluant B: acetonitrile containing 0.1% TFA, with A/B=100/0 to 30/70 (35 mins.)

Flow rate: 1.0 ml/min.

Reference Example 58

Production of Human GPR8 Ligand (4-23): His-Val-Ala-Ser-Pro-Arg-Tyr-His-Thr-Val-Gly-Arg-Ala-Ala-Gly-Leu-Leu-Met-Gly-Leu (SEQ ID NO: 108)

As in REFERENCE EXAMPLE 12, a desired amino acid sequence was introduced into the resin. After introducing the final His and before excising from the resin, the Fmoc group was removed on the resin. Then, the Fmoc-removed product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to REFERENCE EXAMPLE 12 to obtain the product.

Mass spectrum (M+H)$^+$: 2106.0 (calcd. 2106.1)

Elution time on HPLC: 20.0 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with A/B=100/0 to 30/70 (35 mins.)

Flow rate: 1.0 ml1 min.

Reference Example 59

Production of Human GPR8 Ligand (9-23): Arg-Tyr-His-Thr-Val-Gly-Arg-Ala-Ala-Gly-Leu-Leu-Met-Gly-Leu (SEQ ID NO: 109)

As in REFERENCE EXAMPLE 12, a desired amino acid sequence was introduced into the resin. After introducing the final Arg and before excising from the resin, the Fmoc group was removed on the resin. Then, the Fmoc-removed product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to REFERENCE EXAMPLE 12 to obtain the product.

Mass spectrum (M+H)$^+$: 1615.0 (calcd. 1614.9)

Elution time on HPLC: 20.2 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with A/B=100/0 to 30/70 (35 mins.)

Flow rate: 1.0 ml/min.

Reference Example 60

Production of Human GPR8 Ligand (15-23): Arg-Ala-Ala-Gly-Leu-Leu-Met-Gly-Leu (SEQ ID NO: 110)

As in REFERENCE EXAMPLE 12, a desired amino acid sequence was introduced into the resin. After introducing the final Arg and before excising from the resin, the Fmoc group was removed on the resin. Then, the Fmoc-removed product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to REFERENCE EXAMPLE 12 to obtain the product.

Mass spectrum (M+H)$^+$: 901.4 (calcd. 901.5)

Elution time on HPLC: 20.2 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with A/B=100/0 to 30/70 (35 mins.)

Flow rate: 1.0 ml/min.

Reference Example 61

Production of [N-Acetyl-Tyr²]-Human GPR8 Ligand (2-23): Ac-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 111)

After acetylating the resin prepared in REFERENCE EXAMPLE 57 with acetic anhydride, the acetylated product was treated and purified as in REFERENCE EXAMPLE 57 to obtain the product.

Mass spectrum (M+H)⁺: 2439.3 (calcd. 2439.3)
Elution time on HPLC: 20.2 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Reference Example 62

Production of [D-Trp¹]-Human GPR8 Ligand (1-23): D-Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 112)

The product was obtained in a manner similar to REFERENCE EXAMPLE 12, using Fmoc-D-Trp (Boc) in place of Fmoc-Trp (Boc).

Mass spectrum (M+H)⁺: 2583.4 (calcd. 2583.4)
Elution time on HPLC: 20.6 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Reference Example 63

Production of [N-3-Indolepropanyl-Tyr²]-Human GPR8 Ligand (2-23): 3-Indolepropanoyl-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 113)

Using 3-indolepropionic acid in place of Fmoc-Trp (Boc) in REFERENCE EXAMPLE 12, a desired resin was prepared. The resin was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to REFERENCE EXAMPLE 12 to obtain the product.

Mass spectrum (M+H)⁺: 2568.4 (calcd. 2568.4)
Elution time on HPLC: 21.7 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Reference Example 64

GTPγ S Binding Promoting Activity of Human and Porcine Homologue Derivatives of the GPR8 Ligand Peptide Measured Using GPR8-expressed Cell Membrane Fraction The human and porcine homologue derivatives of the GPR8 ligand peptide, which synthesis was described in the specification, were added to the GPR8-expressed cell membrane fraction in various concentrations by the procedures described in REFERENCE EXAMPLE 6 to determine the GTPγ S binding promoting activity. Sequence identification numbers of the derivatives tested and the GTPγ S binding promoting activity are shown in TABLE 1. The activity was expressed in terms of 50% effective concentration ($EC_{50}$). The GTPγ S binding promoting activities of hGPR8L (1-23) and hGPR8L (1-30) described in REFERENCE EXAMPLES 20 and 21 are also shown in the table.

Reference Example 65

Receptor Binding Activity of Human and Porcine Homologue Derivatives of the GPR8 Ligand Peptide Measured Using GPR8-expressed Cell Membrane Fraction and [¹²⁵I-Tyr¹⁰]-hGPR8L (1-23)

The receptor binding activity of the human and porcine homologue derivatives of the GPR8 ligand peptide, which synthesis was described in the specification, was determined s described in REFERENCE EXAMPLE 43, using the GPR8-expressed cell membrane fraction and [¹²⁵I-Tyr¹⁰]-hGPR8L (1-23). Sequence identification numbers of the derivatives tested and the receptor binding activity are shown in TABLE 1. The receptor binding activity was expressed in terms of 50% binding inhibitory concentration ($IC_{50}$). The receptor binding activity of hGPR8L (1-23) described in REFERENCE EXAMPLE 43 is also shown in the table.

TABLE 1

GTPγ S binding promoting activity and receptor binding activity of human and porcine homologue derivatives of GPR8 ligand peptide

| Derivative | SEQ ID NO | GTPγ S binding promoting activity ($EC_{50}$ nM) | Receptor binding ($IC_{50}$ nM) |
| --- | --- | --- | --- |
| hGPR8L(1–23) | 16 | 1.6 | 0.25 |
| hGPR8L(1–30) | 17 | 0.57 | 0.025 |
| [Met(O)]-hGPR8L(1–23) | 95 | 1.4 | 0.31 |
| Fmoc-hGPR8L(1–23) | 105 | 240 | 0.20 |
| Ac-hGPR8L(1–23) | 106 | 14 | 2.4 |
| [D-Trp¹]-hGPR8L(1–23) | 112 | 7.1 | 0.82 |
| hGPR8L(2–23) | 107 | 3900 | 160 |
| Ac-hGPR8L(2–23) | 111 | 7200 | 420 |
| IndPr-hGPR8L(2–23) | 113 | 5.0 | 0.28 |
| hGPR8L(4–23) | 108 | 6700 | 1400 |
| hGPR8L(9–23) | 109 | 4200 | 1300 |
| hGPR8L(1–20) | 98 | 0.86 | 0.20 |
| hGPR8L(1–19) | 99 | 1000 | 100 |
| hGPR8L(1–18) | 100 | >10000 | 2700 |
| pGPR8L(1–23) | 56 | 1.5 | 0.38 |
| [Met(O)]-pGPR8L(1–23) | 103 | 0.73 | 0.29 |

Reference Example 66

Amplification of Human GPR7 DNA by PCR Using Human Chromosomal DNA

Using human chromosomal DNA as a template, amplification of DNA was carried out by PCR, using 2 synthetic primers (SEQ ID NO:126 and SEQ ID NO:127). The synthetic primers were constructed so as to amplify the gene in the region to be translated into its receptor protein, whereby the recognition sequences of restriction enzymes were added to the 5' and 3' ends so that the base sequences recognized by restriction enzymes ClaI and SpeI were added to the gene at the 5' and 3' ends, respectively. The reaction solution was composed of 0.5 µl of human chromosomal DNA (TaKaRa Shuzo Co., Ltd.), 1 µM each of the synthetic DNA primers, 0.8 mM dNTPs, 1 mM MgCl$_2$ and 1 µl of KOD polymerase (Toyobo Co., Ltd.), to which the buffer attached to the enzyme was added to make the total volume 50 µl. After heating at 94° C. for 60 seconds, amplification was carried out in 35 cycles of 98° C. for 15 seconds, 65° C. for 2 seconds and 74° C. for 30 seconds using Thermal Cycler (TaKaRa Shuzo Co., Ltd.). The amplified product was confirmed by 0.8% agarose gel electrophoresis followed by staining with ethidium bromide.

Reference Example 67

Subcloning of the PCR Product to Plasmid Vector and Confirmation of the Amplified DNA Sequence by Decoding the Base Sequence of the Inserted DNA Region The reaction solution obtained by PCR in REFERENCE EXAMPLE 66 was subjected to 0.8% low melting agarose gel electrophoresis for separation. The band parts were excised from the gel with a razor blade and ground to small pieces, which were then extracted with phenol/chloroform and precipitated in ethanol to recover the DNA. According to the protocol attached to PCR-Script™ Amp SK(+) Cloning Kit (Stratagene), the recovered DNAs were subcloned into the plasmid vector, pCR-Script™ Amp SK(+). The recombinant vectors were introduced into *Escherichia coli* DH5α competent cells (Toyobo Co., Ltd.) to produce transformants. Then, clones having the DNA-inserted fragment were selected in an LB agar culture medium containing ampicillin, IPTG and X-gal. Only clones exhibiting white color were picked with a sterilized toothpick to acquire transformant *Escherichia coli* DH5α/GPR7. The individual clones were cultured overnight in an LB culture medium containing ampicillin, and plasmid DNAs were prepared using QIAwell 8 Plasmid Kit (Qiagen). An aliquot of the DNAs thus prepared was digested with restriction enzymes ClaI and SpeI to confirm the size of the receptor DNA fragment inserted. Sequencing was carried out by usilig a DyeDeoxy Terminator Cycle Sequencing Kit (Applied Biosystems, Inc.), and the DNAs were decoded by using a fluorescent automatic sequencer (SEQ ID NO: 128). The pCR-Script Amp SK(+) plasmid, which retained DNA having the base sequence represented by SEQ ID NO:128, was named pCR-Script human GPR7. The amino acid sequence of human GPR7 encoded by the DNA having the base sequence represented by SEQ ID NO: 128 is represented by SEQ ID NO: 129. Also, the DNA sequence and amino acid sequence of human GPR7 are shown in FIG. 13. The DNA sequence of human GPR7 sequenced herein was different by 2 bases from the DNA sequence reported by O'Dowd et al. (O'Dowd, B. F. et al., Genomics, 28, 84-91, 1995). These 2 bases correspond to 893 and 894 bases in SEQ ID NO: 128, which are C and G according to the report by O'Dowd et al. and in this REFERENCE EXAMPLE, G and. C, respectively. Thus, the 296th amino acid of SEQ ID NO: 129 in the amino acid sequence translated, which reportedly corresponds to Thr in O'Dowd et al., is Ser in this EXAMPLE.

Reference Example 68

Preparation of CHO Cells Which Express Human GPR7

Using Plasmid Midi Kit (Qiagen), plasmid DNA was prepared from *Escherichia coli* clones transformed by the plasmid bearing the gene encoding the full-length amino acid sequence of human GPR7, which sequence was confirmed in REFERENCE EXAMPLE 67, having the ClaI and SpeI recognition sequences added at the 5' and 3' ends, respectively. The plasmid DNA was digested with restriction enzymes ClaI and SpeI to excise the insert DNA. The insert DNA was electrophoresed, excised from the agarose gel with a razor blade, ground into small pieces, then extracted with phenol and with phenol/chloroform, and precipitated in ethanol to recover the DNA. The insert DNA was added to vector plasmid pAKKO-111H (the same vector plasmid as pAKKO1.11H described in Hinuma, S., et al., Biochim. Biophys. Acta, 1219, 251-259, 1994) for animal cell expression, which was digested with ClaI and SpeI, followed by ligation using T4 ligase (TaKaRa Shuzo Co., Ltd.) to construct plasmid pAKKO-Human GPR7 for protein expression. *Escherichia coli* transformed by this plasmid pAKKO-Human GPR7 was named *Escherichia coli* DH5α/pAKKO-Human GPR7.

After *Escherichia coli* DH5α (Toyobo Co., Ltd.) transfected with pAKKO-Human GPR7 was cultured, pAKKO-Human GPR7 µlasmid DNA was prepared using Plasmid Midi Kit (Qiagen). Using CellPhect Transfection Kit (Amersham Pharmacia Biotech), the plasmid DNA was transfected to CHO dhfr⁻ cells in accordance with the protocol attached. DNA, 3 µg, was co-precipitated with calcium phosphate in suspension. The resulting suspension was added to a 6 cm-diameter Petri dish, in which 5×10$^5$ or 1×10$^6$ CHO dhfr⁻ cells had been seeded before 24 hours. The cells were cultured in MEMα medium containing 10% fetal calf serum for one day. After passage, the cells were cultured in nucleic acid-free MEMα selection medium containing 10% dialyzed fetal calf serum to select 24 clones of the transformant colony GPR8-expressed CHO cells, grown in the selection medium.

Reference Example 69

Determination of Expression Level of Human GPR7 Gene in the Human GPR7-expressed CHO Cell Line Using Taq-Man PCR The 24 clones of the human GPR7-expressed CHO cell line produced in accordance with REFERENCE EXAMPLE 68 were individually incubated in a 25 cm$^2$ flask. Using ISOGEN (Nippon Gene Co., Ltd.), the total RNA fraction was prepared from the cells grown. The total RNA fraction was treated with DNase I using MessageClean Kit (Gen Hunter, Inc.) to acquire the total RNA free of DNA.

Using the total RNA as a template, cDNA was synthesized by usingTaqMan Reverse Transcription Reagents Kit (Applied Biosystems, Inc.). The reaction solution was composed of 4 µg of the total RNA treated with DNase I, 1 µl of random primer, 4.4 µl of 25 mM MgCl$_2$ solution, 2 µl of 10 mM dNTP mix, 0.4 µl of RNase Inhibitor and 0.5 µl of reverse transcriptase, to which the buffer attached to the kit was added to make the total volume 20 µl. The reverse transcription was carried out under conditions at 25° C. for 10 minutes, 48° C. for 30 minutes and then 95° C. for 5 minutes, using Thermal Cycler (TaKaRa Shuzo Co., Ltd.).

Standard human GPR7 DNA was prepared by purifying the DNA amplified by PCR using full-length human GPR7 DNA as a template. The reaction solution was composed of 5 pg of pCR-Script human GPR7 described in REFERENCE EXAMPLE 67, 0.5 µM of synthetic DNA primer (SEQ ID NO:130), 0.5 µM of synthetic DNA primer (SEQ ID NO:131), 1.6 mM dNTPs, 2.5 mM MgCl$_2$ and 0.5 µl of LATaq polymerase (TaKaRa Shuzo Co., Ltd.), to which the buffer attached to the enzyme was added to make the total volume 50 μl. After heating at 94° C. for 120 seconds, amplification was carried out in 25 cycles of 94° C. for 30 seconds, 60° C. for 30 seconds and 72° C. for 60 seconds, using Thermal Cycler (PE Biosystems, Inc.). The amplified product was finally kept warm at 72° C. for 10 minutes. The PCR solution was separated by means of 0.8% agarose gel electrophoresis. After the band parts were excised with a razor blade, the DNA amplified by PCR was recovered using QIAquick PCR Purification Kit (Qiagen). In order to remove the primer DNAs and dNTPs intermingled in the PCR-amplified DNA solution, the DNA solution was passed through Chromospin Column 400 (CLONTECH, Inc.) for gel chromatography to obtain the amplified human GPR7 DNA elution fraction. Based on the amount of DNA calculated from the absorption of this amplified human GPR7 DNA solution at 260 nm and the base composition of human GPR7 DNA amplified, the number of DNA copies contained in the amplified human GPR7 DNA solution was calculated. The amplified human GPR7 DNA was used as standard human GPR7 DNA for TaqMan PCR for quantification.

The number of copies of human GPR7 gene expressed on the human GPR7 CHO cell line was determined by TaqMan PCR. The reaction solution for TaqMan PCR was composed of 1 μl of a reverse-transcribed cDNA solution diluted with distilled water to 100-fold or standard human GPR7 DNA solution having various copy numbers, 0.2 μM each of synthetic DNA primers (SEQ ID NO:132 and SEQ ID NO:133), and 0.2 μM of human GPR7 TaqMan probe [probe having the base sequence represented by SEQ ID NO:134 (Fam-TTCATCCTCA ACCTGGCCAT CGC-Tamra; wherein Fam and Tamra represent 6-carboxy-fluorescein and 6-carboxy-tetramethyl-rhodamine, respectively)], to which TaqMan Universal PCR Master Mix (Applied Biosystems, Inc.) was added to make the total volume 25 μl. PCR was carried out using ABI PRISM 7700 Sequence Detector System (Applied Biosystems, Inc.), by keeping warm at 50° C. for 2 minutes and at 95° C. for 10 minutes and then repeating 40 times the cycle set to include at 95° C. for 15 seconds and 60° C. for 60 seconds. The expression level of human GPR7 gene was computed on ABI PRISM 7700 SDS software. The number of cycles at the moment when the fluorescence intensity of the reporter reached the set level was taken on the ordinate and the logarithm of the number of copies of various standard human GPR7 DNA was taken on the abscissa to prepare a standard curve. The copy number of human GPR7 cDNA contained in the reverse-transcribed cDNA was calculated from the standard curve to determine the expression level of human GPR7 gene per 1 ng of the total RNA. Clone Nos. 7, 8 and 14 showing a high expression level of human GPR7 gene were selected as the cell lines wherein human GPR7 gene was highly expressed.

Reference Example 70

Determination of Intracellular cAMP Production Level Using the Human GPR7-expressed CHO Cells The human GPR7-expressed CHO cells, which were prepared in REFERENCE EXAMPLE 68 and selected as described in REFERENCE EXAMPLE 69, were seeded on a 24-well plate in 5×10$^4$ cells/well, followed by incubation for 48 hours. The cells were washed with a MEMα buffer (pH7.4) containing 0.2 mM 3-isobutyl-methylxanthine, 0.05% BSA (bovine serum albumin) and 20 mM HEPES (hereinafter the MEMα buffer (pH7.4) containing 0.2 mM 3-isobutyl-methylxanthine, 0.05% BSA and 20 mM HEPES is referred to as a reaction buffer). Thereafter, 0.5 ml of the reaction buffer was added to the cells, which was then kept warm in an incubator for 30 minutes. The reaction buffer was removed and after 0.25 ml of a fresh reaction buffer was replenished to the cells, a sample solution in DMSO having an appropriate concentration and 0.25 ml of the reaction buffer containing 2 μM of forskolin were added to the cells, followed by reacting at 37° C. for 30 minutes. The reaction was terminated by adding 100 μl of 20% perchloric acid. Next, the reaction mixture was put on ice for an hour to extract intracellular cAMP. The level of cAMP in the extract was determined by cAMP EIA Kit (Amersham Pharmacia Biotech).

Reference Example 71

(1) [Phe$^2$] Human GPR8 Ligand (1-20): Preparation of Trp-Phe-Lys-His-Val-Ala-Ser-Pro-Arg-Tyr-His-Thr-Val-Gly-Arg-Ala-Ala-Gly-Leu-Leu (SEQ ID NO:135)

Using a peptide automatic synthesizer (Model ABI 433) available from Applied Biosystems, Inc., the objective protected peptide resin was synthesized in accordance with the program to extend the peptide chains sequentially from the C terminus by the Fmoc technique.

Wang (p-benzyloxybenzyl alcohol) resin (0.25 mmol) was used as a starting amino acid resin carrier. Fmoc amino acid derivatives of Fmoc-Leu, Fmoc-Gly, Fmoc-Ala, Fmoc-Arg (Pbf), Fmoc-Val, Fmoc-Thr (Bu$^t$), Fmoc-His (Trt), Fmoc-Tyr (Bu$^t$), Fmoc-Pro, Fmoc-Ser (Bu$^t$), Fmoc-Lys (Boc), Fmoc-Phe and Fmoc-Trp (Boc) were sequentially condensed in the given order, using HBTU (2-(1H-benzotriazol-1-yl)-1,1,3,3-tetramethyluronium hexafluorophosphate).

After construction of the peptides onto the resin was completed, the protected peptide resin was dried. The resulting protected peptide was treated with TFA to split the protection off and separate the peptide from the resin carrier. The crude peptide obtained was extracted with 0.1% TFA-water and the extract was lyophilized to give a powdery solid. Subsequently, the crude peptide was subjected to preparative purification on reversed phase high performance chromatography (Shimadzu Corporation, preparative device: Model LC8A), using the acetonitrile-0.1% TFA water system (15-35%, 80 minutes). Thus, 35 mg of the objective purified peptide was obtained.

The purified peptide was hydrolyzed at 110° C. for 22 minutes with 4N methanesulfonic acid containing 0.2% 3-(2-aminoethyl)indole to give the hydrolysate. The product has the following analysis data for amino acids of the hydrolysate (calculated data within parenthesis).

Thr (1) 0.93, Ser (1) 0.92, Gly (2) 2.03, Ala (3) 3.09, Val (2) 1.90, Leu (2) 2.02, Tyr (1) 1.02, Phe (1) 1.00, His (2) 1.91, Lys (1) 0.98, Trp (1) 0.88, Arg (2) 2.06, Pro (1) 1.02

The purity was found on HPLC to be 98.8%. Mass spectrum data was 2266.6 (calcd. 2266.6).

(2) Preparation of [Phe$^2$,$^{125}$I-Tyr$^{10}$] Human GPR8 Ligand (1-20) Using the Lactoperoxidase Method A solution of 10 nmol [Phe$^2$] human GPR8 ligand (1-20) (SEQ ID NO:135) obtained by a modification of the process described in (1) above, in 10 μl of DMSO was mixed with 10 μl of 0.1 M nickel chloride aqueous solution, 10 μl of 0.001% hydrogen peroxide aqueous solution, 10 μg/ml of lactoperoxidase (Sigma, Inc.) dissolved in 0.1 M HEPES (pH 7.6) and 10 μl of [$^{125}$I] NaI 40 MBq (NEN LIFE SCIENCE PRODUCTS, LTD.). After the mixture was reacted at room temperature for 50 minutes, the product, [Phe$^2$, $^{125}$I-Tyr$^{10}$] human GPR8 ligand (1-20), was fractionated on HPLC under the following conditions.

Using ODS-80TM (4.6 mm×15 cm) (Toso Co., Ltd.) as a column and 10% acetonitrile/0.1% TFA as eluant A and 60% acetonitrile/0.1% TFA as eluant B, the product was subjected to gradient elution of 0-0 (2 min), 0-27 (5 min), 27-32 (40 min) % B/A+B (60 mins.). The flow rate was 1 ml/min and the column temperature was 40° C., and detection was made at 215 nm. Under the HPLC conditions, [Phe$^2$, $^{125}$I-Tyr$^{10}$] human GPR8 ligand (1-20) was eluted around 25 minutes.

Example 1

Figure 14:
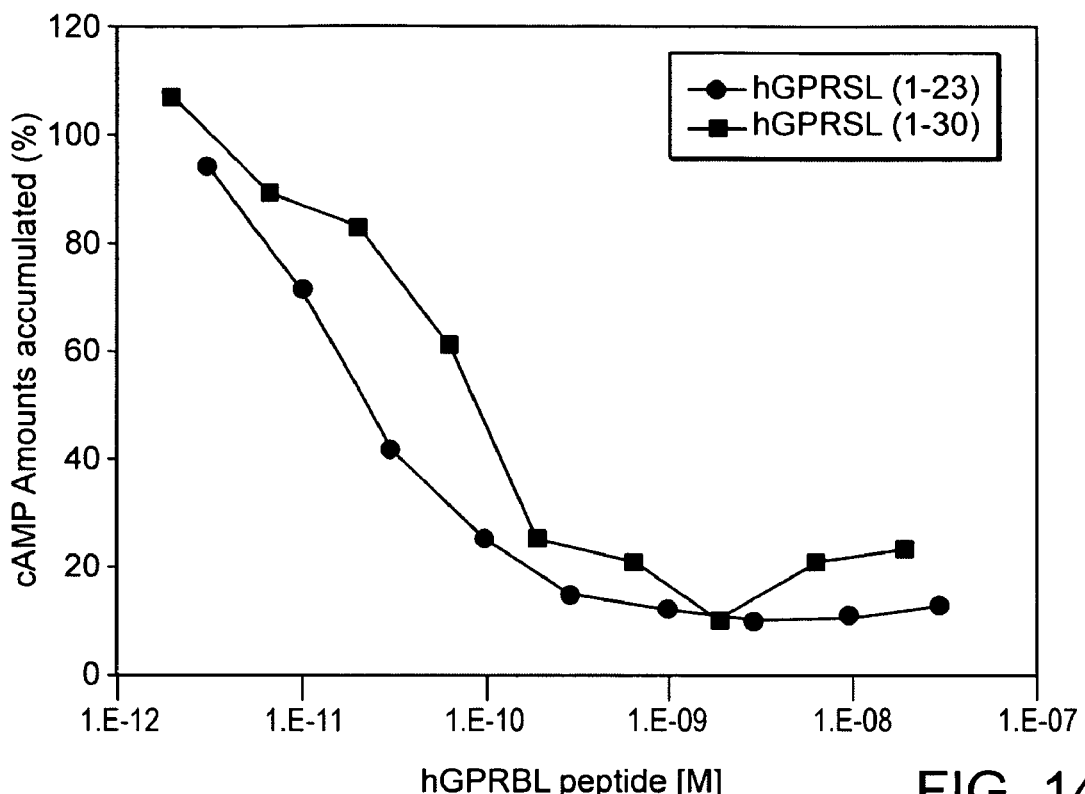
FIG. 14 shows the cAMP production suppressing activity of GPR8 ligand peptides composed of 23 residues and 30 residues in various concentrations on human homologue CHO/GPR7 cells.

Intracellular cAMP Production Suppressing Activity of GPR8 Ligand Peptide Human Homologs of 23 Residues or 30 Residues, Assayed Using the Human GPR7-expressed CHO Cells Following the method described in REFERENCE EXAMPLE 70, hGPR8L (1-23) (SEQ ID NO:16) or hGPR8L (1-30) (SEQ ID NO:17) was given to the human GPR7-expressed CHO cells in various concentrations to determine the intracellular cAMP production suppressing activity. The results are shown in FIG. 14, wherein the cAMP synthesis suppressing activity is expressed by the value in terms of % of the intracellular cAMP level, which was obtained by subtracting the intracellular cAMP level accumulated where hGPR8L (1-23) or hGPR8L (1-30) was added, from the intracellular cAMP level accumulated where the reaction buffer was added, taking as 100% the intracellular cAMP level obtained by subtracting the intracellular cAMP level accumulated where the reaction buffer was added, from the intracellular cAMP level accumulated where the reaction buffer containing forskolin was added.

Obviously, hGPR8L (1-23) and hGPR81, (1-30) suppressed the intracellular cAMP production dose-dependently in the human GPR7-expressed CHO cells. This revealed that hGPR8L (1-23) and hGPR8L (1-30) were ligands to the human GPR7. When 50% inhibitory concentration (IC$_{50}$) was determined from the cAMP production level, the IC$_{50}$ values of hGPR8L (1-23) and hGPR8L (1-30) were 0.025 nM and 0.13 nM, respectively.

It could also be verified that a similar reaction in the human GPR7-expressed CHO cells to the reaction described above occurred when using porcine, rat and mouse homologs (SEQ ID NO:56, SEQ ID NO:73 and SEQ ID NO:91) to hGPR8L (1-23) and porcine, rat and mouse homologs (SEQ ID NO:57, SEQ ID NO:74 and SEQ ID NO:92) to hGPR8L (1-30).

Example 2

Receptor Binding Test Using [$^{125}$I-Tyr$^{10}$]-hGPR8L (1-23)

Receptor binding test was carried out using [$^{125}$I-Tyr$^{10}$]-hGPR8L (1-23) prepared as described in REFERENCE EXAMPLE 42 and the cell membrane fraction prepared from the human GPR7-expressed CHO cells.

First, preparation of the membrane fraction is described below.

To 1×10$^8$ of the human GPR7-expressed CHO cells was added 10 ml of a homogenate buffer (10 mM NaHCO$_3$, 5 mM EDTA (ethylenediaminetetraacetic acid), 0.5 mM PMSF (phenylmethanesulfonyl fluoride), 1 µg/ml pepstatin, 4 µg/ml E64 and 20 µg/ml leupeptin). The mixture was homogenized by using Polytron (12,000 rpm, 1 min.). The cell homogenate was centrifuged (1,000 g, 15 mins.) to obtain the supernatant. Next, the supernatant was subjected to ultracentrifugation (Beckman type 30 rotor, 30,000 rpm, 1 hour). The resulting precipitate was used as a human GPR7-expressed CHO cell membrane fraction.

The thus prepared cell membrane fraction was diluted in various concentrations with an assay buffer (25 mM Tris-HCl, 5 mM EDTA, 0.05% CHAPS (3-[(3-choramidopropyl) dimethylammonio]-1-propanesulfonate), 0.1% BSA, 0.5 mM PMSF, 1 µg/ml pepstatin, 20 µg/ml leupeptin and 4 µg/ml E-64, pH 7.4). Then, a 200 µl aliquot of the dilution was dispensed into a propylene-made testing tube (Falcon 2053). In order to assay for the total binding, 2 µl of DMSO and 2 µl of 8 nM [$^{125}$I-Tyr$^{10}$]-hGPR8L (1-23) was added to the membrane fraction solution. Also, the non-specific binding was assayed by adding 2 µl of a DMSO solution of 1 mM hGPR8L (1-23) and 2 µl of 8 nM [$^{125}$I-Tyr$^{10}$]-hGPR8L (1-23) to the membrane fraction solution. After reacting at 25° C. for 75 minutes, the reaction solution was suction-filtrated through a polyethyleneimine-treated Whatman glass filter (GF-F), and the filter was washed twice with ~1.5 ml of a wash buffer (25 mM Tris-HCl, 5 mM EDTA, 0.05% CHAPS, 0.1% BSA, pH 7.4). After the filtration, the residual radioactivity remained on the filter paper was measured with a γ-counter, and the specific binding was estimated by subtracting the non-specific binding from the total binding.

When the concentration of membrane fraction was varied, it was shown that the specific binding of [$^{125}$I-Tyr$^{10}$]-hGPR8L (1-23) was dependent on the concentration of the membrane fraction. Also, the concentration of the membrane fraction was set at 10 µg/ml, and the binding inhibition of [$^{125}$I-Tyr$^{10}$]-hGPR8L (1-23) against the human GPR7-expressed cell membrane fraction by hGPR8L (1-23) and hGPR8L (1-30) was examined. The 50% inhibitory concentration (IC$_{50}$ value) was calculated from the inhibition rate. The IC$_{50}$ value of hGPR8L (1-23) was found to be 0.099 nM. Also, the IC$_{50}$ value of hGPR8L (1-30) was found to be 0.025 nM.

Figure 15:
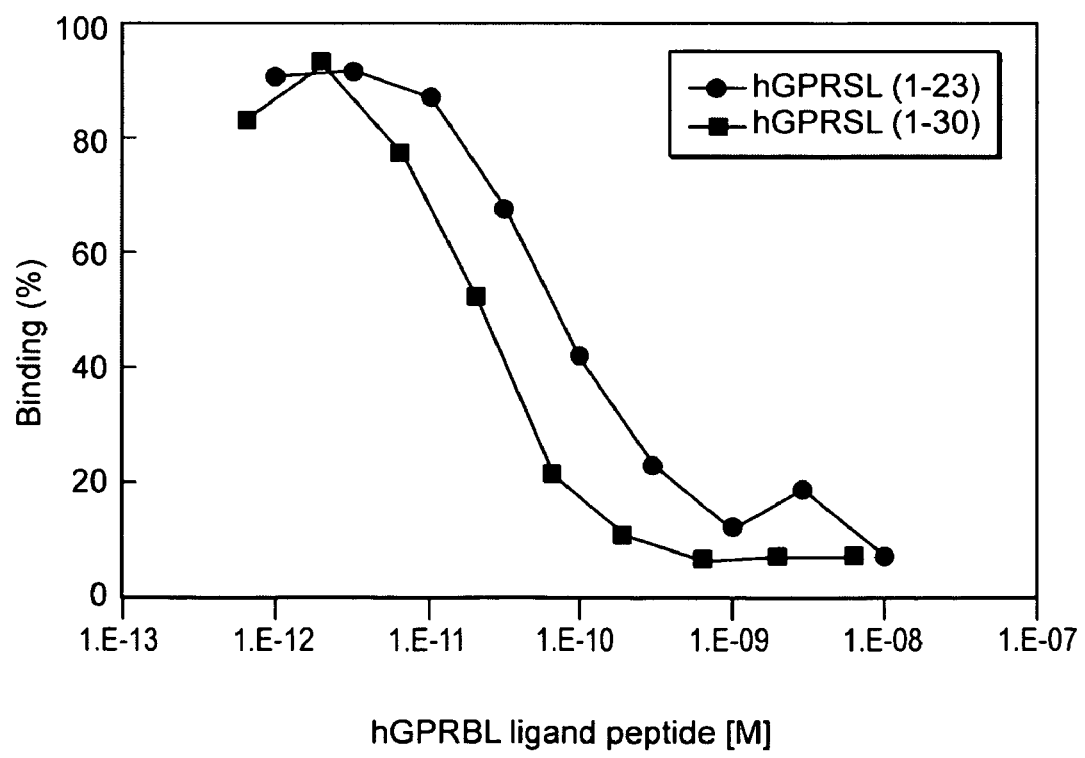
FIG. 15 is a graph showing the binding inhibitory activity of hGPR8L (1-23) and hGPR8L (1-30) in various concentrations on the cell membrane fraction prepared from human GPR7-expressed CHO cells of [$^{125}$I]-labeled human GPR8 ligand of 23 residues, using a cell membrane fraction prepared from human GPR8-expressed CHO cells.

The results indicate that hGPR8L (1-23) and hGPR8L (1-30) had a high affinity to the human GPR7-expressed cell membrane fraction, meaning that hGPR8L (1-23) and hGPR8L (1-30) are ligands of high affinity to the human GPR7 receptor. FIG. 15 shows the binding inhibition of hGPR8L (1-23) and hGPR8L (1-30) in various concentrations.

It could also be verified that the binding inhibition of [$^{125}$I-Tyr$^{10}$]-hGPR8L (1-23) against the human GPR7-expressed CHO cell membrane fraction was noted as described above, when rat and mouse homologs (SEQ ID NO:73 and SEQ ID NO:91) to hGPR8L (1-23) and porcine, rat and mouse homologs (SEQ ID NO:57, SEQ ID NO:74 and SEQ ID NO:92) to hGPR8L (1-30).

Example 3

1) Assay for GTPγS-Binding Activity Using the Membrane Fraction of the GPR7-expressed CHO Cells The [$^{35}$S]-guanosine 5'-(γ-thio)triphosphate (GTPγS) binding promoting activity on the GPR7-expressed CHO cell membrane fraction was assayed by the following procedures.

The GPR7-expressed CHO cell membrane fraction prepared by the method described in EXAMPLE 2 was diluted with a membrane dilution buffer (50 mM Tris-hydrochloride buffer (pH 7.4), 5 mM MgCl$_2$, 150 mM NaCl, 1 µM GDP and 0.1% BSA) to prepare a cell membrane fraction solution for assay having a protein level of 30 µg/ml. To 200 µl of the cell membrane fraction solution for assay were added 2 µl of 50 nM [$^{35}$S]-guanosine 5'-(γ-thio)triphosphate (NEN Co.) and 2 µl of a sample solution in DMSO, which was adjusted to an appropriate concentration. The resulting mixture was kept warm at 25° C. for an hour. The mixture was filtrated through a filter. After the filter was washed twice with 1.5 ml of a wash buffer (50 mM Tris-hydrochloride buffer (pH 7.4), 5 mM MgCl$_2$, 1 mM EDTA and 0.1% BSA), radioactivity of the filter was measured with a liquid scintillation counter.

2) GTPγS-Binding Promoting Activity of hGPR8L (1-23) or hGPR8L (1-30) Assayed Using the GPR7-expressed CHO Cell Membrane Fraction Following the procedures described in 1) above, hGPR8L (1-23) or hGPR8L (1-30) were given to the GPR7-expressed CHO cell membrane fraction in various concentrations to assay for the GTPγS-binding promoting activity.

Figure 16:
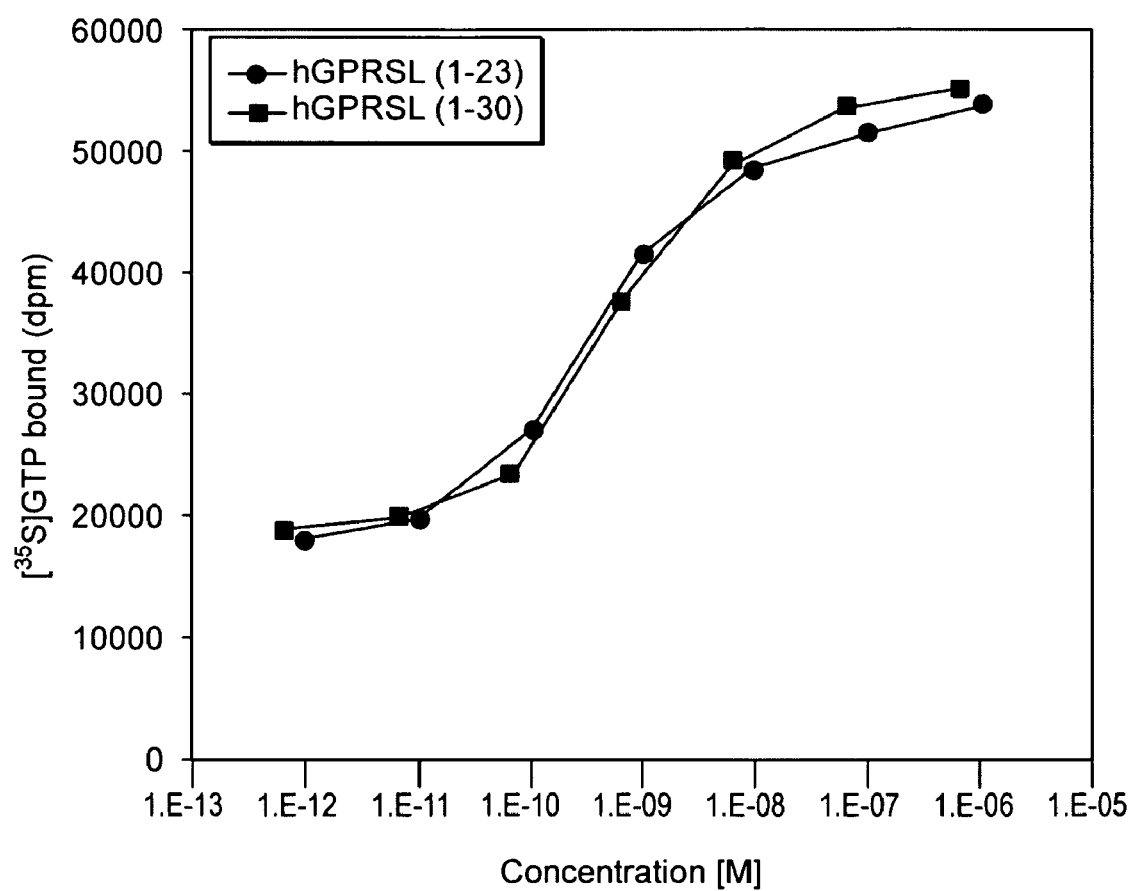
FIG. 16 is a graph showing the GTPγ S binding promoting activity of hGPR8L (1-23) on the CHO/GPR7 cell membrane fraction, wherein symbols -●- and -■- designate data obtained by administering hGPR8L (1-23) and hGPR8L (1-30), respectively.

The results are shown in FIG. 16.

Obviously, hGPR8L (1-23) and hGPR8L (1-30) suppressed the intracellular cAMP production dose-dependently in the GPR7-expressed CHO cells.

The 50% effective concentration (EC$_{50}$ value) was calculated from the GTPγS-binding promoting activity. The EC$_{50}$ value of hGPR8L (1-23) was found to be 0.74 nM. Also, the EC$_{50}$ value of hGPR8L (1-30) was found to be 0.67 nM (TABLE 2).

It could also be verified that the reaction of the human GPR7-expressed CHO cells occurred as described above, when using rat and mouse homologs (SEQ ID NO:73 and SEQ ID NO:91) to hGPR8L (1-23) and porcine, rat and mouse homologs (SEQ ID NO:57, SEQ ID NO:74 and SEQ ID NO:92) to hGPR8L (1-30).

Example 4

GTPγS-Binding Promoting Activity of Human and Porcine Homolog Derivatives of GPR8 Ligand Peptides Assayed Using the GPR7-expressed CHO Cell Membrane Fraction Following the procedures described in EXAMPLE 3, human and porcine homolog derivatives of the GPR8 ligand peptides obtained in REFERENCE EXAMPLES were administered to the GPR7-expressed CHO cell membrane fraction in various concentrations to assay for the GTPγS-binding promoting activity.

The sequence identification numbers and GTPγS-binding promoting activity of the derivatives assayed are shown in TABLE 2, wherein the activity is expressed in terms of the 50% effective concentration (EC$_{50}$).

TABLE 2

GTPγS-Binding promoting activity and receptor binding activity of human and porcine homolog derivatives of GPR8 ligand peptides

| Derivative | SEQ ID NO: | GTPγS-Binding promoting activity (EC$_{50}$ nM) | Receptor binding activity (IC$_{50}$ nM) |
|---|---|---|---|
| hGPR8L (1–23) | 16 | 0.74 | 0.072 |
| hGPR8L (1–30) | 17 | 0.67 | 0.025 |
| [Met(O)]-hGPR8L (1–23) | 95 | 1.6 | 0.17 |
| Fmoc-hGPR8L (1–23) | 105 | 6.6 | 0.14 |
| Ac-hGPR8L (1–23) | 106 | 1.5 | 0.077 |
| [D-Trp$^1$]-hGPR8L (1–23) | 112 | 2.3 | 0.63 |
| hGPR8L (2–23) | 107 | 7410 | 140 |
| Ac-hGPR8L (2–23) | 111 | 7000 | 570 |
| IndPr-hGPR8L (2–23) | 113 | 0.85 | 0.044 |
| hGPR8L (4–23) | 108 | >10000 | 1200 |
| hGPR8L (9–23) | 109 | >10000 | 2200 |
| hGPR8L (1–20) | 98 | 0.88 | 0.094 |
| hGPR8L (1–19) | 99 | 84 | 1.7 |
| hGPR8L (1–18) | 100 | 6200 | 2400 |
| pGPR8L (1–23) | 56 | 0.35 | 0.066 |
| [Met(O)]-pGPR8L (1–23) | 103 | 1.2 | 0.22 |

Example 5

Receptor Binding Activity of Human and Porcine Homolog Derivatives of GPR8 Ligand Peptides Assayed Using GPR7-expressed CHO cell Membrane Fraction and [$^{125}$I-Tyr$^{10}$]-hGPR8L (1-23)

Following the procedures described in EXAMPLE 2, human and porcine homolog derivatives of the GPR8 ligand peptides obtained in REFERENCE EXAMPLES were assayed for the receptor binding activity, using the GPR7-expressed CHO cell membrane fraction and [$^{125}$I-Tyr$^{10}$]-hGPR8L (1-23).

The sequence identification numbers and receptor binding activity of the derivatives assayed are shown in TABLE 2, wherein the activity is expressed in terms of 50% inhibitory concentration (IC$_{50}$).

Example 6

Screening of a Compound that Alters the Binding of [Phe$^2$, $^{125}$I-Tyr$^{10}$] Human GPR8 Ligand (1-20) to Human GPR Receptor binding test is carried out using [Phe$^2$,$^{125}$I-Tyr$^{10}$] human GPR8 ligand (1-20) prepared by the procedures described in REFERENCE EXAMPLE 71 and the GPR7-expressed CHO cell membrane fraction prepared by the procedures described in EXAMPLE 2, whereby the binding inhibitory activity of a test compound can be assayed.

The cell membrane fraction prepared from the GPR7-expressed CHO cells was diluted to 15 µg/ml with an assay buffer (25 mM Tris-HCl, 5 mM EDTA, 0.05% CHAPS, 0.1% BSA, 0.5 mM PMSF, 1 µg/ml pepstatin, 4 µg/ml E-64 and 20 µg/ml leupeptin, pH 7.4). Then, a 200 µl aliquot of the dilution was dispensed in a propylene-made testing tube (Falcon 2053). In order to assay for the total binding, 2 µl of DMSO and 2 µl of the assay buffer for 7 nM [Phe$^2$,$^{125}$I-Tyr$^{10}$] human GPR8 ligand (1-20) were added to the membrane fraction solution. Also, to assay for non-specific binding, 2 µl of a DMSO solution of 100 µM human GPR8 ligand (1-23) and 2 µl of the assay buffer for 7 nM [Phe$^2$,$^{125}$I-Tyr$^{10}$] human GPR8 ligand (1-20) were added to the membrane fraction solution. Moreover, 2 µl of a DMSO solution of a test compound diluted in various concentrations and 2 µl of the assay buffer for 7 nM [Phe$^2$,$^{125}$-Tyr$^{10}$] human GPR8 ligand (1-20) were added to the membrane fraction solution to assay for the binding inhibitory activity of the test compound. After reacting at 25° C. for 75 minutes, the reaction solution was suction-filtrated through a polyethyleneimine-treated Whatman glass filter (GF/F). After the filtration, the residual radioactivity remained on the filter paper was measured with a γ-counter, and the specific binding was estimated by subtracting the non-specific binding from the total binding. The binding inhibitory activity (inhibition rate, %) of the test compound against the GPR7 receptor is expressed in terms of a percentage ((TB-X)/SB×100 (%)), which is a ratio of the radioactivity obtained by subtracting from the total binding (TB) the radioactivity (X) remained on the filter paper when the test compound and [$Phe^2,^{125}I-Tyr^{10}$] human GPR8 ligand (1-20) were added, to the receptor.

Example 7

Screening of a Compound that Alters the Intracellular cAMP Production Suppressing Activity of Human GPR8 Ligand in the Human GPR7-expressed Cells Following the procedures described in REFERENCE EXAMPLE 70, a compound that alters the intracellular cAMP production suppressing activity of human GPR8 ligand in the human GPR7-expressed cells can be screened by administering 2 μl of 250 nM human GPR8 ligand (1-23) (SEQ ID NO:16) as a reaction buffer and 2 μl of a DMSO solution of the test compound in various concentrations simultaneously to the human GPR7-expressed CHO cells.

The activity of the test compound on the cAMP production suppressing activity of the human GPR8 ligand in the human GPR7-expressed cells is expressed in terms of % of the intracellular cAMP level, which is obtained by subtracting the intracellular cAMP level accumulated where the human GPR8 ligand and the test compound are added, from the intracellular cAMP level accumulated where the reaction buffer containing forskolin was added, taking as 100% the intracellular cAMP level obtained by subtracting the intracellular cAMP level accumulated where the human GPR8 ligand alone was added, from the intracellular cAMP level accumulated where the reaction buffer containing forskolin was added. When the test compound suppresses the action of human GPR8 ligand, the percentage becomes 100% or less, whereas the percentage becomes 100% or more when the test compound potentiates the action of human GPR8 ligand.

Example 8

Screening of a Compound that Alters the GTPγS-Binding Promoting Activity of Human GPR8 Ligand to the Human GPR7-expressed Cell Membrane Fraction Following the procedures described in EXAMPLE 3, a compound that alters the GTPγS-binding promoting activity of human GPR8 ligand to the human GPR7-expressed cell membrane fraction can be screened by administering 2 μl of a DMSO solution of 100 nM human GPR8 ligand (1-23) (SEQ ID NO:16) as a reaction buffer and 2 μl of a DMSO solution of the test compound in various concentrations simultaneously to the membrane fraction solution for the purpose of assay, which was prepared from the human GPR7-expressed CHO cells.

The activity of the test compound on the GTPγS-binding promoting activity of human GPR8 ligand in the human GPR7-expressed cell membrane fraction is expressed in terms of a percentage of the radioactivity obtained by subtracting the radioactivity when 2 μl of DMSO alone is added, from the radioactivity when the human GPR8 ligand and the test compound are added, taking as 100% the radioactivity obtained by subtracting the radioactivity when 2 μl of DMSO alone is added, from the radioactivity when the human GPR8 ligand is added. When the test compound suppresses the action of human GPR8 ligand, the percentage becomes 100% or less, whereas the percentage becomes 100% or more when the test compound potentiates the action of human GPR8 ligand.

INDUSTRIAL APPLICABILITY

The compounds or salts thereof, which are obtainable using the screening methods or screening kits of the present invention, are low toxic and useful as, for example, preventive/therapeutic agents for anorexia nervosa, appetite (eating) stimulants, preventive/therapeutic agents for obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], preventive/therapeutic agents for hyperphagia, etc. Among them, the receptor antagonists of the present invention are useful as antiobesity agents. Furthermore, the receptors of the present invention, the polynucleotides encoding the receptors are useful as, e.g., preventive/therapeutic agents for anorexia nervosa, appetite (eating) stimulants, etc. The polynucleotides encoding the receptors of the present invention are useful for diagnosis of anorexia nervosa or obesity. Moreover, the antibodies and antisense nucleotides to the receptors of the present invention are useful as antiobesity agents and diagnostics.

The invention claimed is:

1. A method of screening a compound or its salt that alters the binding property between (1) a receptor protein or its salt containing an amino acid sequences of SEQ ID NO: 129 and (2) a polypeptide which specifically binds to the receptor protein, or its amide or ester, or a salt thereof, which method comprises:
   (i) contacting the polypeptide or its amide or ester, or a salt thereof with the receptor protein or its salt,
   (ii) contacting the polypeptide or its amide or ester, or a salt thereof and a test compound with the receptor protein or its salt, and
   (iii) (a) a binding amount of the polypeptide, or its amide or ester, or a salt thereof to the receptor protein or its salt of the (i) and (ii), or (b) a cell-stimulating activity of the (i) and (ii) is assayed and compared.

2. The method of screening according to claim 1, wherein the polypeptide is a polypeptide consisting of the amino acid sequence of SEQ ID NO: 16, SEQ ID NO: 17, SEQ ID NO:56, SEQ ID NO: 95, SEQ ID NO:98, SEQ ID NO: 99, SEQ ID NO:103, SEQ ID NO:105, SEQ ID NO:106, SEQ ID NO:112 SEQ ID NO:113.

3. A kit for screening a compound or its salt that alters the binding property between (1) a protein or its salt containing an amino acid sequence represented by SEQ ID NO:129 and (2) a polypeptide which specifically binds to the protein, or its amide or ester, or a salt thereof, comprising (1) the protein or its salt and (2) the polypeptide or its amide or ester, or a salt thereof.

4. The method of screening according to claim 1, wherein the compound or its salt to be screened is for preventing or treating obesity.

* * * * *

SEQUENCE LISTING

<160> NUMBER OF SEQ ID NOS: 135

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1

```
atcgattaca atgcaggccg ctgggcaccc ag                                32
```

```
<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
actagtgccc ttcagcaccg caatatgctg cg                                32

<210> SEQ ID NO 3
<211> LENGTH: 1023
<212> TYPE: DNA
<213> ORGANISM: Human

<400> SEQUENCE: 3
atcgattaca atgcaggccg ctgggcaccc agagccccatt gacagcaggg gctccttctc    60
cctccccacg atgggtgcca acgtctctca ggacaatggc actggccaca atgccacctt   120
ctccgagcca ctgccgttcc tctatgtgct cctgcccgcc gtgtactccg ggatctgtgc   180
tgtggggctg actggcaaca cggccgtcat ccttgtaatc ctaagggcgc ccaagatgaa   240
gacggtgacc aacgtgttca tcctgaacct ggccgtcgcc gacgggctct tcacgctggt   300
actgcccgtc aacatcgcgg agcacctgct gcagtactgg cccttcgggg agctgctctg   360
caagctggtg ctggccgtcg accactacaa catcttctcc agcatctact tcctagccgt   420
gatgagcgtg gaccgatacc tggtggtgct ggccaccgtg aggtcccgcc acatgccctg   480
gcgcacctac cgggggggcga aggtcgccag cctgtgtgtc tggctgggcg tcacggtcct   540
ggttctgccc ttcttctctt cgctggcgt ctacagcaac gagctgcagg tcccaagctg   600
tgggctgagc ttcccgtggc ccgagcaggt ctggttcaag gccagccgtg tctacacgtt   660
ggtcctgggc ttcgtgctgc ccgtgtgcac catctgtgtg ctctacacag acctcctgcg   720
caggctgcgg gccgtgcggc tccgctctgg agccaaggct ctaggcaagg ccaggcggaa   780
ggtgaccgtc ctggtcctcg tcgtgctggc cgtgtgcctc ctctgctgga cgcccttcca   840
cctggcctct gtcgtggccc tgaccacgga cctgccccag accccactgg tcatcagtat   900
gtcctacgtc atcaccagcc tcagctacgc caactcgtgc ctgaaccccc tcctctacgc   960 cttttctagat gacaacttcc ggaagaactt ccgcagcata ttgcggtgct gaagggcact  1020
agt                                                                1023

<210> SEQ ID NO 4
<211> LENGTH: 333
<212> TYPE: PRT
<213> ORGANISM: Human

<400> SEQUENCE: 4

Met Gln Ala Ala Gly His Pro Glu Pro Leu Asp Ser Arg Gly Ser Phe
  1               5                  10                  15

Ser Leu Pro Thr Met Gly Ala Asn Val Ser Gln Asp Asn Gly Thr Gly
             20                  25                  30

His Asn Ala Thr Phe Ser Glu Pro Leu Pro Phe Leu Tyr Val Leu Leu
         35                  40                  45

Pro Ala Val Tyr Ser Gly Ile Cys Ala Val Gly Leu Thr Gly Asn Thr
     50                  55                  60
```

```
Ala Val Ile Leu Val Ile Leu Arg Ala Pro Lys Met Lys Thr Val Thr
 65                  70                  75                  80

Asn Val Phe Ile Leu Asn Leu Ala Val Ala Asp Gly Leu Phe Thr Leu
                 85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
            115                 120                 125

Phe Ser Ser Ile Tyr Phe Leu Ala Val Met Ser Val Asp Arg Tyr Leu
130                 135                 140

Val Val Leu Ala Thr Val Arg Ser Arg His Met Pro Trp Arg Thr Tyr
145                 150                 155                 160

Arg Gly Ala Lys Val Ala Ser Leu Cys Val Trp Leu Gly Val Thr Val
                165                 170                 175

Leu Val Leu Pro Phe Phe Ser Phe Ala Gly Val Tyr Ser Asn Glu Leu
            180                 185                 190

Gln Val Pro Ser Cys Gly Leu Ser Phe Pro Trp Pro Glu Gln Val Trp
            195                 200                 205

Phe Lys Ala Ser Arg Val Tyr Thr Leu Val Leu Gly Phe Val Leu Pro
210                 215                 220

Val Cys Thr Ile Cys Val Leu Tyr Thr Asp Leu Leu Arg Arg Leu Arg
225                 230                 235                 240

Ala Val Arg Leu Arg Ser Gly Ala Lys Ala Leu Gly Lys Ala Arg Arg
                245                 250                 255

Lys Val Thr Val Leu Val Leu Val Leu Ala Val Cys Leu Leu Cys
                260                 265                 270

Trp Thr Pro Phe His Leu Ala Ser Val Val Ala Leu Thr Thr Asp Leu
            275                 280                 285

Pro Gln Thr Pro Leu Val Ile Ser Met Ser Tyr Val Ile Thr Ser Leu
            290                 295                 300

Ser Tyr Ala Asn Ser Cys Leu Asn Pro Phe Leu Tyr Ala Phe Leu Asp
305                 310                 315                 320

Asp Asn Phe Arg Lys Asn Phe Arg Ser Ile Leu Arg Cys
                325                 330
```

```
<210> SEQ ID NO 5
<211> LENGTH: 687
<212> TYPE: RNA
<213> ORGANISM: Artificial Sequence
<220> FEATURE:
<223> OTHER INFORMATION: Riboprobe

<400> SEQUENCE: 5
caaaagcugg agcuccaccg cgguggcggc cgcucuagcc cacuagugcc cuucagcacc    60
gcaauaugcu gcggaaguuc uuccggaagu ugucaucuag aaaggcguag aggaaggggu   120
ucaggcacga guuggcguag cugaggcugg ugaugacgua ggacauacug augaccagug   180 ggguucugggg caggucccgug gucagggcca cgacagaggc caggugggaag ggcguccagc   240 agaggaggca cacggccagc acgacgagga ccaggacggu caccuuccgc cuggccuugc   300
cuagagccuu ggcuccagag cggagccgca cggcccgcag ccugcgcagg aggucugugu   360
agagcacaca gauggugcac acgggcagca cgaagcccag gaccaacgug uagacacggc   420
uggccuugaa ccagaccugc ucgggccacg ggaagcucag cccacagcuu gggaccugca   480
gcucguugcu guagacgcca gcgaaagaga agaagggcag aaccaggacc gugacgccca   540
```

```
gccagacaca caggcuggcg accuucgccc cccgguaggu gcgccagggc auguggcggg      600
accucacggu ggccagcacc accagguauc gguccacgcu caucacggcu aggaaguaga      660
ugcuggagaa gauguuguag ggucga                                          687
```

<210> SEQ ID NO 6
<211> LENGTH: 17
<212> TYPE: PRT
<213> ORGANISM: Porcine

<400> SEQUENCE: 6

```
Trp Tyr Lys His Thr Ala Ser Pro Arg Tyr His Thr Val Gly Arg Ala
1               5                   10                  15

Ala
```

<210> SEQ ID NO 7
<211> LENGTH: 438
<212> TYPE: DNA
<213> ORGANISM: Human
<220> FEATURE:
<221> NAME/KEY: variation
<222> LOCATION: 408
<223> OTHER INFORMATION: n means a, t, g or c.

<400> SEQUENCE: 7

```
gccccatgag caggccagcg gcgcggccca ccgtgtggta gcggggactc gccacgtgct       60
tgtaccacgc gccggagggc agcgcagca ggagcagaag cagcagcagt gccagccgcg      120
gccggctcgc gggagccccc cgctcccctg gcgccacgc cagggcgctc gcgtcgacgg      180
ccgcccggcg gggcgggcca cgaaccggct cggctggggt tgggcgcgca gtggagttgg      240
gacgcccagg taccggagcg caggaggctg gaggcgagcc gtgggtcccc tgcaggccca      300
gctataaccg ctcggtggcc ccgcctcgtt ccgcccctc agtaccgctg ggctccccag       360 atgggggag ggacggaggg aggagaggga accctggcag ctggcggngg acgtgggtac       420
ttgagcacct cactgagt                                                    438
```

<210> SEQ ID NO 8
<211> LENGTH: 264
<212> TYPE: DNA
<213> ORGANISM: Human

<400> SEQUENCE: 8

```
gatagggtga gcgacgcagc cccatgagca ggccagcggc gcggcccacc gtgtggtagc       60
ggggactcgc cacgtgcttg taccacgcgc cggagggcag cggcagcagg agcagaagca      120
gcagcagtgc cagccgcggc cggctcgcgg gagcccccg ctcccctggg cgccacgcca       180
gggcgctcgc gtcgacggcc gccggcggg gcgggccacg aaccggctcg gctgggtttg       240
ggcgcgcagt ggagttggga cgcc                                             264
```

<210> SEQ ID NO 9
<211> LENGTH: 424
<212> TYPE: DNA
<213> ORGANISM: Human

<400> SEQUENCE: 9

```
gatagggtga gcgacgcagc cccatgagca ggccagcggc gcggcccacc gtgtggtagc       60
ggggactcgc cacgtgcttg taccacgcgc cggagggcag cggcagcagg agcagaagca      120
gcagcagtgc cagccgcggc cggctcgcgg gagcccccg ctcccctggg cgccacgcca       180
```

```
gggcgctcgc gtcgacggcc gcccggcggg gcgggccacg aaccggctcg gctgggtttg      240
ggcgcgcagt ggagttggga cgcccaggta ccggagcgca ggaggctgga ggcgagccgt      300
gggtcccctg caggcccagc tataaccgct cggtggcccc gcctcgttcc gcccctcag      360 taccgctggg ctccccagat ggggggaggg acggagggag gagagggaac cctggcagct      420
ggcg                                                                   424
```

<210> SEQ ID NO 10
<211> LENGTH: 375
<212> TYPE: DNA
<213> ORGANISM: Human

<400> SEQUENCE: 10

```
gcgcctcacc gtgtggtagc ggggactcgc cacgtgcttg taccacgcgc cggaggcagc       60
ggcacgagga gcagaagcag cagcagtgcc agccgcggcc ggctcgcggg agcccccgc       120 tcccctgggc gccacgcagg gctacagcgt cgacggccgc ccgcggggcc atcgcaaccg      180
gctcggctgg gtttgggcgc gcagtggagt tgggacgccc aggtaccgga gcgcaggagg      240
ctggaggcga gccgtgggtc ccctgcaggc ccagctataa ccgctcggtg gccccgcctc      300
gttccgcccc ctcagtaccg ctgggctccc cagaatgggg gagggacgga gggaggagag      360
ggaaccctgg cagct                                                       375
```

<210> SEQ ID NO 11
<211> LENGTH: 260
<212> TYPE: DNA
<213> ORGANISM: Human
<220> FEATURE:
<221> NAME/KEY: variation
<222> LOCATION: 2, 61, 147, 189, 213, 237, 249
<223> OTHER INFORMATION: n means a, t, g or c.

<400> SEQUENCE: 11

```
cnacgttctc ggggacataa accctgttct tgtcctaacc cgccaagggg ccatggactt       60
nagcgcgctg gcgtcgagca gagaagtacg ggggccctggg ccggggctcc ggtgaaccgg      120
cccctgctac cgctactgct gcttctnctc ttgctacctc tgcccgccag cgcctggtac      180
aagcacgtng cgagccctcg ctatcacaca gtnggtcgtg cctccgggct gctcatnggg      240
ctgcgccgnt cgtcctacct                                                  260
```

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12

```
aactccactg cgcgcccaaa ccca                                              24
```

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13

```
tctcccacag ctcctgaacc cacg                                              24
```

-continued

<210> SEQ ID NO 14
<211> LENGTH: 375
<212> TYPE: DNA
<213> ORGANISM: Human

<400> SEQUENCE: 14

```
aactccactg cgcgcccaaa cccagccgag ccggttcgtg gcccgccccg ccgggcggcc      60
gtcgacgcga gcgccctggc gtggcgccca ggggagcggg gggctcccgc gagcggccg     120 cggctggcac tgctgctgct tctgctcctg ctgccgctgc cctccggcgc gtggtacaag    180
cacgtggcga gtccccgcta ccacacggtg gccgcgccg ctggcctgct catgggctg     240 cgtcgctcac cctatctgtg gcgccgcgcg ctgcgcgcgg ccgccgggcc cctggccagg    300
gacaccctct ccccgaacc cgcagcccgc gaggctcctc tcctgctgcc ctcgtgggtt     360
caggagctgt gggag                                                      375
```

<210> SEQ ID NO 15
<211> LENGTH: 125
<212> TYPE: PRT
<213> ORGANISM: Human

<400> SEQUENCE: 15

```
Asn Ser Thr Ala Arg Pro Asn Pro Ala Glu Pro Val Arg Gly Pro Pro
 1               5                  10                  15

Arg Arg Ala Ala Val Asp Ala Ser Ala Leu Ala Trp Arg Pro Gly Glu
            20                  25                  30

Arg Gly Ala Pro Ala Ser Arg Pro Arg Leu Ala Leu Leu Leu Leu Leu
        35                  40                  45

Leu Leu Leu Pro Leu Pro Ser Gly Ala Trp Tyr Lys His Val Ala Ser
    50                  55                  60

Pro Arg Tyr His Thr Val Gly Arg Ala Ala Gly Leu Leu Met Gly Leu
65                  70                  75                  80

Arg Arg Ser Pro Tyr Leu Trp Arg Arg Ala Leu Arg Ala Ala Ala Gly
                85                  90                  95

Pro Leu Ala Arg Asp Thr Leu Ser Pro Glu Pro Ala Ala Arg Glu Ala
            100                 105                 110

Pro Leu Leu Leu Pro Ser Trp Val Gln Glu Leu Trp Glu
        115                 120                 125
```

<210> SEQ ID NO 16
<211> LENGTH: 23
<212> TYPE: PRT
<213> ORGANISM: Human

<400> SEQUENCE: 16

```
Trp Tyr Lys His Val Ala Ser Pro Arg Tyr His Thr Val Gly Arg Ala
 1               5                  10                  15

Ala Gly Leu Leu Met Gly Leu
            20
```

<210> SEQ ID NO 17
<211> LENGTH: 30
<212> TYPE: PRT
<213> ORGANISM: Human

<400> SEQUENCE: 17

```
Trp Tyr Lys His Val Ala Ser Pro Arg Tyr His Thr Val Gly Arg Ala
 1               5                  10                  15

Ala Gly Leu Leu Met Gly Leu Arg Arg Ser Pro Tyr Leu Trp
```

-continued

```
                    20                  25                  30

<210> SEQ ID NO 18
<211> LENGTH: 69
<212> TYPE: DNA
<213> ORGANISM: Human

<400> SEQUENCE: 18
tggtacaagc acgtggcgag tccccgctac cacacggtgg ccgcgccgc tggcctgctc      60 atggggctg                                                             69

<210> SEQ ID NO 19
<211> LENGTH: 90
<212> TYPE: DNA
<213> ORGANISM: Human

<400> SEQUENCE: 19
tggtacaagc acgtggcgag tccccgctac cacacggtgg ccgcgccgc tggcctgctc      60 atggggctgc gtcgctcacc ctatctgtgg                                      90

<210> SEQ ID NO 20
<211> LENGTH: 29
<212> TYPE: PRT
<213> ORGANISM: Human

<400> SEQUENCE: 20

Trp Tyr Lys His Val Ala Ser Pro Arg Tyr His Thr Val Gly Arg Ala
1               5                  10                  15

Ala Gly Leu Leu Met Gly Leu Arg Arg Ser Pro Tyr Leu
            20                  25

<210> SEQ ID NO 21
<211> LENGTH: 28
<212> TYPE: PRT
<213> ORGANISM: Human

<400> SEQUENCE: 21

Trp Tyr Lys His Val Ala Ser Pro Arg Tyr His Thr Val Gly Arg Ala
1               5                  10                  15

Ala Gly Leu Leu Met Gly Leu Arg Arg Ser Pro Tyr
            20                  25

<210> SEQ ID NO 22
<211> LENGTH: 27
<212> TYPE: PRT
<213> ORGANISM: Human

<400> SEQUENCE: 22

Trp Tyr Lys His Val Ala Ser Pro Arg Tyr His Thr Val Gly Arg Ala
1               5                  10                  15

Ala Gly Leu Leu Met Gly Leu Arg Arg Ser Pro
            20                  25

<210> SEQ ID NO 23
<211> LENGTH: 26
<212> TYPE: PRT
<213> ORGANISM: Human

<400> SEQUENCE: 23

Trp Tyr Lys His Val Ala Ser Pro Arg Tyr His Thr Val Gly Arg Ala
1               5                  10                  15
```

Ala Gly Leu Leu Met Gly Leu Arg Arg Ser
            20                  25

<210> SEQ ID NO 24
<211> LENGTH: 25
<212> TYPE: PRT
<213> ORGANISM: Human

<400> SEQUENCE: 24

Trp Tyr Lys His Val Ala Ser Pro Arg Tyr His Thr Val Gly Arg Ala
1               5                   10                  15

Ala Gly Leu Leu Met Gly Leu Arg Arg
            20                  25

<210> SEQ ID NO 25
<211> LENGTH: 24
<212> TYPE: PRT
<213> ORGANISM: Human

<400> SEQUENCE: 25

Trp Tyr Lys His Val Ala Ser Pro Arg Tyr His Thr Val Gly Arg Ala
1               5                   10                  15

Ala Gly Leu Leu Met Gly Leu Arg
            20

<210> SEQ ID NO 26
<211> LENGTH: 87
<212> TYPE: DNA
<213> ORGANISM: Human

<400> SEQUENCE: 26
tggtacaagc acgtggcgag tccccgctac cacacggtgg gccgcgccgc tggcctgctc      60
atggggctgc gtcgctcacc ctatctg                                         87

<210> SEQ ID NO 27
<211> LENGTH: 84
<212> TYPE: DNA
<213> ORGANISM: Human

<400> SEQUENCE: 27
tggtacaagc acgtggcgag tccccgctac cacacggtgg gccgcgccgc tggcctgctc      60
atggggctgc gtcgctcacc ctat                                            84

<210> SEQ ID NO 28
<211> LENGTH: 81
<212> TYPE: DNA
<213> ORGANISM: Human

<400> SEQUENCE: 28
tggtacaagc acgtggcgag tccccgctac cacacggtgg gccgcgccgc tggcctgctc      60
atggggctgc gtcgctcacc c                                               81

<210> SEQ ID NO 29
<211> LENGTH: 78
<212> TYPE: DNA
<213> ORGANISM: Human

<400> SEQUENCE: 29
tggtacaagc acgtggcgag tccccgctac cacacggtgg gccgcgccgc tggcctgctc      60
atggggctgc gtcgctca                                                   78

<210> SEQ ID NO 30
<211> LENGTH: 75
<212> TYPE: DNA
<213> ORGANISM: Human

<400> SEQUENCE: 30

```
tggtacaagc acgtggcgag tccccgctac cacacggtgg gccgcgccgc tggcctgctc    60
atggggctgc gtcgc                                                     75
```

<210> SEQ ID NO 31
<211> LENGTH: 72
<212> TYPE: DNA
<213> ORGANISM: Human

<400> SEQUENCE: 31

```
tggtacaagc acgtggcgag tccccgctac cacacggtgg gccgcgccgc tggcctgctc    60
atggggctgc gt                                                        72
```

<210> SEQ ID NO 32
<211> LENGTH: 999
<212> TYPE: DNA
<213> ORGANISM: Human

<400> SEQUENCE: 32

```
atgcaggccg ctgggcaccc agagcccctt gacagcaggg gctccttctc cctccccacg    60
atgggtgcca acgtctctca ggacaatggc actggccaca atgccacctt ctccgagcca   120
ctgccgttcc tctatgtgct cctgcccgcc gtgtactccg ggatctgtgc tgtggggctg   180
actggcaaca cggccgtcat ccttgtaatc ctaagggcgc ccaagatgaa gacggtgacc   240
aacgtgttca tcctgaacct ggccgtcgcc gacgggctct tcacgctggt actgccgtc    300 aacatcgcgg agcacctgct gcagtactgg cccttcgggg agctgctctg caagctggtg   360
ctggccgtcg accactacaa catcttctcc agcatctact cctagccgt gatgagcgtg    420 gaccgatacc tggtggtgct ggccaccgtg aggtcccgcc acatgccctg gcgcacctac   480
cggggggcga aggtcgccag cctgtgtgtc tggctgggcg tcacggtcct ggttctgccc   540
ttcttctctt tcgctggcgt ctacagcaac gagctgcagg tcccaagctg tgggctgagc   600
ttcccgtggc ccgagcgggt ctggttcaag gccagccgtg tctacacttt ggtcctgggc   660
ttcgtgctgc ccgtgtgcac catctgtgtg ctctacacag acctcctgcg caggctgcgg   720
gccgtgcggc tccgctctgg agccaaggct ctaggcaagg ccaggcggaa ggtgaccgtc   780
ctggtcctcg tcgtgctggc cgtgtgcctc ctctgctgga cgcccttcca cctggcctct   840
gtcgtggccc tgaccacgga cctgccccag accccactgg tcatcagtat gtcctacgtc   900
atcaccagcc tcacgtacgc caactcgtgc ctgaaccccct tcctctacgc ctttctagat   960
gacaacttcc ggaagaactt ccgcagcata ttgcggtgc                          999
```

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33

```
tctcccacag ctcctgaacc cacg                                           24
```

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
acagataggg tgagcgacgc agcc                                          24

<210> SEQ ID NO 35
<211> LENGTH: 1102
<212> TYPE: DNA
<213> ORGANISM: Human

<400> SEQUENCE: 35
gccatttaag tggagtcttg aaggatgagt aggtgttagg cacagacgca cagaggcagg    60
caaagccaca ggctgttggt ttaggcaaaa attgagactg ctggataaa gtggtcttgg    120 gggaccatca ccagagagga ggcgctggag gtctgcaagg ccttgtcctg cccctccagg   180
ggtagaggtt ccaggagggg ctgacttttt ctcctggaag cctcacagaa ctgcagaccc   240
cacggatggc ttggtgttgc aacatgagg cttctaaggc ttctgcgggg agatgggttg    300
gtggggagaa gctgggggtg gcagtggaca ggacagggtg tggggacagc tttgggagct   360
atgctaggca aggacaaggg acaactcttg gggggactca cccagagggg tcttgaatgg   420
tgctgaaggc ccccgacagc cctcctgcaa tagccactgt agctctgcct gcacctgggc   480
cttcgctctg ctgtcgtccc accggcagga gtctggctaa aggggcatcc ctcagcccta   540
ctccctcatc agtgttccca gtacccactc cctggcactt ccactcctag agggaggagg   600
ctgagcaggc agagaatggg acgtgtcccc tcagaggagc ctcgagccca gttccagcca   660
gcggcccact cagtgaggtg ctcaagtacc cacgtccccc gccagctgcc agggttccct   720
ctcctccctc cgtccctccc cccatctggg gagcccagcg gtactgaggg ggcggaacga   780
ggcggggcca ccgagcggtt atagctgggc ctgcaggga cccacggctc gcctccagcc    840
tcctgcgctc cggtacctgg gcgtcccaac tccactgcgc gcccaaaccc agccgagccg   900
gttcgtggcc cgccccgccg ggcggccgtc gacgcgagcg ccctggcgtg gcgcccaggg   960
gagcgggggg ctcccgcgag ccggccgcgg ctggcactgc tgctgcttct gctcctgctg  1020
ccgctgccct ccggcgcgtg gtacaagcac gtggcgagtc cccgctacca cacggtgggc  1080
cgcgccgctg gcctgctcat gg                                          1102

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
aactccactg cgcgcccaaa ccca                                          24

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37

```
ctggcactgc tgctgcttct gctc                                      24

<210> SEQ ID NO 38
<211> LENGTH: 609
<212> TYPE: DNA
<213> ORGANISM: Human

<400> SEQUENCE: 38
ctgctgccgc tgccctccgg cgcgtggtac aagcacgtgg cgagtccccg ctaccacacg    60
gtgggccgcg ccgctggcct gctcatgggg ctgcgtcgct caccctatct gtggcgccgc   120
gcgctgcgcg cggccgccgg gccccctggcc agggacaccc tctcccccga acccgcagcc   180
cgcgaggctc ctctcctgct gccctcgtgg gttcaggagc tgtgggagac gcgacgcagg   240
agctcccagg cagggatccc cgtccgtgcg ccccggagcc cgcgcgcccc agagcctgcg   300
ctggaaccgg agtccctgga cttcagcgga gctggccaga gacttcggag agacgtctcc   360
cgcccagcgg tggaccccgc agcaaaccgc cttggcctgc cctgcctggc ccccggaccg   420
ttctgacagc gtccccgcc cgccgtggc gcctccgcgc ctgacccagg aggagtggcc   480
gcgcgcttcc aggagccgct catagacccc gcctgccgtc cggtcaataa aatccgcctg   540
actcctgcgc ccccgcatgc gtaaaaaaaa aaaaaaaaa aaaaaaaaa agcggccgct   600 gaattctag                                                      609

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
agcggtactg aggggggcgga acga                                     24

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
gggtctatga gcggctcctg gaag                                      24

<210> SEQ ID NO 41
<211> LENGTH: 719
<212> TYPE: DNA
<213> ORGANISM: Human

<400> SEQUENCE: 41
ggcggggcca ccgagcggtt atagctgggc ctgcagggga cccacggctc gcctccagcc    60
tcctgcgctc cggtacctgg gcgtcccaac tccactgcgc gcccaaaccc agccgagccg   120
gttcgtggcc cgccccgccg gcggccgtc gacgcgagcg ccctggcgtg gcgcccaggg   180
gagcgggggg ctcccgcgag ccggccgcgg ctggcactgc tgctgcttct gctcctgctg   240
ccgctgccct ccggcgcgtg gtacaagcac gtggcgagtc cccgctacca cacggtgggc   300
cgcgccgctg gcctgctcat ggggctgcgt cgctcaccct atctgtggcg ccgcgcgctg   360
cgcgcggccg ccgggccccct ggccagggac accctctccc ccgaaccgc agcccgcgag   420 gctcctctcc tgctgccctc gtgggttcag gagctgtggg agacgcgacg caggagctcc   480
```

```
caggcaggga tccccgtccg tgcgccccgg agcccgcgcg ccccagagcc tgcgctggaa      540
ccggagtccc tggacttcag cggagctggc cagagacttc ggagagacgt ctcccgccca      600
gcggtggacc ccgcagcaaa ccgccttggc ctgccctgcc tggccccgg accgttctga      660 cagcgtcccc cgcccgcccg tggcgcctcc gcgcctgacc caggaggagt ggccgcgcg      719
```

```
<210> SEQ ID NO 42
<211> LENGTH: 165
<212> TYPE: PRT
<213> ORGANISM: Human

<400> SEQUENCE: 42
```

Leu Ala Trp Arg Pro Gly Glu Arg Gly Ala Pro Ala Ser Arg Pro Arg
1               5                   10                  15

Leu Ala Leu Leu Leu Leu Leu Leu Leu Pro Leu Pro Ser Gly Ala
            20                  25                  30

Trp Tyr Lys His Val Ala Ser Pro Arg Tyr His Thr Val Gly Arg Ala
        35                  40                  45

Ala Gly Leu Leu Met Gly Leu Arg Arg Ser Pro Tyr Leu Trp Arg Arg
    50                  55                  60

Ala Leu Arg Ala Ala Ala Gly Pro Leu Ala Arg Asp Thr Leu Ser Pro
65                  70                  75                  80

Glu Pro Ala Ala Arg Glu Ala Pro Leu Leu Leu Pro Ser Trp Val Gln
                85                  90                  95

Glu Leu Trp Glu Thr Arg Arg Arg Ser Ser Gln Ala Gly Ile Pro Val
            100                 105                 110

Arg Ala Pro Arg Ser Pro Arg Ala Pro Glu Pro Ala Leu Glu Pro Glu
        115                 120                 125

Ser Leu Asp Phe Ser Gly Ala Gly Gln Arg Leu Arg Arg Asp Val Ser
    130                 135                 140

Arg Pro Ala Val Asp Pro Ala Ala Asn Arg Leu Gly Leu Pro Cys Leu
145                 150                 155                 160

Ala Pro Gly Pro Phe
                165

```
<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
acagataggg tgagcgacgc agcc                                              24

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
tgagcgacgc agccccatga gcag                                              24

<210> SEQ ID NO 45
<211> LENGTH: 235
<212> TYPE: DNA
<213> ORGANISM: Porcine
```

<400> SEQUENCE: 45

```
cgacacccct gcgcccagac cctccggagc cagttcctgg tccgccccgc cgggagccgt      60
cagcatgaac ccccgggcac gcggcatggg agcgcgggc ccgggaccgg gggccactgc     120
gaggcgccgg ctgctggcat tgctgttact gctgctgctg ctgccgctgc ccgcccgtgc    180
ctggtacaag cacacggcga gtccccgcta ccacacggtg gccgcgccg cgggc          235
```

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46

```
cagcggcagc agcagcagca gtaa                                            24
```

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47

```
cagcagtaac agcaatgcca gcag                                            24
```

<210> SEQ ID NO 48
<211> LENGTH: 156
<212> TYPE: DNA
<213> ORGANISM: Porcine

<400> SEQUENCE: 48

```
ctgtagcctc ccgcgctgcg gcttcccgac accctgcgc ccagaccctc cggagccagt      60
tcctggtccg ccccgccggg agccgtcagc atgaacccc gggcacgcgg catgggagcg    120
cggggcccgg gaccgggggc cactgcgagg cgccgg                              156
```

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49

```
cggctgctgg cattgctgtt actg                                            24
```

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50

```
cgcccgtgcc tggtacaagc aca                                             23
```

<210> SEQ ID NO 51
<211> LENGTH: 588
<212> TYPE: DNA
<213> ORGANISM: Porcine

-continued

```
<400> SEQUENCE: 51
cggcgagtcc ccgctaccac acggtgggcc gcgccgcggg cctgctcatg gggctgcgcc      60
gctcgcccta catgtggcgc cgcgcgctgc gcccggcggc cgggcccctg gcctgggaca     120
ctttcggcca ggacgtgccc cctcggggac cctccgccag gaacgccctc tctccggggc     180
ccgcccctcg cgacgctccg ctgcttcccc ccggggttca gacactgtgg caggtgcgac     240
gcggaagctt ccgctccggg atcccggtca gtgcgccccg cagcccgcgc gcccgggggt     300
ccgagccgca accggaattg ggcgcctctt cctggacctc ggcggagtag accagagcct     360
tcggagagtc ttcagctcag cggtggtctg cgcaggaac cgccttcgcc agcccccgcc      420
tcgccccagc gtcagagccg acctgatcgc ggccccggcg gcgcggcccc gcgcctggcc     480
cccgcggagt ctcttcgcgc ccccaggccg gccgtctggt caataaaacc cgcctagttc     540
ctgcgaaaaa aaaaaaaaaa aaaaaaaaaa aaaaaaaaaa aaaaaaaa                  588

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
ttcccgacac ccctgcgccc agac                                             24

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
gggctggcga aggcggttcc ctgc                                             24

<210> SEQ ID NO 54
<211> LENGTH: 565
<212> TYPE: DNA
<213> ORGANISM: Porcine

<400> SEQUENCE: 54
cctccggagc cagttcctgg tccgccccgc cgggagccgt cagcatgaac ccccgggcac      60
gcggcatggg agcgcggggc ccgggaccgg gggccactgc gaggcgccgg ctgctggcat     120
tgctgttact gctgctgctg ctgccgctgc ccgcccgtgc ctggtacaag cacacgcga     180 gtccccgcta ccacacggtg gccgcgcgcg cgggcctgct catggggctg cgccgctcgc     240
cctacatgtg gcgccgcgcg ctgcgcccgg cggcgggcc cctggcctgg gacactttcg     300
gccaggacgt gccccctcgg ggaccctccg ccaggaacgc cctctctccg ggcccgccc     360 ctcgcgacgc tccgctgctt ccccccgggg ttcagacact gtggcaggtg cgacgcggaa     420
gcttccgctc cgggatcccg gtcagtgcgc cccgcagccc gcgcgccgg ggtccgagc      480 cgcaaccgga attgggcgcc tcttcctgga cctcggcgga gtagaccaga gccttcggag     540
agtcttcagc tcagcggtgg tctgc                                           565

<210> SEQ ID NO 55
<211> LENGTH: 159
<212> TYPE: PRT
<213> ORGANISM: Porcine
```

<400> SEQUENCE: 55

Met Asn Pro Arg Ala Arg Gly Met Gly Ala Arg Gly Pro Gly Pro Gly
1               5                   10                  15

Ala Thr Ala Arg Arg Leu Leu Ala Leu Leu Leu Leu Leu Leu Leu Leu
                20                  25                  30

Leu Pro Leu Pro Ala Arg Ala Trp Tyr Lys His Thr Ala Ser Pro Arg
            35                  40                  45

Tyr His Thr Val Gly Arg Ala Ala Gly Leu Leu Met Gly Leu Arg Arg
        50                  55                  60

Ser Pro Tyr Met Trp Arg Ala Leu Arg Pro Ala Ala Gly Pro Leu
65                  70                  75                  80

Ala Trp Asp Thr Phe Gly Gln Asp Val Pro Arg Gly Pro Ser Ala
                85                  90                  95

Arg Asn Ala Leu Ser Pro Gly Pro Ala Pro Arg Asp Ala Pro Leu Leu
                100                 105                 110

Pro Pro Gly Val Gln Thr Leu Trp Gln Val Arg Arg Gly Ser Phe Arg
            115                 120                 125

Ser Gly Ile Pro Val Ser Ala Pro Arg Ser Pro Arg Ala Arg Gly Ser
        130                 135                 140

Glu Pro Gln Pro Glu Leu Gly Ala Ser Ser Trp Thr Ser Ala Glu
145                 150                 155

<210> SEQ ID NO 56
<211> LENGTH: 23
<212> TYPE: PRT
<213> ORGANISM: Porcine

<400> SEQUENCE: 56

Trp Tyr Lys His Thr Ala Ser Pro Arg Tyr His Thr Val Gly Arg Ala
1               5                   10                  15

Ala Gly Leu Leu Met Gly Leu
            20

<210> SEQ ID NO 57
<211> LENGTH: 30
<212> TYPE: PRT
<213> ORGANISM: Porcine

<400> SEQUENCE: 57

Trp Tyr Lys His Thr Ala Ser Pro Arg Tyr His Thr Val Gly Arg Ala
1               5                   10                  15

Ala Gly Leu Leu Met Gly Leu Arg Arg Ser Pro Tyr Met Trp
            20                  25                  30

<210> SEQ ID NO 58
<211> LENGTH: 69
<212> TYPE: DNA
<213> ORGANISM: Porcine

<400> SEQUENCE: 58
tggtacaagc acacggcgag tccccgctac cacacggtgg gccgcgccgc gggcctgctc        60
atggggctg                                                               69

<210> SEQ ID NO 59
<211> LENGTH: 90
<212> TYPE: DNA
<213> ORGANISM: Porcine

<400> SEQUENCE: 59
tggtacaagc acacggcgag tccccgctac cacacggtgg gccgcgccgc gggcctgctc    60
atggggctgc gccgctcgcc ctacatgtgg                                    90

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
cgttctcggg gacataaacc ctg                                           23

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
atgagcagcc cggaggcacg acc                                           23

<210> SEQ ID NO 62
<211> LENGTH: 188
<212> TYPE: DNA
<213> ORGANISM: Rat

<400> SEQUENCE: 62
ttcttgtcct aacccgccaa ggggccatgg acttgagcgc gctggcgtcg agcagagaag    60
tacggggccc tgggcccggg gctccggtga accggcccct gctaccgcta ctgctgcttc   120
tgctcttgct acctctgccc gccagcgcct ggtacaagca cgtggcgagc cctcgctatc   180
acacagtg                                                           188

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
atgagcagcc cggaggcacg acc                                           23

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
actgtgtgat agcgagggct cgc                                           23

<210> SEQ ID NO 65
<211> LENGTH: 615
<212> TYPE: DNA
<213> ORGANISM: Rat

<400> SEQUENCE: 65
ctcagagctg tactaggcag gaagagggac ggccctcagg gaagggtggc cctatgctta    60

-continued

```
aaactttcct gtctcctctc cataagtgct ccacttgtag caactcctac caagggggca    120
tccttttgcc cctggcagcc catccttgta ttctgagacc atgcatggta ccagaactcc    180
ctccctgaca gttcccttcc tgggggcgag gaaagggtaa gcaaggagat cccccactaa    240
agcttcaagc gcagtccagc ttgcgatcta ctcattggga ggcttctagc tacccgggtt    300
ccctcttctc cctccctctc catcctcctc tcccttgggc atgtgccgcg ggggcgagcc    360 ggggcgggc cattgagaag ctgtagtcgc accaactgac tagtctcttc catcctccgg    420
agctccgact tctcggggga cataaaccct gttcttgtcc taacccgcca agggggccatg    480 gacttgagcg cgctggcgtc gagcagagaa gtacggggcc ctgggcccgg ggctccggtg    540
aaccggcccc tgctaccgct actgctgctt ctgctcttgc tacctctgcc cgccagcgcc    600
tggtacaagc acgtg                                                      615
```

<210> SEQ ID NO 66
<211> LENGTH: 23
<212> TYPE: DNA
<213> ORGANISM: Artificial Sequence
<220> FEATURE:
<223> OTHER INFORMATION: Primer

<400> SEQUENCE: 66

```
cgttctcggg gacataaacc ctg                                             23
```

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67

```
cgagccctcg ctatcacaca gtgg                                            24
```

<210> SEQ ID NO 68
<211> LENGTH: 497
<212> TYPE: DNA
<213> ORGANISM: Rat

<400> SEQUENCE: 68

```
gtcgtgcctc cgggctgctc atggggctgc gccgctcgcc ctacctgtgg cgccgtgcct     60
tgggtggggc cgctggaccg ctcgtggggc tcccggaca gatggcccgc agcgctctcc    120
tgcttccttc ccccgggcag gagctgtggg aggtacgaag caggagttca ccggcaggac    180
ttcccgtgca tgcaacccgg agtctgcggg acctggaggg agccggccaa cctgagcagt    240
cgctaagctt tcagtcctgg acttcagcag agcccgctgc tagagccttc ggtgagacgc    300
ttcgtgccca gccatggttc ctgcagcaaa tcatcttttgc cgatcctgtc aggctcgacg    360
accgtctcaa gaaccgatgg cgcccccgtg cttgacctaa gcaggagcac agcttgtagc    420
tccagtcagg tctcgttgtc tggtcaataa aatcactctg attcccaaaa aaaaaaaaa    480 aaaaaaaaaa aaaaaaa                                                    497
```

<210> SEQ ID NO 69
<211> LENGTH: 21
<212> TYPE: DNA
<213> ORGANISM: Artificial Sequence
<220> FEATURE:
<223> OTHER INFORMATION: Primer

```
<400> SEQUENCE: 69
ggggcggggc cattgagaag c                                               21

<210> SEQ ID NO 70
<211> LENGTH: 21
<212> TYPE: DNA
<213> ORGANISM: Artificial Sequence
<220> FEATURE:
<223> OTHER INFORMATION: Primer

<400> SEQUENCE: 70
tgaccagaca acgagacctg a                                               21

<210> SEQ ID NO 71
<211> LENGTH: 684
<212> TYPE: DNA
<213> ORGANISM: Rat

<400> SEQUENCE: 71
tgtagtcgca ccaactgact agtctcttcc atcctccgga gctccgacgt tctcggggac     60
ataaaccctg ttcttgtcct aacccgccaa ggggccatgg acttgagcgc gctggcgtcg    120
agcagagaag tacggggccc tgggcccggg gctccggtga accggcccct gctaccgcta    180
ctgctgcttc tgctcttgct acctctgccc gccagcgcct ggtacaagca cgtggcgagc    240
cctcgctatc acacagtggg tcgtgcctcc gggctgctca tggggctgcg ccgctcgccc    300
tacctgtggc gccgtgcctt gggtggggcc gctggaccgc tcgtggggct cccgggacag    360
atggcccgca gcgctctcct gcttccttcc cccgggcagg agctgtggga ggtacgaagc    420
aggagttcac cggcaggact tcccgtgcat gcaacccgga gtctgcggga cctggaggga    480
gccggccaac ctgagcagtc gctaagcttt cagtcctgga cttcagcaga gcccgctgct    540
agagccttcg gtgagacgct tcgtgcccag ccatggttcc tgcagcaaat catctttgcc    600
gatcctgtca ggctcgacga ccgtctcaag aaccgatggc gccccgtgc ttgacctaag     660 caggagcaca gcttgtagct ccag                                          684

<210> SEQ ID NO 72
<211> LENGTH: 185
<212> TYPE: PRT
<213> ORGANISM: Rat

<400> SEQUENCE: 72

Met Asp Leu Ser Ala Leu Ala Ser Ser Arg Glu Val Arg Gly Pro Gly
1               5                  10                  15

Pro Gly Ala Pro Val Asn Arg Pro Leu Leu Pro Leu Leu Leu Leu Leu
            20                  25                  30

Leu Leu Leu Pro Leu Pro Ala Ser Ala Trp Tyr Lys His Val Ala Ser
        35                  40                  45

Pro Arg Tyr His Thr Val Gly Arg Ala Ser Gly Leu Leu Met Gly Leu
    50                  55                  60

Arg Arg Ser Pro Tyr Leu Trp Arg Arg Ala Leu Gly Gly Ala Ala Gly
65                  70                  75                  80

Pro Leu Val Gly Leu Pro Gly Gln Met Ala Arg Ser Ala Leu Leu Leu
                85                  90                  95

Pro Ser Pro Gly Gln Glu Leu Trp Glu Val Arg Ser Arg Ser Ser Pro
            100                 105                 110

Ala Gly Leu Pro Val His Ala Thr Arg Ser Leu Arg Asp Leu Glu Gly
        115                 120                 125
```

```
Ala Gly Gln Pro Glu Gln Ser Leu Ser Phe Gln Ser Trp Thr Ser Ala
    130                 135                 140

Glu Pro Ala Ala Arg Ala Phe Gly Glu Thr Leu Arg Ala Gln Pro Trp
145                 150                 155                 160

Phe Leu Gln Gln Ile Ile Phe Ala Asp Pro Val Arg Leu Asp Asp Arg
                165                 170                 175

Leu Lys Asn Arg Trp Arg Pro Arg Ala
            180                 185

<210> SEQ ID NO 73
<211> LENGTH: 23
<212> TYPE: PRT
<213> ORGANISM: Rat

<400> SEQUENCE: 73

Trp Tyr Lys His Val Ala Ser Pro Arg Tyr His Thr Val Gly Arg Ala
1               5                   10                  15

Ser Gly Leu Leu Met Gly Leu
            20

<210> SEQ ID NO 74
<211> LENGTH: 30
<212> TYPE: PRT
<213> ORGANISM: Rat

<400> SEQUENCE: 74

Trp Tyr Lys His Val Ala Ser Pro Arg Tyr His Thr Val Gly Arg Ala
1               5                   10                  15

Ser Gly Leu Leu Met Gly Leu Arg Arg Ser Pro Tyr Leu Trp
            20                  25                  30

<210> SEQ ID NO 75
<211> LENGTH: 69
<212> TYPE: DNA
<213> ORGANISM: Rat

<400> SEQUENCE: 75
tggtacaagc acgtggcgag ccctcgctat cacacagtgg gtcgtgcctc cgggctgctc    60
atggggctg                                                            69

<210> SEQ ID NO 76
<211> LENGTH: 90
<212> TYPE: DNA
<213> ORGANISM: Rat

<400> SEQUENCE: 76
tggtacaagc acgtggcgag ccctcgctat cacacagtgg gtcgtgcctc cgggctgctc    60
atggggctgc gccgctcgcc ctacctgtgg                                     90

<210> SEQ ID NO 77
<211> LENGTH: 529
<212> TYPE: DNA
<213> ORGANISM: Mouse

<400> SEQUENCE: 77
acgtgctcgt tctcggagac ataaacccag ttcttgtcct aaccctccaa ggggcaattg    60
acgtgagcgc gctggcgtct aacagagaag tacggggccc tgggcccggg actcccagga   120
accggcccct gctgccctg ctgctgcttc tgctcttgct accgctgccc gccagcgcct   180
```

```
ggtataagca cgtggcgagt ccccgctatc acacagtggg tcgtgcctcc gggctgctca    240
tggggctgcg ccgctcgccc taccagtggc gccgtgccct gggcggggct gctggacccc    300
tctcccggct cccaggaccg gtcgcccgcg gcgctctcct gcttccttcc tcagggcagg    360
agctgtggga ggtacgaagc aggagctcac ctgcagggct ccccgtccat gcaccctgga    420
gtccgcggga cctggaggga gtccgccaac cggagcagtc gctaagcctt cactcctgga    480
tgtcagagga gcccgctgat aggtaagtag gaaagagagg aggcgggcg                529
```

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78

```
acccagttct tgtcctaacc ctcc                                            24
```

<210> SEQ ID NO 79
<211> LENGTH: 24
<212> TYPE: DNA
<213> ORGANISM: Artificial Sequence
<220> FEATURE:
<223> OTHER INFORMATION: Primer

<400> SEQUENCE: 79

```
cctgcttcgt acctcccaca gctc                                            24
```

<210> SEQ ID NO 80
<211> LENGTH: 311
<212> TYPE: DNA
<213> ORGANISM: Mouse

<400> SEQUENCE: 80

```
aagggggcaat tgacgtgagc gcgctggcgt ctaacagaga agtacggggc cctgggcccg    60
ggactcccag gaaccggccc ctgctgcccc tgctgctgct tctgctcttg ctaccgctgc    120
ccgccagcgc ctggtataag cacgtggcga gtccccgcta tcacacagtg ggtcgtgcct    180
ccgggctgct catggggctg cgccgctcgc cctaccagtg gcgccgtgcc ctgggcgggg    240
ctgctggacc cctctcccgg ctcccaggac cggtcgcccg cggcgctctc ctgcttcctt    300
cctcagggca g                                                          311
```

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81

```
catgagcagc ccggaggcac gacc                                            24
```

<210> SEQ ID NO 82
<211> LENGTH: 24
<212> TYPE: DNA
<213> ORGANISM: Artificial Sequence
<220> FEATURE:
<223> OTHER INFORMATION: Primer

<400> SEQUENCE: 82

```
gtgatagcgg ggactcgcca cgtg                                            24
```

<210> SEQ ID NO 83
<211> LENGTH: 237
<212> TYPE: DNA
<213> ORGANISM: Mouse

<400> SEQUENCE: 83

```
aaaggctgta gtcgcaccaa ctgactggtc tccatcctct ggagctccga cgtgctcgtt      60
ctcggagaca taaacccagt tcttgtccta accctccaag gggcaattga cgtgagcgcg     120
ctggcgtcta acagagaagt acggggccct gggcccggga ctcccaggaa ccggcccctg     180
ctgcccctgc tgctgcttct gctcttgcta ccgctgcccg ccagcgcctg gtataag        237
```

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84

```
acccagttct tgtcctaacc ctcc                                             24
```

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85

```
gggcaattga cgtgagcgcg ctgg                                             24
```

<210> SEQ ID NO 86
<211> LENGTH: 598
<212> TYPE: DNA
<213> ORGANISM: Mouse

<400> SEQUENCE: 86

```
cgtctaacag agaagtacgg ggccctgggc ccgggactcc caggaaccgg ccctgctgc       60
ccctgctgct gcttctgctc ttgctaccgc tgcccgccag cgcctggtat aagcacgtgg     120
cgagtccccg ctatcacaca gtgggtcgtg cctccgggct gctcatgggg ctgcgccgct     180
cgccctacca gtggcgccgt gccctgggcg gggctgctgg accctctcc cggctcccag      240
gaccggtcgc ccgcggcgct ctcctgcttc cttcctcagg gcaggagctg tgggaggtac     300
gaagcaggag ctcacctgca gggcttcccg tccatgcacc ctggagtccg cggacctgg      360
agggagtccg ccaaccggag cagtcgctaa gccttcactc ctggatctca gaggagcccg     420
ctgctagagc cttcggagag acgcttcgtg cccagccatg gttcctgcag caagtcatct     480
ttgccgatcc tgtcaggccc aagaaccgat ggcgccccca tgcttgacct aggcaggagc     540
acagcttgaa gctccagtca ggcctcgtgt ttctggtcaa taaaaccaac ctgattcc       598
```

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87

```
aaaggctgta gtcgcaccaa c                                                   21
```

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88

```
accagaaaca cgaggcctga c                                                   21
```

<210> SEQ ID NO 89
<211> LENGTH: 659
<212> TYPE: DNA
<213> ORGANISM: Mouse

<400> SEQUENCE: 89

```
tgactggtct ccatcctctg gagctccgac gtgctcgttc tcggagacat aaacccagtt         60
cttgtcctaa ccctccaagg ggcaattgac gtgagcgcgc tggcgtctaa cagagaagta        120
cggggccctg ggcccgggac tcccaggaac cggcccctgc tgcccctgct gctgcttctg        180
ctcttgctac cgctgcccgc cagcgcctgg tataagcacg tggcgagtcc ccgctatcac        240
acagtgggtc gtgcctccgg gctgctcatg gggctgcgcc gctcgcccta ccagtggcgc        300
cgtgccctgg gcgggctgc tggaccccctc tcccggctcc caggaccggt cgcccgcggc        360
gctctcctgc ttccttcctc agggcaggag ctgtgggagg tacgaagcag gagctcacct        420
gcagggcttc ccgtccatgc acctggagt ccgcgggacc tggagggagt ccgccaaccg         480
gagcagtcgc taagccttca ctcctggatc tcagaggagc ccgctgctag agccttcgga        540
gagacgcttc gtgcccagcc atggttcctg cagcaagtca tctttgccga tcctgtcagg        600
cccaagaacc gatggcgccc ccatgcttga cctaggcagg agcacagctt gaagctcca         659
```

<210> SEQ ID NO 90
<211> LENGTH: 176
<212> TYPE: PRT
<213> ORGANISM: Mouse

<400> SEQUENCE: 90

```
Leu Ala Ser Asn Arg Glu Val Arg Gly Pro Gly Pro Gly Thr Pro Arg
1               5                   10                  15

Asn Arg Pro Leu Leu Pro Leu Leu Leu Leu Leu Leu Leu Pro Leu
            20                  25                  30

Pro Ala Ser Ala Trp Tyr Lys His Val Ala Ser Pro Arg Tyr His Thr
        35                  40                  45

Val Gly Arg Ala Ser Gly Leu Leu Met Gly Leu Arg Arg Ser Pro Tyr
    50                  55                  60

Gln Trp Arg Arg Ala Leu Gly Gly Ala Ala Gly Pro Leu Ser Arg Leu
65                  70                  75                  80

Pro Gly Pro Val Ala Arg Gly Ala Leu Leu Pro Ser Ser Gly Gln
                85                  90                  95

Glu Leu Trp Glu Val Arg Ser Arg Ser Ser Pro Ala Gly Leu Pro Val
            100                 105                 110

His Ala Pro Trp Ser Pro Arg Asp Leu Glu Gly Val Arg Gln Pro Glu
        115                 120                 125

Gln Ser Leu Ser Leu His Ser Trp Ile Ser Glu Glu Pro Ala Ala Arg
    130                 135                 140
```

```
Ala Phe Gly Glu Thr Leu Arg Ala Gln Pro Trp Phe Leu Gln Gln Val
145                 150                 155                 160

Ile Phe Ala Asp Pro Val Arg Pro Lys Asn Arg Trp Arg Pro His Ala
                165                 170                 175

<210> SEQ ID NO 91
<211> LENGTH: 23
<212> TYPE: PRT
<213> ORGANISM: Mouse

<400> SEQUENCE: 91

Trp Tyr Lys His Val Ala Ser Pro Arg Tyr His Thr Val Gly Arg Ala
1               5                   10                  15

Ser Gly Leu Leu Met Gly Leu
            20

<210> SEQ ID NO 92
<211> LENGTH: 30
<212> TYPE: PRT
<213> ORGANISM: Mouse

<400> SEQUENCE: 92

Trp Tyr Lys His Val Ala Ser Pro Arg Tyr His Thr Val Gly Arg Ala
1               5                   10                  15

Ser Gly Leu Leu Met Gly Leu Arg Arg Ser Pro Tyr Gln Trp
            20                  25                  30

<210> SEQ ID NO 93
<211> LENGTH: 69
<212> TYPE: DNA
<213> ORGANISM: Mouse

<400> SEQUENCE: 93
tggtataagc acgtggcgag tccccgctat cacacagtgg gtcgtgcctc cgggctgctc      60
atggggctg                                                              69

<210> SEQ ID NO 94
<211> LENGTH: 90
<212> TYPE: DNA
<213> ORGANISM: Mouse

<400> SEQUENCE: 94
tggtataagc acgtggcgag tccccgctat cacacagtgg gtcgtgcctc cgggctgctc      60
atggggctgc gccgctcgcc ctaccagtgg                                       90

<210> SEQ ID NO 95
<211> LENGTH: 23
<212> TYPE: PRT
<213> ORGANISM: Artificial Sequence
<220> FEATURE:
<221> NAME/KEY: MOD_RES
<222> LOCATION: 21
<223> OTHER INFORMATION: Xaa on the 21st position means Met(O)

<400> SEQUENCE: 95

Trp Tyr Lys His Val Ala Ser Pro Arg Tyr His Thr Val Gly Arg Ala
1               5                   10                  15

Ala Gly Leu Leu Xaa Gly Leu
            20

<210> SEQ ID NO 96
<211> LENGTH: 22
```

-continued

<212> TYPE: PRT
<213> ORGANISM: Human

<400> SEQUENCE: 96

Trp Tyr Lys His Val Ala Ser Pro Arg Tyr His Thr Val Gly Arg Ala
1               5                   10                  15

Ala Gly Leu Leu Met Gly
            20

<210> SEQ ID NO 97
<211> LENGTH: 21
<212> TYPE: PRT
<213> ORGANISM: Human

<400> SEQUENCE: 97

Trp Tyr Lys His Val Ala Ser Pro Arg Tyr His Thr Val Gly Arg Ala
1               5                   10                  15

Ala Gly Leu Leu Met
            20

<210> SEQ ID NO 98
<211> LENGTH: 20
<212> TYPE: PRT
<213> ORGANISM: Human

<400> SEQUENCE: 98

Trp Tyr Lys His Val Ala Ser Pro Arg Tyr His Thr Val Gly Arg Ala
1               5                   10                  15

Ala Gly Leu Leu
            20

<210> SEQ ID NO 99
<211> LENGTH: 19
<212> TYPE: PRT
<213> ORGANISM: Human

<400> SEQUENCE: 99

Trp Tyr Lys His Val Ala Ser Pro Arg Tyr His Thr Val Gly Arg Ala
1               5                   10                  15

Ala Gly Leu

<210> SEQ ID NO 100
<211> LENGTH: 18
<212> TYPE: PRT
<213> ORGANISM: Human

<400> SEQUENCE: 100

Trp Tyr Lys His Val Ala Ser Pro Arg Tyr His Thr Val Gly Arg Ala
1               5                   10                  15

Ala Gly

<210> SEQ ID NO 101
<211> LENGTH: 17
<212> TYPE: PRT
<213> ORGANISM: Human

<400> SEQUENCE: 101

Trp Tyr Lys His Val Ala Ser Pro Arg Tyr His Thr Val Gly Arg Ala
1               5                   10                  15

Ala

```
<210> SEQ ID NO 102
<211> LENGTH: 16
<212> TYPE: PRT
<213> ORGANISM: Human

<400> SEQUENCE: 102

Trp Tyr Lys His Val Ala Ser Pro Arg Tyr His Thr Val Gly Arg Ala
1               5                   10                  15

<210> SEQ ID NO 103
<211> LENGTH: 23
<212> TYPE: PRT
<213> ORGANISM: Artificial Sequence
<220> FEATURE:
<221> NAME/KEY: MOD_RES
<222> LOCATION: 21
<223> OTHER INFORMATION: Xaa on the 21st position means Met(O)

<400> SEQUENCE: 103

Trp Tyr Lys His Thr Ala Ser Pro Arg Tyr His Thr Val Gly Arg Ala
1               5                   10                  15

Ala Gly Leu Leu Xaa Gly Leu
            20

<210> SEQ ID NO 104
<211> LENGTH: 23
<212> TYPE: PRT
<213> ORGANISM: Artificial Sequence
<220> FEATURE:
<221> NAME/KEY: MOD_RES
<222> LOCATION: 21
<223> OTHER INFORMATION: Xaa on the 21st position means Met(O)

<400> SEQUENCE: 104

Trp Tyr Lys His Val Ala Ser Pro Arg Tyr His Thr Val Gly Arg Ala
1               5                   10                  15

Ser Gly Leu Leu Xaa Gly Leu
            20

<210> SEQ ID NO 105
<211> LENGTH: 23
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa on the 1st position means Fmoc Trp

<400> SEQUENCE: 105

Xaa Tyr Lys His Val Ala Ser Pro Arg Tyr His Thr Val Gly Arg Ala
1               5                   10                  15

Ala Gly Leu Leu Met Gly Leu
            20

<210> SEQ ID NO 106
<211> LENGTH: 23
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa on the 1st position means Ac Trp

<400> SEQUENCE: 106

Xaa Tyr Lys His Val Ala Ser Pro Arg Tyr His Thr Val Gly Arg Ala
1               5                   10                  15
```

Ala Gly Leu Leu Met Gly Leu
            20

<210> SEQ ID NO 107
<211> LENGTH: 22
<212> TYPE: PRT
<213> ORGANISM: Human

<400> SEQUENCE: 107

Tyr Lys His Val Ala Ser Pro Arg Tyr His Thr Val Gly Arg Ala Ala
1               5                   10                  15

Gly Leu Leu Met Gly Leu
            20

<210> SEQ ID NO 108
<211> LENGTH: 20
<212> TYPE: PRT
<213> ORGANISM: Human

<400> SEQUENCE: 108

His Val Ala Ser Pro Arg Tyr His Thr Val Gly Arg Ala Ala Gly Leu
1               5                   10                  15

Leu Met Gly Leu
            20

<210> SEQ ID NO 109
<211> LENGTH: 15
<212> TYPE: PRT
<213> ORGANISM: Human

<400> SEQUENCE: 109

Arg Tyr His Thr Val Gly Arg Ala Ala Gly Leu Leu Met Gly Leu
1               5                   10                  15

<210> SEQ ID NO 110
<211> LENGTH: 9
<212> TYPE: PRT
<213> ORGANISM: Human

<400> SEQUENCE: 110

Arg Ala Ala Gly Leu Leu Met Gly Leu
1               5

<210> SEQ ID NO 111
<211> LENGTH: 22
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa on the 1st position means Ac Tyr

<400> SEQUENCE: 111

Xaa Lys His Val Ala Ser Pro Arg Tyr His Thr Val Gly Arg Ala Ala
1               5                   10                  15

Gly Leu Leu Met Gly Leu
            20

<210> SEQ ID NO 112
<211> LENGTH: 23
<212> TYPE: PRT
<213> ORGANISM: Artificial Sequence
<220> FEATURE:
<221> NAME/KEY: MOD_RES
<222> LOCATION: 1

<223> OTHER INFORMATION: Xaa on the 1st position means DTrp

<400> SEQUENCE: 112

Xaa Tyr Lys His Val Ala Ser Pro Arg Tyr His Thr Val Gly Arg Ala
 1               5                  10                  15

Ala Gly Leu Leu Met Gly Leu
            20

<210> SEQ ID NO 113
<211> LENGTH: 22
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa on the 1st position means 3-Indolepropanoyl
                        Tyr

<400> SEQUENCE: 113

Xaa Lys His Val Ala Ser Pro Arg Tyr His Thr Val Gly Arg Ala Ala
 1               5                  10                  15

Gly Leu Leu Met Gly Leu
            20

<210> SEQ ID NO 114
<211> LENGTH: 66
<212> TYPE: DNA
<213> ORGANISM: Human

<400> SEQUENCE: 114
tggtacaagc acgtggcgag tccccgctac cacacggtgg gccgcgccgc tggcctgctc    60
atgggg                                                               66

<210> SEQ ID NO 115
<211> LENGTH: 63
<212> TYPE: DNA
<213> ORGANISM: Human

<400> SEQUENCE: 115
tggtacaagc acgtggcgag tccccgctac cacacggtgg gccgcgccgc tggcctgctc    60
atg                                                                  63

<210> SEQ ID NO 116
<211> LENGTH: 60
<212> TYPE: DNA
<213> ORGANISM: Human

<400> SEQUENCE: 116
tggtacaagc acgtggcgag tccccgctac cacacggtgg gccgcgccgc tggcctgctc    60

<210> SEQ ID NO 117
<211> LENGTH: 57
<212> TYPE: DNA
<213> ORGANISM: Human

<400> SEQUENCE: 117
tggtacaagc acgtggcgag tccccgctac cacacggtgg gccgcgccgc tggcctg       57

<210> SEQ ID NO 118
<211> LENGTH: 54
<212> TYPE: DNA
<213> ORGANISM: Human

<400> SEQUENCE: 118
tggtacaagc acgtggcgag tccccgctac cacacggtgg gccgcgccgc tggc        54

<210> SEQ ID NO 119
<211> LENGTH: 51
<212> TYPE: DNA
<213> ORGANISM: Human

<400> SEQUENCE: 119
tggtacaagc acgtggcgag tccccgctac cacacggtgg gccgcgccgc t           51

<210> SEQ ID NO 120
<211> LENGTH: 48
<212> TYPE: DNA
<213> ORGANISM: Human

<400> SEQUENCE: 120
tggtacaagc acgtggcgag tccccgctac cacacggtgg gccgcgcc               48

<210> SEQ ID NO 121
<211> LENGTH: 66
<212> TYPE: DNA
<213> ORGANISM: Human

<400> SEQUENCE: 121
tacaagcacg tggcgagtcc ccgctaccac acggtgggcc gcgccgctgg cctgctcatg  60
gggctg                                                            66

<210> SEQ ID NO 122
<211> LENGTH: 60
<212> TYPE: DNA
<213> ORGANISM: Human

<400> SEQUENCE: 122
cacgtggcga gtccccgcta ccacacggtg ggccgcgccg ctggcctgct catggggctg  60

<210> SEQ ID NO 123
<211> LENGTH: 45
<212> TYPE: DNA
<213> ORGANISM: Human

<400> SEQUENCE: 123
cgctaccaca cggtgggccg cgccgctggc ctgctcatgg ggctg                  45

<210> SEQ ID NO 124
<211> LENGTH: 27
<212> TYPE: DNA
<213> ORGANISM: Human

<400> SEQUENCE: 124
cgcgccgctg gcctgctcat ggggctg                                      27

<210> SEQ ID NO 125
<211> LENGTH: 51
<212> TYPE: DNA
<213> ORGANISM: Porcine

<400> SEQUENCE: 125
tggtacaagc acacggcgag tccccgctac cacacggtgg gccgcgccgc g           51

<210> SEQ ID NO 126
<211> LENGTH: 32

```
<212> TYPE: DNA
<213> ORGANISM: Artificial Sequence
<220> FEATURE:
<223> OTHER INFORMATION: Primer

<400> SEQUENCE: 126
atcgatatgg acaacgcctc gttctcggag cc                                    32

<210> SEQ ID NO 127
<211> LENGTH: 32
<212> TYPE: DNA
<213> ORGANISM: Artificial Sequence
<220> FEATURE:
<223> OTHER INFORMATION: Primer

<400> SEQUENCE: 127
actagtgtca ggctgccgcg cggcaagtta tc                                    32

<210> SEQ ID NO 128
<211> LENGTH: 1000
<212> TYPE: DNA
<213> ORGANISM: Human

<400> SEQUENCE: 128
atcgatatgg acaacgcctc gttctcggag ccctggcccg ccaacgcatc gggcccggac       60
ccggcgctga gctgctccaa cgcgtcgact ctggcgccgc tgccggcgcc gctggcggtg      120
gctgtaccag ttgtctacgc ggtgatctgc gccgtgggtc tggcgggcaa ctccgccgtg      180
ctgtacgtgt tgctgcgggc gccccgcatg aagaccgtca ccaacctgtt catcctcaac      240
ctggccatcg ccgacgagct cttcacgctg gtgctgccca tcaacatcgc cgacttcctg      300
ctgcggcagt ggcccttcgg ggagctcatg tgcaagctca tcgtggctat cgaccagtac      360
aacaccttct ccagcctcta cttcctcacc gtcatgagcg ccgaccgcta cctggtggtg      420
ttggccactg cggagtcgcg ccgggtggcc ggccgcacct acagcgccgc gcgcgcggtg      480
agcctggccg tgtgggggat cgtcacactc gtcgtgctgc ccttcgcagt cttcgcccgg      540
ctagacgacg agcagggccg gcgccagtgc gtgctagtct ttccgcagcc cgaggccttc      600
tggtggcgcg cgagccgcct ctacacgctc gtgctgggct cgccatcccc cgtgtccacc      660
atctgtgtcc tctataccac cctgctgtgc cggctgcatg ccatgcggct ggacagccac      720
gccaaggccc tggagcgcgc caagaagcgg gtgaccttcc tggtggtggc aatcctggcg      780
gtgtgcctcc tctgctggac gccctaccac ctgagcaccg tggtggcgct caccaccgac      840
ctcccgcaga cgccgctggt catcgctatc tcctacttca tcaccagcct gagctacgcc      900
aacagctgcc tcaaccccct cctctacgcc ttcctggacg ccagcttccg caggaacctc      960
cgccagctga taacttgccg cgcggcagcc tgacactagt                           1000

<210> SEQ ID NO 129
<211> LENGTH: 328
<212> TYPE: PRT
<213> ORGANISM: Human

<400> SEQUENCE: 129

Met Asp Asn Ala Ser Phe Ser Glu Pro Trp Pro Ala Asn Ala Ser Gly
1               5                   10                  15

Pro Asp Pro Ala Leu Ser Cys Ser Asn Ala Ser Thr Leu Ala Pro Leu
            20                  25                  30

Pro Ala Pro Leu Ala Val Ala Val Pro Val Val Tyr Ala Val Ile Cys
        35                  40                  45
```

```
Ala Val Gly Leu Ala Gly Asn Ser Ala Val Leu Tyr Val Leu Leu Arg
 50                  55                  60

Ala Pro Arg Met Lys Thr Val Thr Asn Leu Phe Ile Leu Asn Leu Ala
 65                  70                  75                  80

Ile Ala Asp Glu Leu Phe Thr Leu Val Leu Pro Ile Asn Ile Ala Asp
                 85                  90                  95

Phe Leu Leu Arg Gln Trp Pro Phe Gly Glu Leu Met Cys Lys Leu Ile
                100                 105                 110

Val Ala Ile Asp Gln Tyr Asn Thr Phe Ser Ser Leu Tyr Phe Leu Thr
                115                 120                 125

Val Met Ser Ala Asp Arg Tyr Leu Val Val Leu Ala Thr Ala Glu Ser
                130                 135                 140

Arg Arg Val Ala Gly Arg Thr Tyr Ser Ala Ala Arg Ala Val Ser Leu
145                 150                 155                 160

Ala Val Trp Gly Ile Val Thr Leu Val Val Leu Pro Phe Ala Val Phe
                165                 170                 175

Ala Arg Leu Asp Asp Glu Gln Gly Arg Arg Gln Cys Val Leu Val Phe
                180                 185                 190

Pro Gln Pro Glu Ala Phe Trp Trp Arg Ala Ser Arg Leu Tyr Thr Leu
                195                 200                 205

Val Leu Gly Phe Ala Ile Pro Val Ser Thr Ile Cys Val Leu Tyr Thr
                210                 215                 220

Thr Leu Leu Cys Arg Leu His Ala Met Arg Leu Asp Ser His Ala Lys
225                 230                 235                 240

Ala Leu Glu Arg Ala Lys Lys Arg Val Thr Phe Leu Val Val Ala Ile
                245                 250                 255

Leu Ala Val Cys Leu Leu Cys Trp Thr Pro Tyr His Leu Ser Thr Val
                260                 265                 270

Val Ala Leu Thr Thr Asp Leu Pro Gln Thr Pro Leu Val Ile Ala Ile
                275                 280                 285

Ser Tyr Phe Ile Thr Ser Leu Ser Tyr Ala Asn Ser Cys Leu Asn Pro
                290                 295                 300

Phe Leu Tyr Ala Phe Leu Asp Ala Ser Phe Arg Arg Asn Leu Arg Gln
305                 310                 315                 320

Leu Ile Thr Cys Arg Ala Ala Ala
                325

<210> SEQ ID NO 130
<211> LENGTH: 32
<212> TYPE: DNA
<213> ORGANISM: Artificial Sequence
<220> FEATURE:
<223> OTHER INFORMATION: Primer

<400> SEQUENCE: 130
atcgatatgg acaacgcctc gttctcggag cc                            32

<210> SEQ ID NO 131
<211> LENGTH: 21
<212> TYPE: DNA
<213> ORGANISM: Artificial Sequence
<220> FEATURE:
<223> OTHER INFORMATION: Primer

<400> SEQUENCE: 131
tagaggctgg agaaggtgtt g                                        21
```

```
<210> SEQ ID NO 132
<211> LENGTH: 21
<212> TYPE: DNA
<213> ORGANISM: Artificial Sequence
<220> FEATURE:
<223> OTHER INFORMATION: Primer

<400> SEQUENCE: 132
catgaagacc gtcaccaacc t                                          21

<210> SEQ ID NO 133
<211> LENGTH: 19
<212> TYPE: DNA
<213> ORGANISM: Artificial Sequence
<220> FEATURE:
<223> OTHER INFORMATION: Primer

<400> SEQUENCE: 133
ccagcgtgaa gagctcgtc                                             19

<210> SEQ ID NO 134
<211> LENGTH: 23
<212> TYPE: DNA
<213> ORGANISM: Artificial Sequence
<220> FEATURE:
<223> OTHER INFORMATION: Probe

<400> SEQUENCE: 134
ttcatcctca acctggccat cgc                                        23

<210> SEQ ID NO 135
<211> LENGTH: 20
<212> TYPE: PRT
<213> ORGANISM: Artificial Sequence
<220> FEATURE:
<223> OTHER INFORMATION: Designed peptide

<400> SEQUENCE: 135

Trp Phe Lys His Val Ala Ser Pro Arg Tyr His Thr Val Gly Arg Ala
1               5                   10                  15

Ala Gly Leu Leu
            20
```